United States Patent
Rosselli et al.

(10) Patent No.: US 10,790,454 B2
(45) Date of Patent: Sep. 29, 2020

(54) N AND P ACTIVE MATERIALS FOR ORGANIC PHOTOELECTRIC CONVERSION LAYERS IN ORGANIC PHOTODIODES

(71) Applicants: SONY CORPORATION, Tokyo (JP); SONY DEUTSCHLAND GMBH, Berlin (DE)

(72) Inventors: Silvia Rosselli, Stuttgart (DE); David Danner, Stuttgart (DE); Tzenka Miteva, Stuttgart (DE); Gabriele Nelles, Stuttgart (DE); Vitor Deichmann, Stuttgart (DE); William E. Ford, Stuttgart (DE); Dennis Chercka, Stuttgart (DE); Vladimir Yakutkin, Stuttgart (DE); Lars Peter Scheller, Stuttgart (DE); Nikolaus Knorr, Stuttgart (DE)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/560,857

(22) PCT Filed: Mar. 31, 2016

(86) PCT No.: PCT/EP2016/057144
§ 371 (c)(1),
(2) Date: Sep. 22, 2017

(87) PCT Pub. No.: WO2016/156535
PCT Pub. Date: Oct. 6, 2016

(65) Prior Publication Data
US 2018/0123050 A1  May 3, 2018

(30) Foreign Application Priority Data
Mar. 31, 2015 (EP) .................................. 15161993

(51) Int. Cl.
*H01L 51/00* (2006.01)
*C07D 221/14* (2006.01)
(Continued)

(52) U.S. Cl.
CPC ........ *H01L 51/0072* (2013.01); *C07D 221/14* (2013.01); *C07D 471/06* (2013.01);
(Continued)

(58) Field of Classification Search
CPC ............. H01L 51/0072; H01L 51/0052; H01L 51/0053; H01L 51/0058; H01L 51/006;
(Continued)

(56) References Cited

U.S. PATENT DOCUMENTS

| 6,387,727 B1 | 5/2002 | Katz et al. |
| 7,569,693 B2 * | 8/2009 | Marks .................. C07D 471/06 438/141 |

(Continued)

FOREIGN PATENT DOCUMENTS

| EP | 2 498 315 A2 | 9/2012 |
| EP | 2498315 | * 9/2012 |

(Continued)

OTHER PUBLICATIONS

Bhosale et al., The synthesis of novel core-substituted naphthalene diimides via Suzuki cross-coupling and their properties, New Jorunal of Chemistry, RSC, vol./Issue 33, pp. 2409-2413 (Year: 2009).*
(Continued)

*Primary Examiner* — Jayne L Mershon
(74) *Attorney, Agent, or Firm* — Oblon, McClelland, Maier & Neustadt, L.L.P.

(57) ABSTRACT

The field of the DISCLOSURE lies in active materials for organic image sensors. The present disclosure relates to transparent N materials and/or to transparent P materials and their use in absorption layer(s), photoelectric conversion
(Continued)

layer(s) and/or an organic image sensor and methods for their synthesis. The present disclosure also relates to photoelectric conversion layer(s) including an active material according to the present disclosure, to a device, including active material(s) according to the present disclosure or photoelectric conversion layer(s) according to the present disclosure. Moreover, the present disclosure relates to an organic image sensor including photoelectric conversion layer(s) according to the present disclosure.

20 Claims, 39 Drawing Sheets

(51) Int. Cl.
| | |
|---|---|
| C07D 471/06 | (2006.01) |
| C07D 495/04 | (2006.01) |
| C07D 519/00 | (2006.01) |
| C07D 495/14 | (2006.01) |
| C07F 3/06 | (2006.01) |
| H01L 27/30 | (2006.01) |
| H01L 51/50 | (2006.01) |
| H01L 51/42 | (2006.01) |
| H01L 51/05 | (2006.01) |
| H01L 27/28 | (2006.01) |
| H01L 31/028 | (2006.01) |

(52) U.S. Cl.
CPC ......... *C07D 495/04* (2013.01); *C07D 495/14* (2013.01); *C07D 519/00* (2013.01); *C07F 3/06* (2013.01); *H01L 51/006* (2013.01); *H01L 51/0052* (2013.01); *H01L 51/0053* (2013.01); *H01L 51/0058* (2013.01); *H01L 51/0061* (2013.01); *H01L 51/0067* (2013.01); *H01L 51/0068* (2013.01); *H01L 51/0071* (2013.01); *H01L 51/0092* (2013.01); *H01L 27/286* (2013.01); *H01L 27/307* (2013.01); *H01L 31/028* (2013.01); *H01L 51/0512* (2013.01); *H01L 51/42* (2013.01); *H01L 51/4253* (2013.01); *H01L 51/5072* (2013.01); *Y02E 10/549* (2013.01)

(58) Field of Classification Search
CPC ............. H01L 51/0061; H01L 51/0067; H01L 51/0068; H01L 51/0071; H01L 51/0092; C07D 221/14; C07D 471/06; C07D 495/14; C07D 495/04; C07D 519/00; C07F 3/06

See application file for complete search history.

(56) References Cited

U.S. PATENT DOCUMENTS

| | | | |
|---|---|---|---|
| 7,816,713 B2 | 10/2010 | Kim et al. | |
| 7,936,035 B2 | 5/2011 | Maehara et al. | |
| 8,053,661 B2 | 11/2011 | Mitsui et al. | |
| 8,309,394 B2* | 11/2012 | Shukla | H01L 51/0053 257/E51.027 |
| 8,525,577 B2 | 9/2013 | Yofu et al. | |
| 8,822,980 B2* | 9/2014 | Hayashi | H01L 27/14645 257/40 |
| 2005/0217722 A1 | 10/2005 | Komatsu et al. | |
| 2011/0308592 A1 | 12/2011 | Könemann et al. | |
| 2012/0049044 A1 | 3/2012 | Kuboi | |
| 2012/0211082 A1 | 8/2012 | Akiyama et al. | |
| 2013/0324723 A1* | 12/2013 | Langer | C07D 487/06 544/247 |
| 2013/0342722 A1 | 12/2013 | Kuboi | |
| 2014/0160327 A1 | 6/2014 | Enoki et al. | |
| 2014/0213789 A1* | 7/2014 | Polander | C07D 471/06 546/4 |
| 2015/0051398 A1* | 2/2015 | Schimperna | C07D 471/06 546/66 |
| 2015/0333264 A1* | 11/2015 | Mishra | C08G 61/126 528/8 |
| 2016/0104846 A1* | 4/2016 | Gebner | C07D 471/22 546/32 |

FOREIGN PATENT DOCUMENTS

| | | |
|---|---|---|
| JP | 2010-93181 A | 4/2010 |
| JP | 2010-93181 A | 4/2010 |
| JP | 2010-141268 A | 6/2010 |
| JP | 2010-254608 A | 11/2010 |
| JP | 2010-254608 A | 11/2010 |
| JP | 2014-51583 A | 3/2014 |
| JP | 2014-179537 A | 9/2014 |
| KR | 10-2007-000891 A | 1/2007 |
| KR | 10-2010-0079600 A | 7/2010 |
| WO | 2006/100545 A1 | 9/2006 |
| WO | 2010/006698 A1 | 1/2010 |
| WO | 2012/142460 A1 | 10/2012 |
| WO | 2013/024409 A1 | 2/2013 |
| WO | 2013/042414 A1 | 3/2013 |
| WO | 2014/031750 A1 | 2/2014 |
| WO | 2014/038708 A1 | 3/2014 |

OTHER PUBLICATIONS

Feng et al., Alternate redox electrolytes in dye-sensitized solar cells, Special Issues: New Energy Materials, Chinese Science Bulletin, vol. 57, No. 32, pp. 4131-4142 (Year: 2012).*
Hwang et al., n-Type Naphthalene Diimide-Biselenophene Copolymer for All-Polymer Bulk Heterojunction Solar Cells, Macromolecules, ACS Publications, vol./Issue 45, pp. 9056-9062 (Year: 2012).*
Yan et al., A high-mobility electron-transporting polymer for printed transistors, Nature, vol. 457, pp. 679-686 (Year: 2009).*
Rhodes et al., Perylenemonoimide-Naphthalenediimide (PMI-NDI), downloaded Nov. 13, 2019, slide 10 of 11. (Year: 2008).*
Tobin Jay Marks, et al., "Cyanonaphthalene diimide semiconductors for air-stable, flexible, and optically transparent n-channel field-effect transistors," Chemistry of Materials, vol. 19, No. 11, 2007, (2 pages) (Abstract only).
Deepak Shukla, et al., "Thin-Film Morphology Control in Naphthalene-Diimide-Based Semiconductors: High Mobility n-Type Semiconductor for Organic Thin-Film Transistors," Chemistry of Materials, vol. 20, No. 24, 2008 (3 pages) (Abstract only).
M. Stolte, et al., "Organic n-channel thin film transistors based on dichlorinaed naphthalene diimides," SPIE Proceedings, vol. 7778, Materials I, Aug. 17, 2010, (3 pages) (Abstract only).
Myoung-Chul Um, et al., "High-performance organic semiconductors for thin-film transistors based on 2,7-divinyl[1]benzothieno[3,2-b]benzothiophene," Journal of Materials Chemistry, vol. 18, 2008, (4 pages) (Abstract only).
Kazuo Takimiya, et al., "2,7-Diphenyl[1]benzothieno[3,2-b]benzothiophene, A New Organic Semiconductor for Air-Stable Organic Field-Effect Transistors with Mobilities up to 2.0 $cm^2 V^{-1} s^{-1}$," Journal of the American Chemical Society, vol. 128, No. 39, 2006, (3 pages) (Abstract only).
Xuan Zhang, et al., "Dithienopyrrole-based donor—acceptor copolymers: low band-gap materials for charge transport, photovoltaics and electrochromism," Journal of Materials Chemisty, vol. 20, 2010, (2 pages) (Abstract only).
Sheshanath V. Bhosale, et al., "The synthesis of novel core-substituted naphthalene diimides via Suzuki cross-coupling and their properties," New Journal of Chemistry, vol. 33, 2009, pp. 2409-2413.
International Search Report dated Aug. 19, 2016 in PCT/EP2016/057144 filed Mar. 31, 2016.
Office Action dated Dec. 4, 2018 in corresponding Japanese Patent Application No. 2017-551635 (with English Translation), 10 pages.
Combined Chinese Office Action and Search Report dated Mar. 4,

(56) References Cited

OTHER PUBLICATIONS 2020 in Chinese Patent Application No. 201680017925.4 (with English translation), 13 pages.
Ye, H., et al., Optical Materials and Optical Components Fabrication Process, Zhejiang University Press, Feb. 28, 2014, pp. 218-219.
Dai, S., "Key Science and Technology of Thin Film Solar Cells", Shanghai Scientific and TTechnical Publishers, Jan. 31, 2013, pp. 131-134.
Wang,Y., et al., "Non-Vacuum Preparation of thin-film Solar Cells", Metallurgical Industry Press, Apr. 30, 2014, pp. 46-58.
Ao, D., "The Story of Semiconductors", University of Science and Technology of China Press, Jan. 31, 2015, pp. 431-434.

* cited by examiner

P:N = QD:NDI1 (1:1)

P:N = BQD:NDI1 (1:1)

P:N = SubPcCl:NMI-NDI1 (1:1),
As deposited

P:N = SubPcCl:NDI1 (1:1),
As deposited

Figure 14

| Material | DMF solution | | TF-film |
|---|---|---|---|
| | Abs. max., nm | Ems. max., nm | Abs. max., nm |
| NDI21 | 382 | 423 | 381 |
| NDI23 | 383 | 405, 429 | 378 |
| NDI24 | 379 | 401, 425 | 385 |
| NDI26 | 379 | 431, 540 | 403 |
| NDI28 | 379 | 402, 430, 570 | 381 |
| NDI29 | 385 | 429, 554 | 375 |
| NDI35 | 380 | 432, 570 | 394 |
| NDI36 | 382 | 425, 530 | 387 |
| NDI37 | 382 | 504 | 387 |
| NDI38 | 380 | 430, 530 | 385 |

Figure 17 A

| Material | Structure | HOMO calc (TM) | LUMO calc (TM) | HOMO exp (Au/ITO) | LUMO exp (Au/ITO) | Ef Exp (Au/ITO) | Sublimation | Decomposition |
|---|---|---|---|---|---|---|---|---|
| NDI21 | 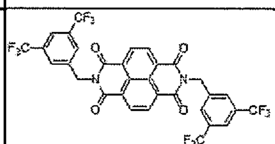 | -7.614 | -4.007 | -8.6 / -9.0 | -5.5 / -5.9 | -5.1 / -5.3 | 170°C | 270°C |
| NDI23 | 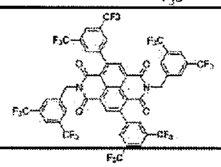 | -7.817 | -4.343 | -8.1 / -8.4 | -5.1 / -5.3 | -4.9 / -5.2 | 210°C | - |
| NDI24 | 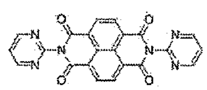 | -7.128 | -3.492 | -7.1 / -7.3 | -4.0 / -4.3 | -4.0 / -4.3 | - | 380°C |
| NDI26 | 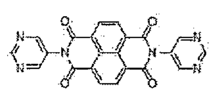 | -7.301 | -3.999 | -7.8 / -8.5 | -4.9 / -5.6 | -4.4 / -5.2 | 250°C | 400°C |
| NDI28 | 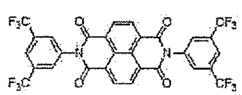 | -7.685 | -4.059 | -8.2 / -8.7 | -5.1 / -5.6 | -4.7 / -5.1 | 180°C | 300°C |

Figure 17 B

| Material | Structure | HOMO calc (TM) | LUMO calc (TM) | HOMO exp (Au/ITO) | LUMO exp (Au/ITO) | Ef Exp (Au/ITO) | Sublimation | Decomposition |
|---|---|---|---|---|---|---|---|---|
| NDI29 | 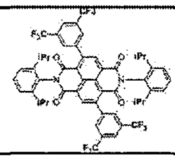 | -6.809 | -3.953 | -7.5 / -7.7 | -4.4 / -4.6 | -4.4 / -4.7 | 180°C | 340°C |
| NDI35 | 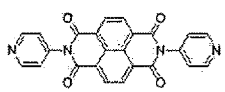 | -7.379 | -3.833 | -7.6 / -7.9 | -4.6 / -5.0 | -4.0 / -4.3 | 200°C | 360°C |
| NDI36 | 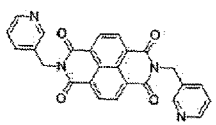 | -7.065 | -3.756 | -7.4 / -7.6 | -4.3 / -4.6 | -3.8 / -4.1 | 180°C | 340°C |
| NDI37 | 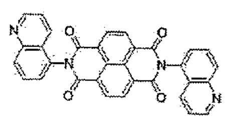 | -6.766 | -3.731 | -6.9 / -7.2 | -3.9 / -4.2 | -3.9 / -4.2 | 300°C | 380°C |
| NDI38 | 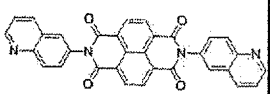 | -6.742 | -3.658 | -6.9 / -7.1 | -3.9 / -4.1 | -3.9 / -4.2 | 300°C | 420°C |

Figure 18 A

| Material | Structure | $\lambda_{Max,UV-Vis}$ Solution (nm) | $\Delta E_{OP}$ (eV) | $\lambda_{Max,UV-Vis}$ Film (nm) | $\lambda_{Max,PL}$ Solution (nm) |
|---|---|---|---|---|---|
| TAT4 | 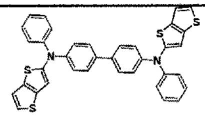 | 343 | 3.10 | 352 | 420 (br) |
| ATA3 | 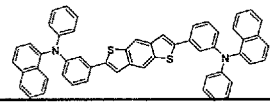 | 347 | 3.05 | 354 | 404, 427 |
| ATA4 | 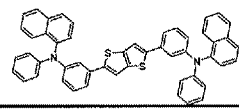 | 353 | 3.07 | 362 | 406, 428 |
| ATA5 | 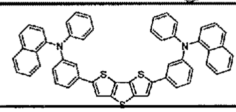 | 372 | 2.93 | 381 | 423, 445 |
| ATA6 | 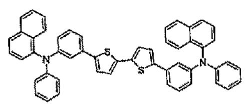 | 365 | 2.83 | 377 | 439, 465 |
| C2-Th | 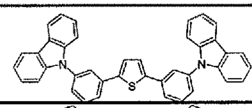 | 341 | 3.27 | 346 | 380, 399 |
| C2-TT | 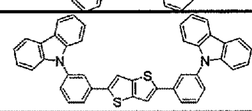 | 342 | 3.13 | 353 | 395, 416 |
| C2-DTT | 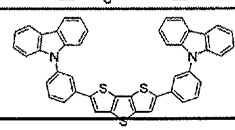 | 378 | 2.96 | 385 | 418, 441 |

| Material | Structure | $\lambda_{Max,UV-Vis}$ Solution (nm) | T decomp (°C) |
|---|---|---|---|
| DTT2 | 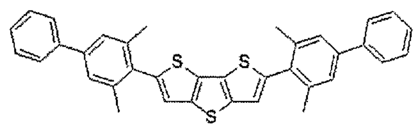 | 319 | 320 |
| DTT9 | 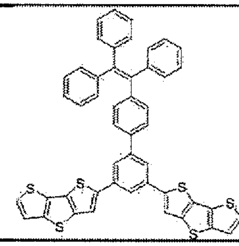 | 349 | 380 |
| DTT10 | 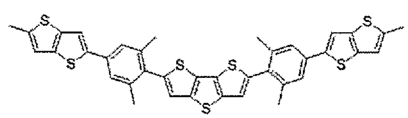 | 340 | 380 |
| DTT11 | 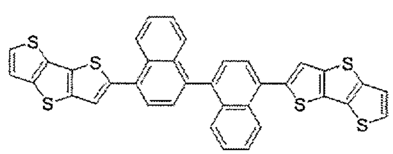 | 351 | 389 |

| | | |
|---|---|---|
| LiF | 150 nm | |
| AlSiCu | 100 nm | |
| NDI35 | 10 nm | |
| DTT9:F6-OC6F5 (1:1) | 200 nm | |
| ST1163 | 10 nm | |
| ITO | | |
| glass | | |

| Material | i-layer | p-buffer | n-buffer | ANL | EQE 0V | EQE -1V | $J_{dark}$ A/cm² | EDE, % | Mobility i-layer cm²/Vs | HOMO eV | LUMO eV |
|---|---|---|---|---|---|---|---|---|---|---|---|
| DTT2 | DTT2:F6-OC6F5 (1:1) 200nm | ST1163 10nm | NDI35 10nm | as depo | 17.5 | 21.6 | 2.9E-10 | NM | 1E-9 to 1E-7 | -5.6 | -2.3 |
| DTT9 | DTT9:F6-OC6F5 (1:1) 200nm | ST1163 10nm | NDI35 10nm | as depo | 5.4 | 7.4 | 2.5E-9 | 17 ± 3 | 1E-10 | | |
| DTT10 | DTT10:F6-OC6F5 (1:1) 200nm | HTM065 10nm | NDI35 10nm | as depo | 4.4 | 6.9 | 2.4E-10 | 65± 3 | | | |
| DTT11 | DTT11:F6-OC6F5 (1:1) 210nm | HTM065 10nm | NDI35 10nm | as depo | 9.4 | 11.8 | 2.8E-10 | 15 ± 3 | | | |

| | | |
|---|---|---|
| LiF | 150 nm | |
| AlSiCu | 100 nm | |
| NDI35 | 10 nm | |
| DTT9:F6-OC6F5 (1:1) | 200 nm | |
| HTM065 | 10 nm | |
| ITO | | |
| glass | | |

| Material | i-layer | p-buffer | n-buffer | ANL | EQE 0V | EQE -1V | $J_{dark}$ A/cm² | EDE, % | Mobility i-layer cm²/Vs | HOMO eV | LUMO eV |
|---|---|---|---|---|---|---|---|---|---|---|---|
| DTT2 | DTT2:F6-OC6F5 (1:1) 200nm | ST1163 10nm | NDI35 10nm | as depo | 17.5 | 21.6 | 2.9E-10 | NM | 1E-9 to 1E-7 | -5.6 | -2.3 |
| DTT9 | DTT9:F6-OC6F5 (1:1) 200nm | ST1163 10nm | NDI35 10nm | as depo | 5.4 | 7.4 | 2.5E-9 | 17 ± 3 | 1E-10 | | |
| DTT10 | DTT10:F6-OC6F5 (1:1) 200nm | HTM065 10nm | NDI35 10nm | as depo | 4.4 | 6.9 | 2.4E-10 | 65 ± 3 | | | |
| DTT11 | DTT11:F6-OC6F5 (1:1) 210nm | HTM065 10nm | NDI35 10nm | as depo | 9.4 | 11.8 | 2.8E-10 | 15 ± 3 | | | |

… 
N AND P ACTIVE MATERIALS FOR ORGANIC PHOTOELECTRIC CONVERSION LAYERS IN ORGANIC PHOTODIODES

CROSS REFERENCE TO RELATED APPLICATIONS

The present application claims the benefit of the filing date of European application no. 15161993.9, filed on Mar. 31, 2015, the entire contents of which are incorporated by reference.

BACKGROUND

The field of the DISCLOSURE lies in active materials for organic image sensors.

The present disclosure relates to transparent N materials and/or to transparent P materials and their use in absorption layer(s), photoelectric conversion layer(s) and/or an organic image sensor and methods for their synthesis.

The present disclosure also relates to photoelectric conversion layer(s) including an active material according to the present disclosure, to a device, including active material(s) according to the present disclosure or photoelectric conversion layer(s) according to the present disclosure.

Moreover, the present disclosure relates to an organic image sensor including photoelectric conversion layer(s) according to the present disclosure.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Image sensors, which are semiconductor devices for converting an optical image into an electric signal, include a light-sensing unit for sensing light and a logic circuit unit for processing the sensed light into an electrical signal to store data.

In the state of the art, the light-sensing unit includes a color filter and a photoelectric conversion film, a semiconductor p-n junction, such as silicon. The color filter separates light according to colors, but reduces the spatial resolution and light collection and utilization efficiency.

In order to overcome this problem geometries are reported where photoelectric conversion units capable of detecting light of different wavelengths are stacked in a longitudinal direction. In particular such photoelectrical conversion unit is an organic photoelectric conversion layer based on p-n junction or bulk heterojunction. The photoelectric conversion efficiency of such a unit depends strongly on the type of materials used in the layer. With the organic materials available so far, low conversion efficiencies and high dark currents are reported.

In another solution, an organic layer is used that is capable to absorb in the IR region but not in the visible reagion, that could be combined with a complementary metal oxide semiconductor (CMOS) based imager part for the visible range or with an organic based imager part that could absorb in the visible range. In both cases white light is collected and filter have to be used to get the BGR pixel resolution. In this case, as well as in the case of color filter, light is separated according to colors but the spatial resolution and light collection and utilization efficiency is reduced.

SUMMARY

The present disclosure provides a transparent N material, which has the quality when included in a P:N heterojunction or bilayer or multilayer junction, preferably a P1:P2:N1:N2 or P1:P2:N or P:N1:N2 heterojunction or multilayer junction, to dissociate efficiently the excitons created on colored P or a mixture of colored P materials (P1:P2) or of another colored N or mixture of colored N and P materials (P:N2 or P1:P2:N2) via a process of LUMO dissociation, accepting electron from the excited state of the donor (the P material(s) or the N material(s) absorbing photons), wherein transparent refers to an absorption coefficient of less than about 60,000 $cm^{-1}$ in the visible wavelength range (about 400 to about 700 nm), or to an extinction coefficient of less than about 60,000 $M^{-1}$ $cm^{-1}$ (in toluene), and colored refers to an absorption coefficient of more than about 60,000 $cm^{-1}$ in the visible wavelength range in the region from about 400 nm to about 700 nm (with maxima anywhere in this region or absorbing everywhere in this region).

The present disclosure provides a transparent P material, which has the quality when included in a P:N heterojunction or P:N bilayer or multilayer junction, preferably a P1:P2:N1:N2 or a P1:P2:N1 or a P:N1:N2 heterojunction or multilayer junction, to dissociate efficiently the excitons created on colored N or a mixture of colored N materials (N1:N2) materials or of another colored P or mixture of colored P and N materials (P2:N or P2:N1:N2)

via a process of HOMO dissociation, donating electron into the HOMO of the excited colored material (the P material(s) or the N material(s) absorbing photons) which is equivalent to accepting a hole, wherein transparent refers to an absorption coefficient of less than about 60,000 $cm^{-1}$ in the visible wavelength range (about 400 to about 700 nm), or to an extinction coefficient of less than about 60,000 $M^{-1}$ $cm^{-1}$ (in toluene), and colored refers to an absorption coefficient of more than about 60,000 $cm^{-1}$ in the visible wavelength range in the region from about 400 nm to about 700 nm (with maxima anywhere in this region or absorbing everywhere in this region).

The present disclosure provides a P:N heterojunction, preferably a P1:P2:N1:N2 heterojunction, including a transparent N material according to the present disclosure and/or a transparent P material according to the present disclosure, and including a further N and/or P material, wherein the further N and/or P material preferably exhibits absorption in the visible wavelength range (about 400 to about 700 nm).

The present disclosure provides the use of a transparent N and/or P material according to the present disclosure in an absorption layer and/or in a photoelectric conversion layer and/or in an organic and/or hybrid module for optoelectronic application.

The present disclosure provides a photoelectric conversion layer including a transparent N and/or P material according to the present disclosure. The present disclosure provides an absorption layer including a transparent N and/or P material according to the present disclosure.

The present disclosure provides a device including transparent N and/or P material(s) according to the present disclosure or a photoelectric conversion layer(s) according to the present disclosure.

The present disclosure provides an organic image sensor, including an organic photoelectric conversion unit including photoelectric conversion layer(s) according to the present disclosure.

The present disclosure provides a hybrid Silicon-organic image sensor, including an organic photoelectric conversion unit including photoelectric conversion layer(s) according to the present disclosure.

The present disclosure provides a method for synthesis of transparent n and p materials, in particular naphtalene monoimide dimer (NMI dimer)-based materials, naphtalene diimide (NDI)-based materials, naphtalene diimide dimer (NDI dimer)-based materials, naphtalene mono-diimide dimer (NMI-NDI)-based materials, dithioenopyrrol dimer (DTP dimer)-based materials and zinc coordination complex-based materials.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 14 shows the absorption for NDI materials with general foiniula Ia.

FIGS. 17A and FIG. 17B show energy levels of N-buffer materials with general formula Ia.

DETAILED DESCRIPTION OF THE EMBODIMENTS

Figure 1:
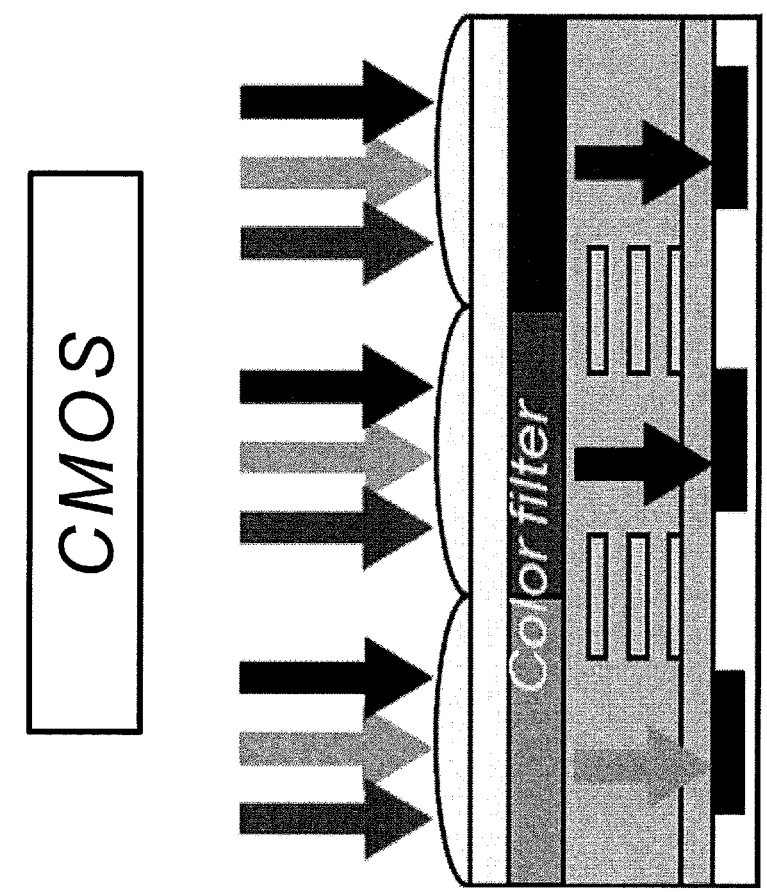
FIG. 1 shows a CMOS image sensor.

As discussed above, the present disclosure provides a transparent N material.

The transparent N material according to the present disclosure has the quality when included in a P:N heterojunction or bilayer or multilayer junction, preferably a P1:P2:N1:N2 or P1:P2:N or P:N1:N2 heterojunction or multilayer junction, to dissociate efficiently the excitons created on colored P or a mixture of colored P materials (P1:P2) or of another colored N or mixture of colored N and P materials (P:N2 or P1:P2:N2) via a process of LUMO dissociation.

According to the present disclosure, the transparent N material accepts electron from the excited state of the donor (the P material(s) or the N material(s) absorbing photons)). wherein transparent refers to an absorption coefficient of less than about 60,000 cm$^{-1}$ in the visible wavelength range (about 400 to about 700 nm), or to an extinction coefficient of less than about 60,000 M$^{-1}$ cm$^{-1}$ (in toluene), and colored refers to an absorption coefficient of more than about 60,000 cm$^{-1}$ in the visible wavelength range in the region from about 400 nm to about 700 nm (with maxima anywhere in this region or absorbing everywhere in this region).

As discussed above, the present disclosure provides a transparent P material.

The transparent P material according to the present disclosure has the quality when included in a P:N heterojunction or P:N bilayer or multilayer junction, preferably a P1:P2:N1:N2 or a P1:P2:N1 or P:N1:N2 heterojunction or multilayer junction, to dissociate efficiently the excitons created on colored N or a mixture of colored N materials (N1:N2) or of another colored P or mixture of colored P and N materials (P2:N or P2:N1:N2) via a process of HOMO dissociation.

According to the present disclosure, the transparent P material donates electron into the HOMO of the excited colored material (the P material(s) or the N material(s) absorbing photons), which is equivalent to accepting a hole.

According to the present disclosure "transparent" refers to an absorption coefficient of less than about 60,000 cm$^{-1}$ in the visible wavelength range (about 400 to about 700 nm), or to an extinction coefficient of less than about 60,000 M$^{-1}$ cm$^{-1}$ (in toluene), and "colored" refers to an absorption coefficient of more than about 60,000 cm$^{-1}$ in the visible wavelength range in the region from about 400 nm to about 700 nm (with maxima anywhere in this region or absorbing everywhere in this region).

In one embodiment, the transparent N and/or P material of the present disclosure exhibits no or very low absorption in the visible wavelength range (about 400 to about 700 nm), i.e. has an absorption coefficient of less than about 60,000 cm$^{-1}$ in the visible wavelength range (about 400 to about 700 nm), or has an extinction coefficient of less than about 60,000 M$^{-1}$ cm$^{-1}$ (in toluene), is an organic based compound forming high quality homogenous films when using deposition methods (such as vacuum deposition or spincoating).

In one embodiment, the transparent N and/or P material of the present disclosure is selected from the group of naphtalene monoimides (NMI), naphtalene dimides (NDI), dimers of naphtalene monoimides and/or naphtalene dimides (NMI-NMI, NDI-NDI or NMI-NDI), thiophene- or selenophene-based materials, dithienopyrrol (DTP)-based and DTP-dimer materials, anthracene-based materials, and zinc coordination complexes.

In one embodiment, the transparent N and/or P material of the present disclosure is a naphtalene monoimide (NMI)-based material represented by the general formula I

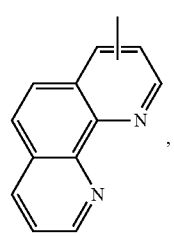

I wherein
R is selected from —$C_xH_{2x+1}$, —$C_xX_{2x+1}$, —$C_xH_2X_{2x-1}$,

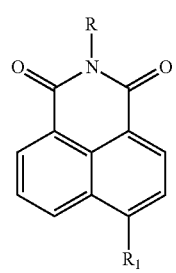

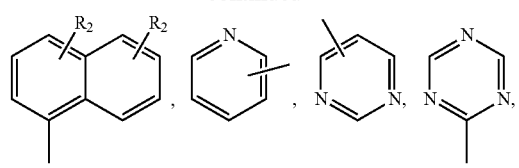

and
$R_1$ is selected from

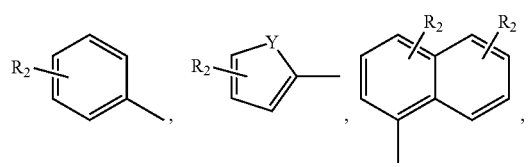

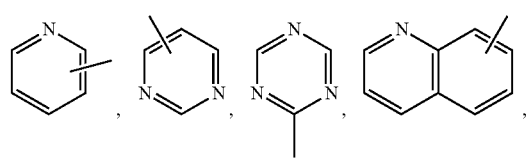

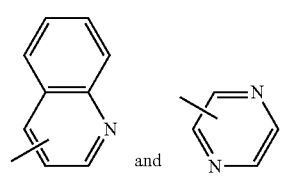

x is an integer from 1 to 10,

X is halogen (F, Cl, Br, I),

Y is selected from $CH_2$, S, O, Se and N—$R_2$, $R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

In a preferred embodiment of the naphtalene monoimide (NMI)-based material represented by the general formula I,

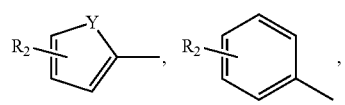

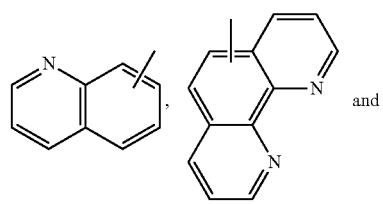

R is selected from
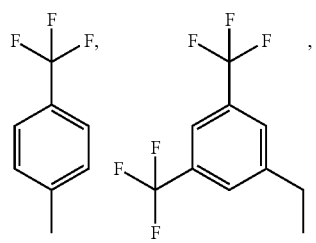
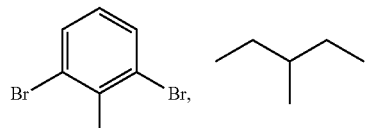
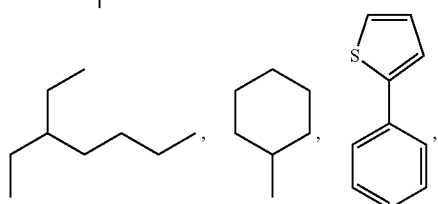
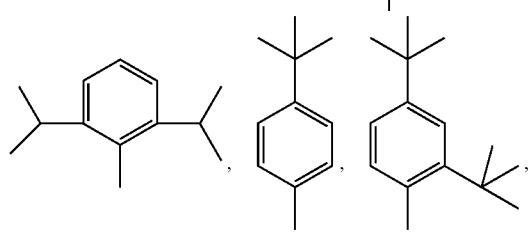
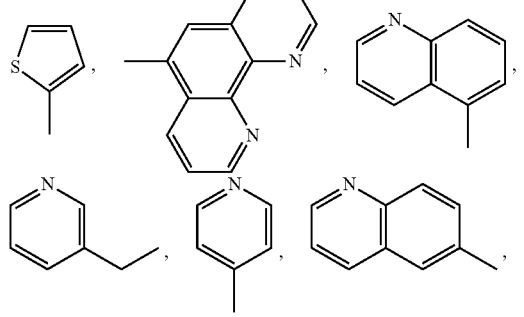
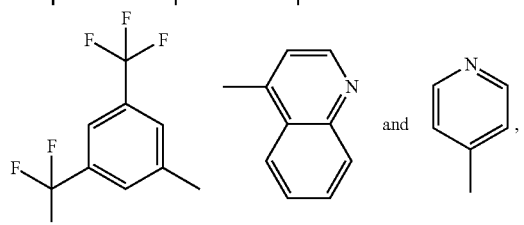
and/or
$R_1$ is selected from
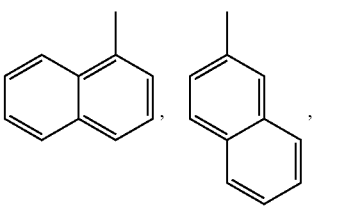
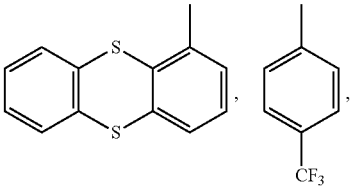
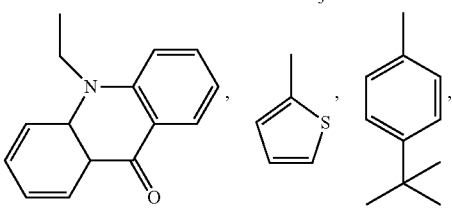
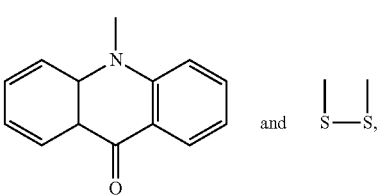
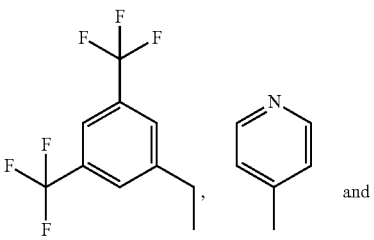
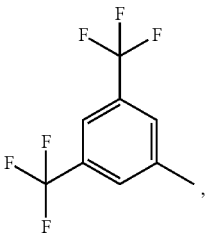
In one embodiment, the transparent N and/or P material of the present disclosure is a naphtalene monoimide dimer (NMI-NMI)-based material represented by the general formula II

II

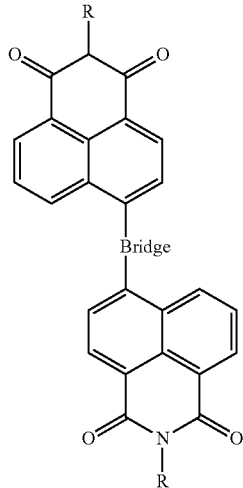

wherein

R is, at each occurrence, independently selected from $-C_xH_{2x+1}$, $-C_xX_{2x+1}$, $-C_xH_2X_{2x-1}$,

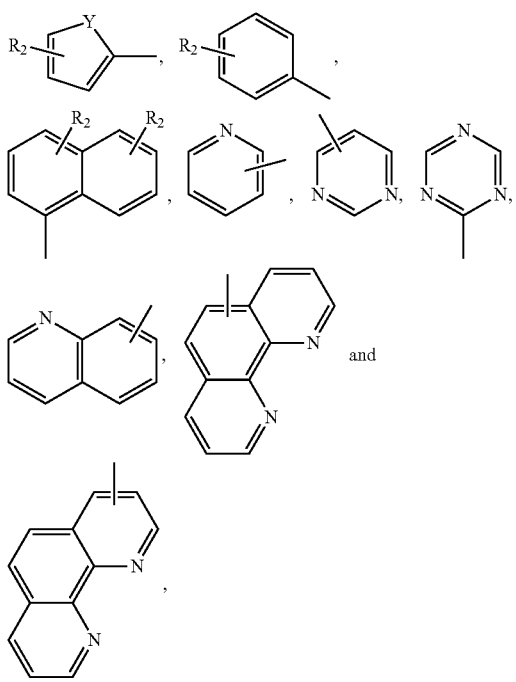

and
Bridge is selected from

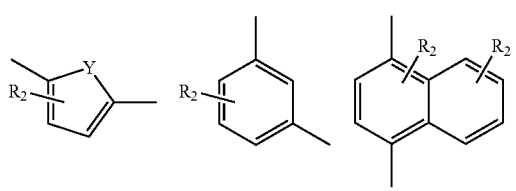

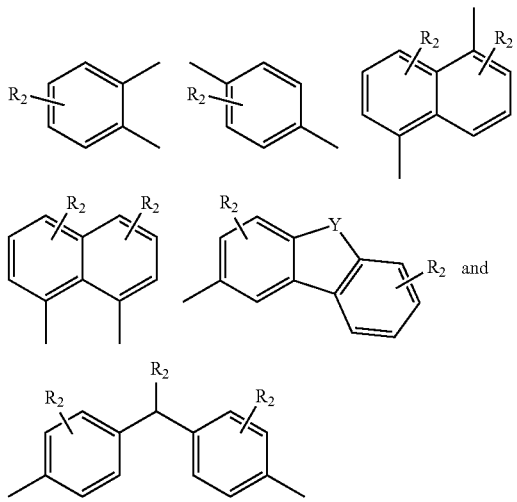

x is an integer from 1 to 10,
X is halogen (F, Cl, Br, I),
Y is selected from $CH_2$, S, O, Se and $N-R_2$,
$R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

In a preferred embodiment of the naphtalene monoimide monoimide dimer (NMI-NMI)-based material represented by the general formula II,
R is selected from

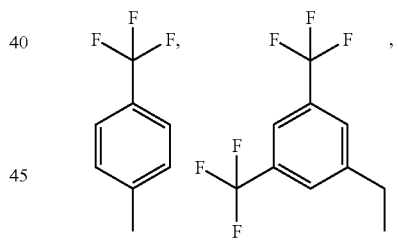

$-(CF_2)_5CF_3$, $-(CH_2)_5CH_3$, $-CH_2-(CF_2)_3-CF_3$,

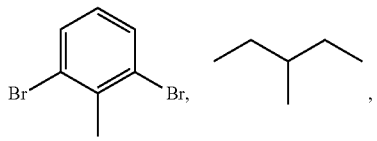

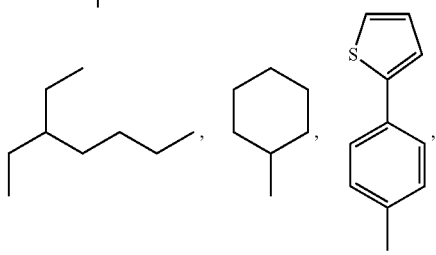

-continued
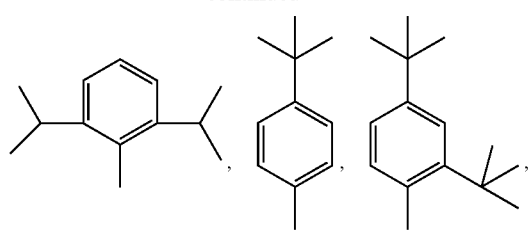
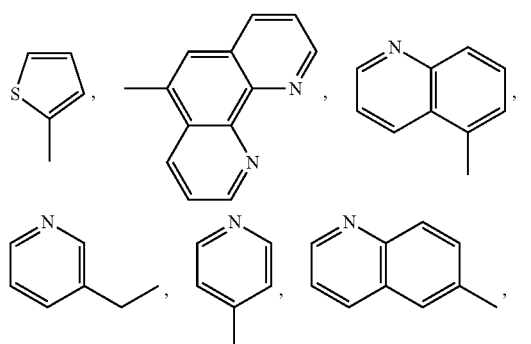
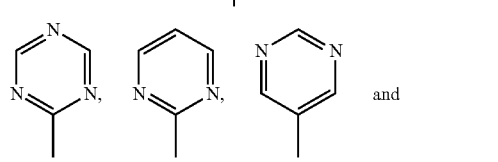
and/or
Bridge is selected from
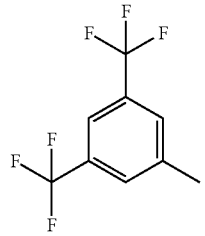
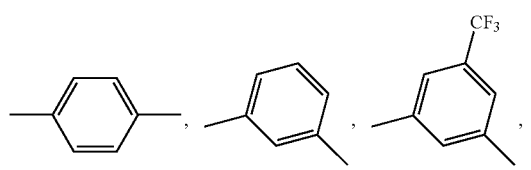
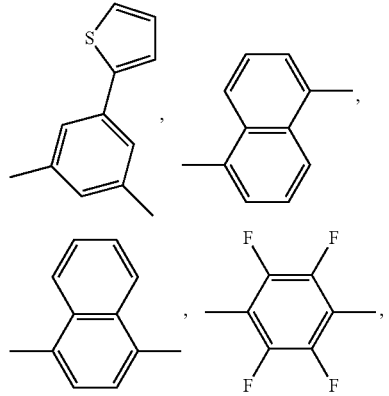
-continued
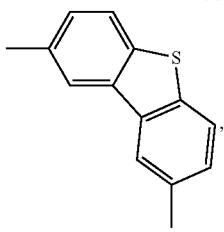
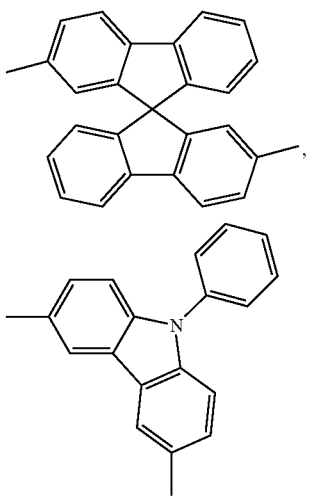
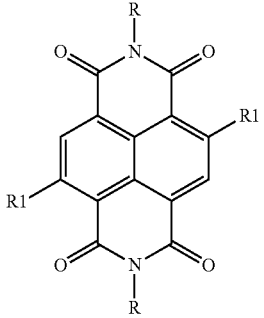
and none (i.e. a direct connection).
In one embodiment, the transparent N and/or P material of the present disclosure is a naphtalene diimide (NDI)-based material represented by the general formula III
III
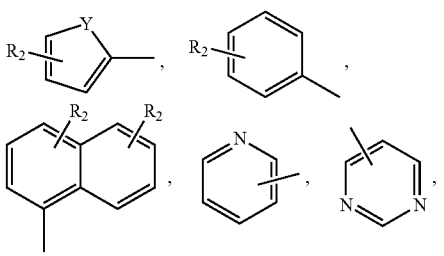
wherein
R is, at each occurrence, independently selected from $-C_xH_{2x+1}$, $-C_xX_{2x+1}$, $-C_xH_2X_{2x-1}$, -continued

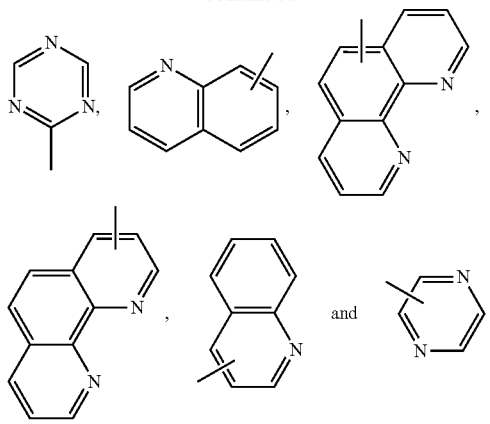

$R_1$ is, at each occurrence, independently selected from

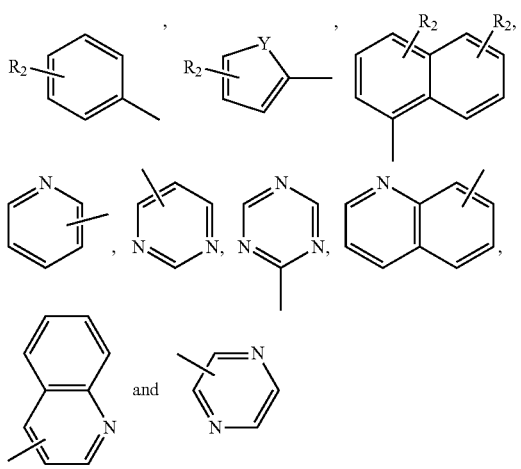

x is an integer from 1 to 10,
X is halogen (F, Cl, Br, I),
Y is selected from $CH_2$, S, O, Se and N—$R_2$,
$R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

In a preferred embodiment of the naphtalene diimide (NDI)-based material represented by the general formula III R is selected from

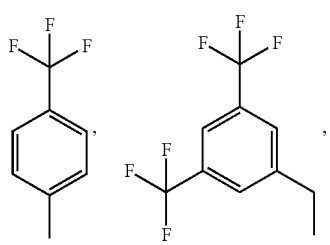

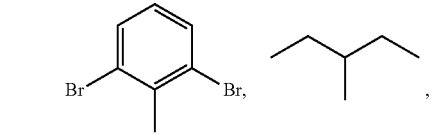

—$(CF_2)_5CF_3$, —$(CH_2)_5CH_3$, —$CH_2$—$(CF_2)_3$—$CF_3$,

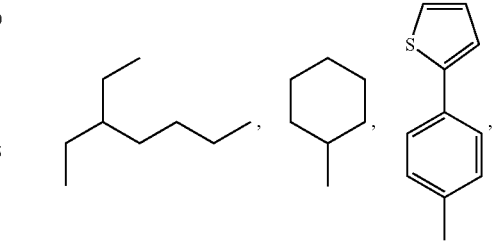

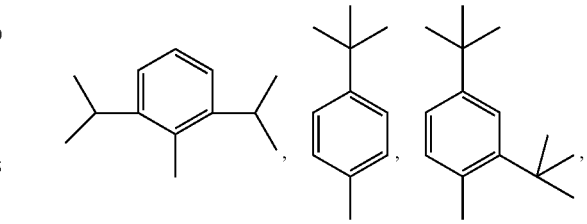

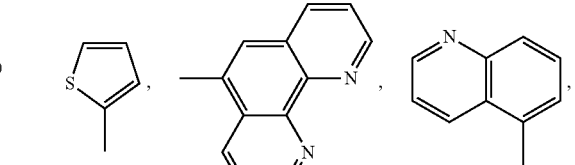

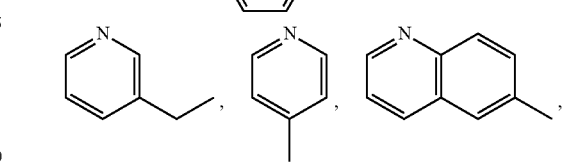

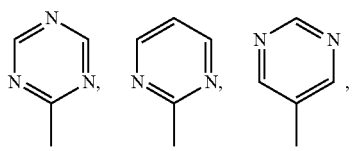

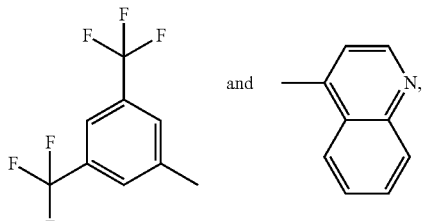

and/or
$R_1$ is selected from

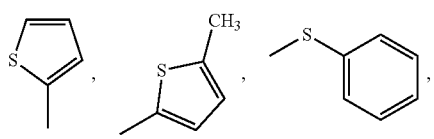

-continued

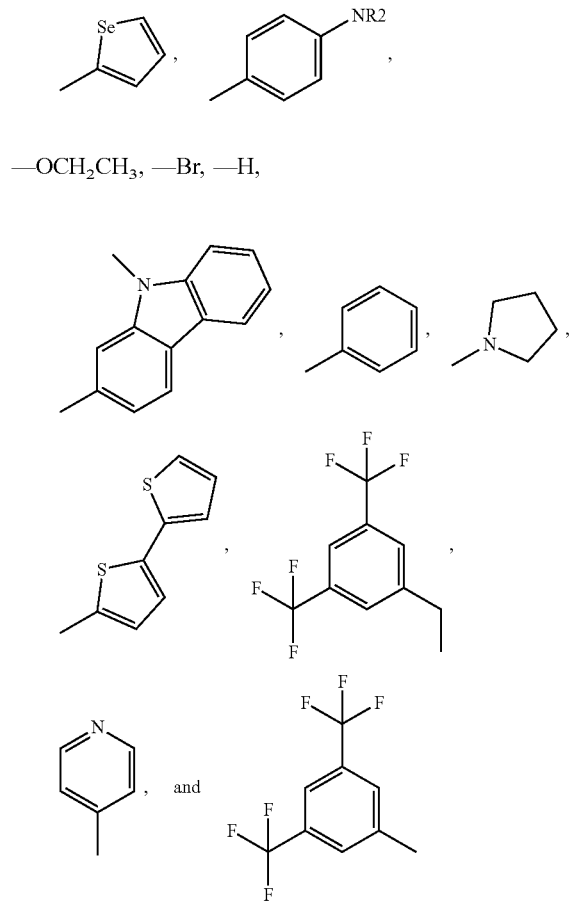

—OCH$_2$CH$_3$, —Br, —H,

In one embodiment, the transparent N and/or P material of the present disclosure is a naphtalene diimide (NDI)-based material represented by the general formula IIIa

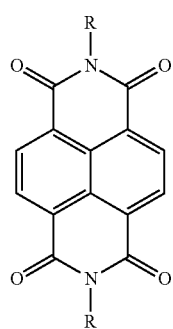

IIIa wherein

R is, at each occurrence, independently selected from —C$_x$H$_{2x+1}$, —C$_x$X$_{2x+1}$, —C$_x$H$_2$X$_{2x-1}$,

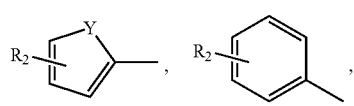

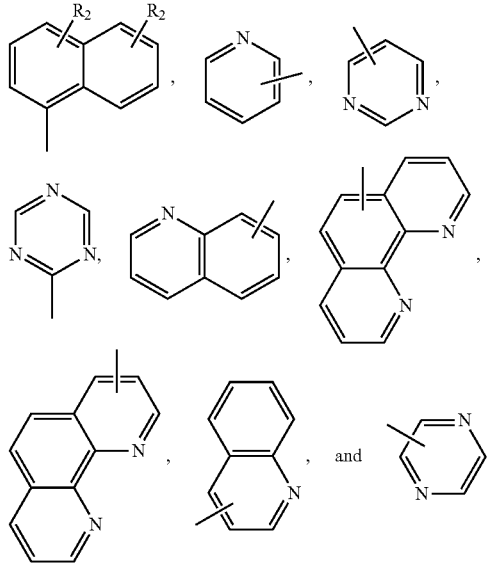

x is an integer from 1 to 10,

X is halogen (F, Cl, Br, I),

Y is selected from CH$_2$, S, O, Se and N—R$_2$,

R$_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group, In a preferred embodiment of the naphtalene diimide (NDI)-based material represented by the general formula IIIa R is, particularly, selected from

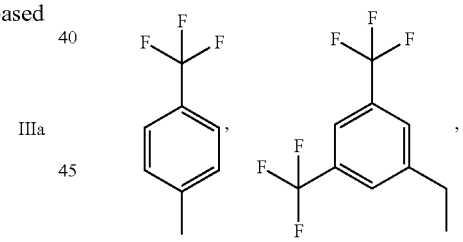

—(CF$_2$)$_5$CF$_3$, —(CH$_2$)$_5$CH$_3$, —CH$_2$—(CF$_2$)$_3$—CF$_3$,

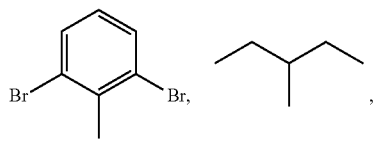

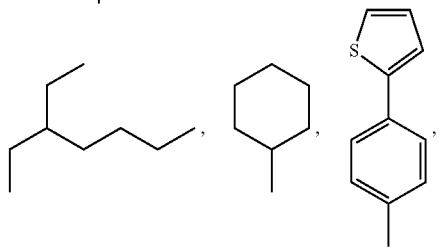

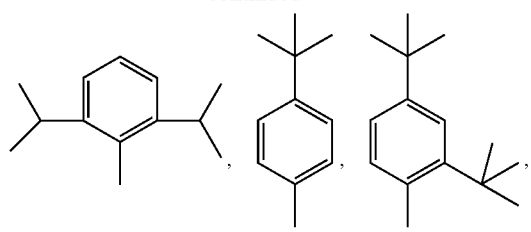
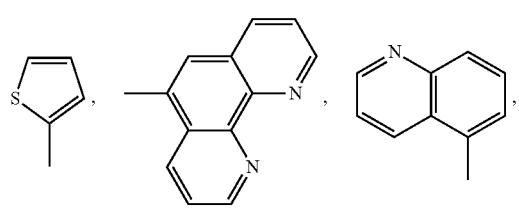
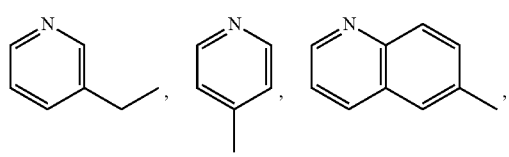
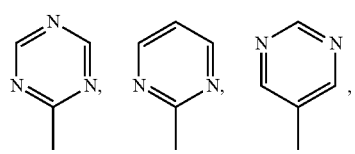
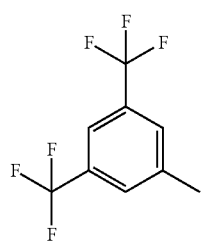 and 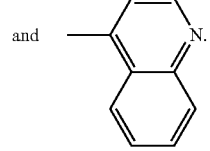
In one embodiment, the transparent N and/or P material of the present disclosure is a naphtalene diimide dimer (NDI-NDI)-based material represented by the general formula IV or V
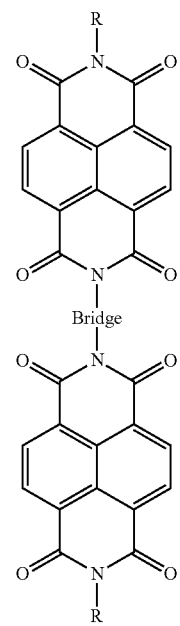
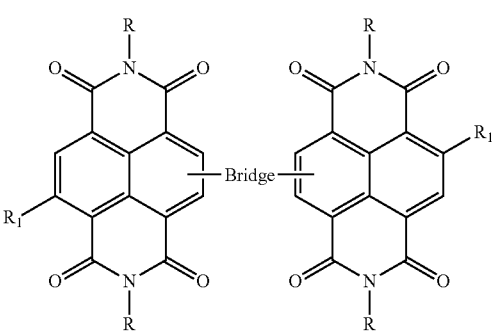
wherein in general formula IV
R is, at each occurrence, independently selected from $-C_xH_{2x+1}$, $-C_xX_{2x+1}$, $-C_xH_2X_{2x+1}$,
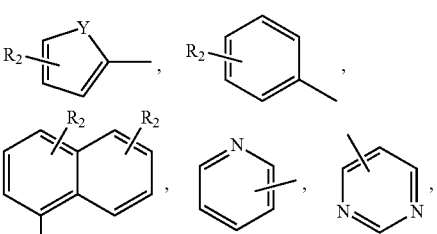
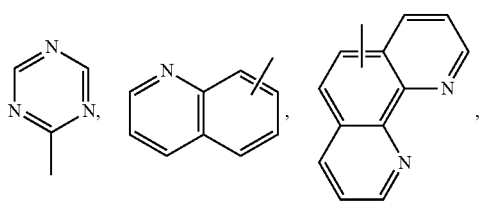

-continued

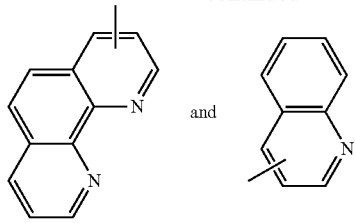
and and
Bridge is selected from

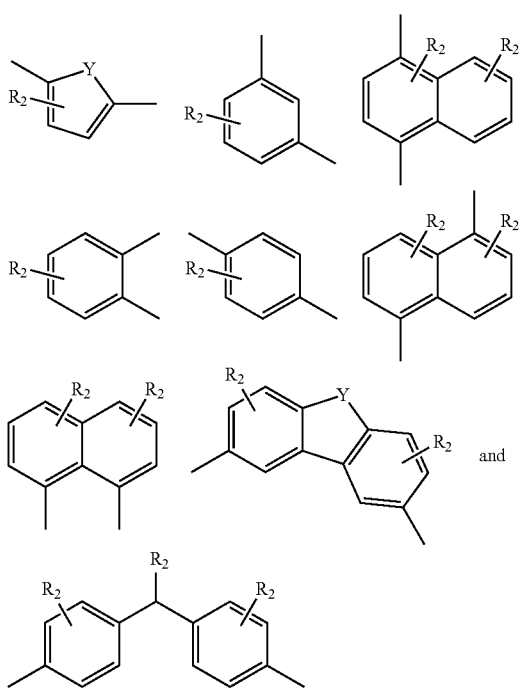

x is an integer from 1 to 10,
X is halogen (F, Cl, Br, I),
Y is selected from CH$_2$, S, O, Se and N—R$_2$,
R$_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group,
and wherein in general formula V
R is, at each occurrence, independently selected from —C$_x$H$_{2x+1}$, —C$_x$X$_{2x+1}$, —C$_x$H$_2$X$_{2x-1}$,

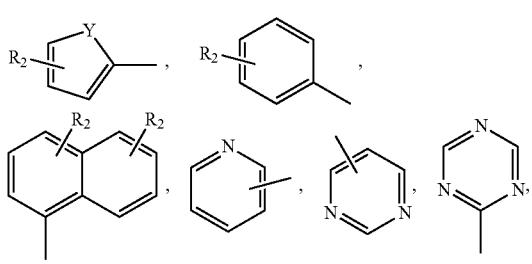

-continued

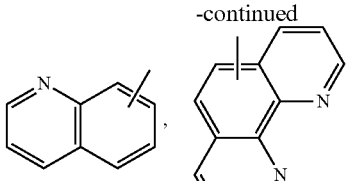
and

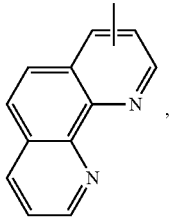

and
R$_1$ is, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated alkyl group, heteroaryl group, fluorenyl group, and
Bridge is selected from

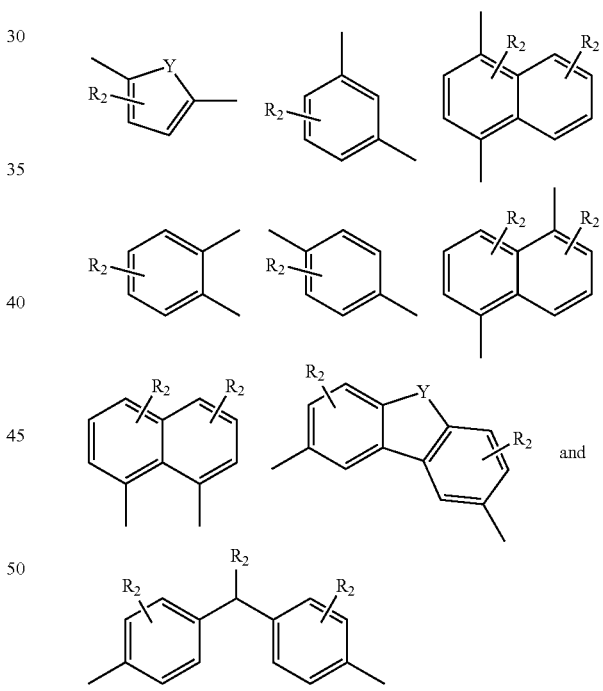

x is an integer from 1 to 10,
X is halogen (F, Cl, Br, I),
Y is selected from CH$_2$, S, O, Se and N—R$_2$,
R$_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.
In a preferred embodiment of the naphtalene diimide dimer (NDI-NDI)-based material represented by the general formula IV R is selected from
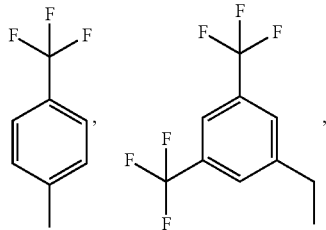
—(CF$_2$)$_5$CF$_3$, —(CH$_2$)$_5$CH$_3$, —CH$_2$—(CF$_2$)$_3$—CF$_3$,
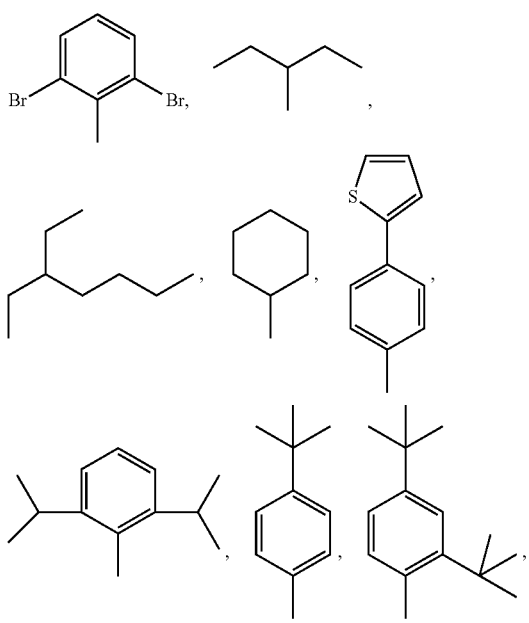
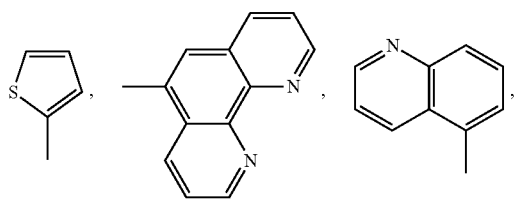
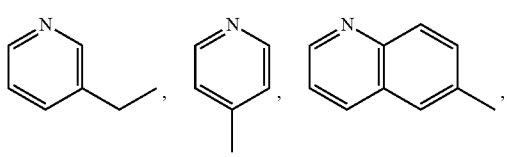
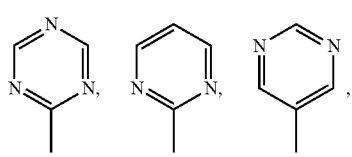
-continued
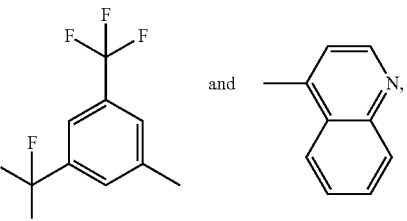
and/or
Bridge is selected from
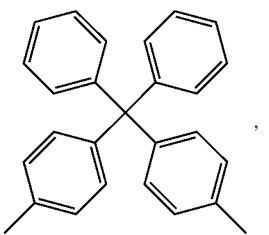
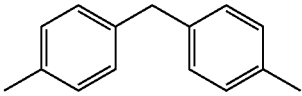
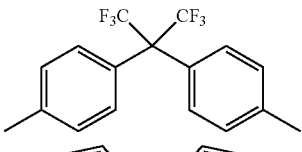
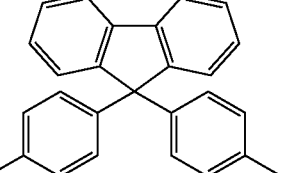
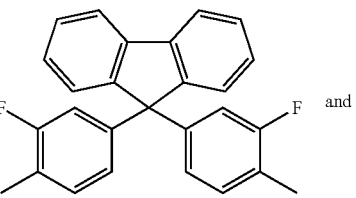
and
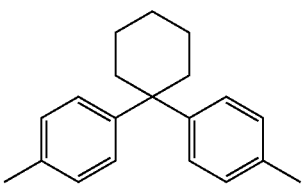
In a preferred embodiment of the naphtalene diimide dimer (NDI-NDI)-based material represented by the general formula V R is selected from
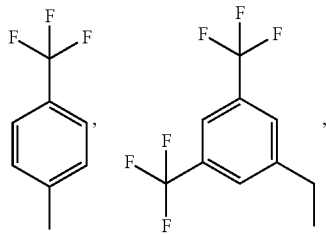
—(CF$_2$)$_5$CF$_3$, —(CH$_2$)$_5$CH$_3$, —CH$_2$—(CF$_2$)$_3$—CF$_3$,
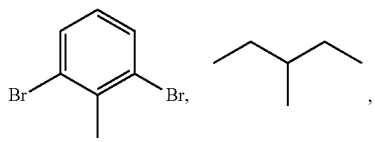
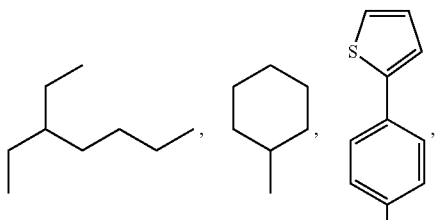
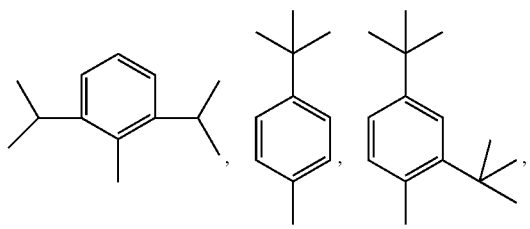
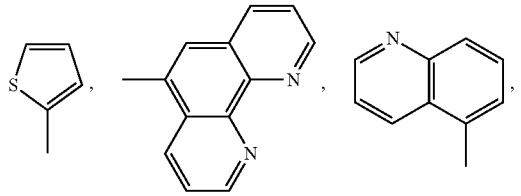
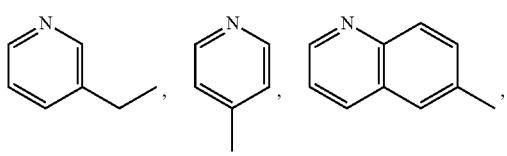
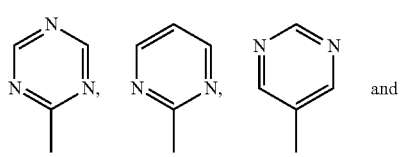
and
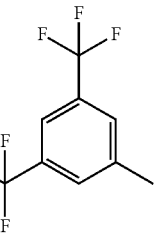
R$_1$ is selected from —Br, —H, —OCH$_2$CH$_3$,
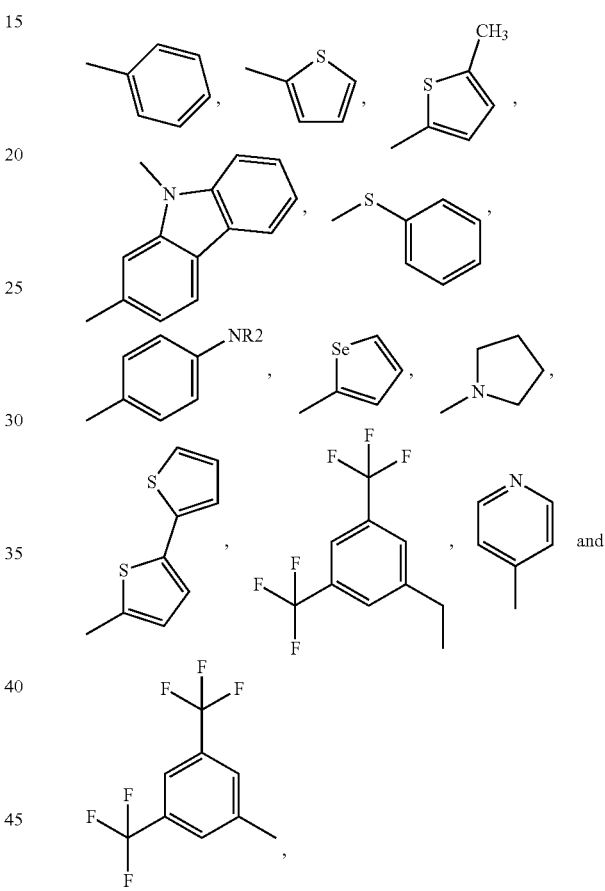
and/or
Bridge is selected from
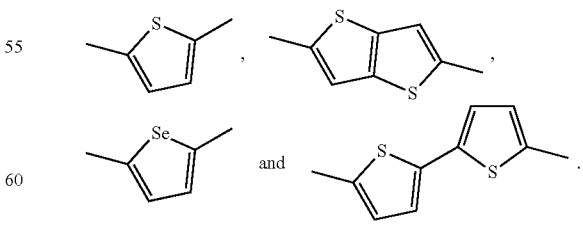
In one embodiment the transparent N and/or P material of the present disclosure is a naphtalene mono-diimide dimer (NMI-NDI)-based material represented by a general formula selected from general formulas VI to VIII

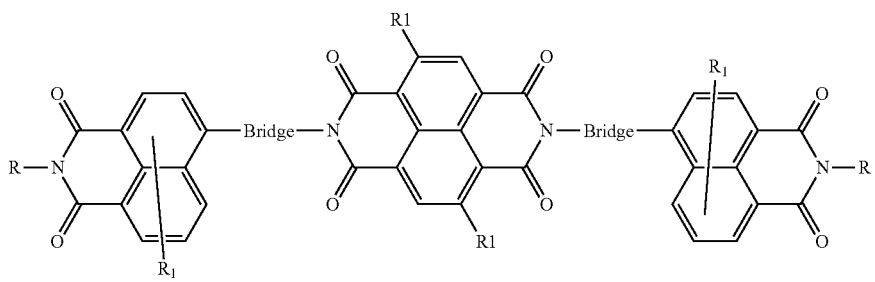
VI
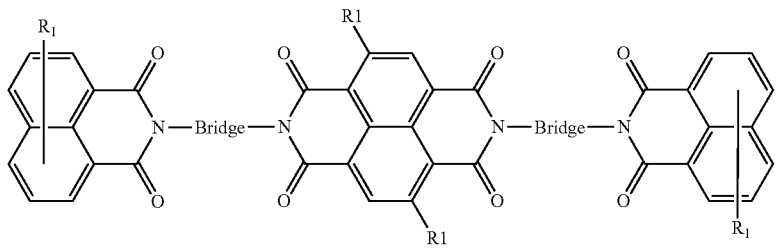
VII
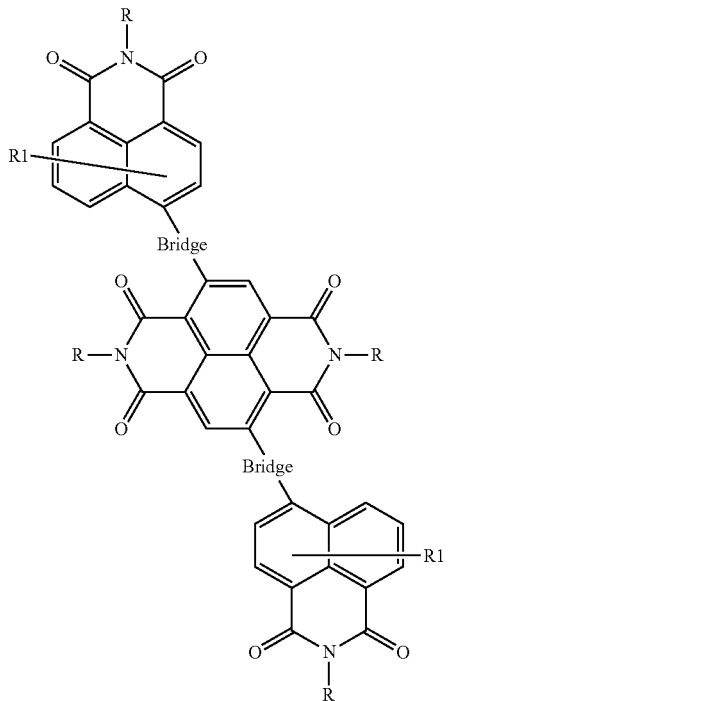
VIII
wherein
R is, at each occurrence, independently selected from $-C_xH_{2x+1}$, $-C_xX_{2x+1}$, $-C_xH_2X_{2x-1}$,
-continued
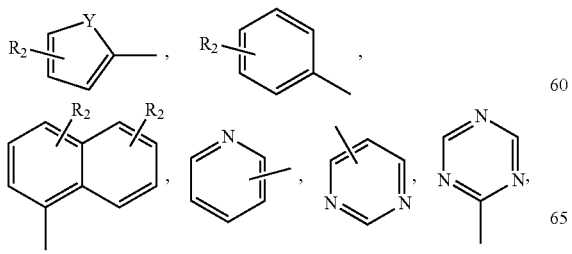
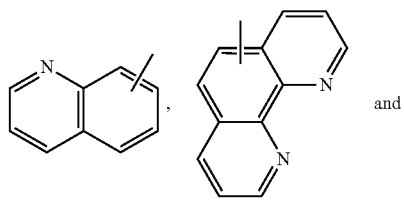
and -continued

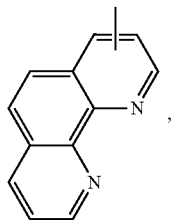

and $R_1$ is, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated alkyl group, heteroaryl group, fluorenyl group, and Bridge is selected from

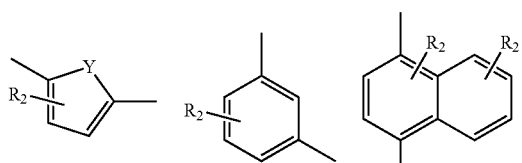

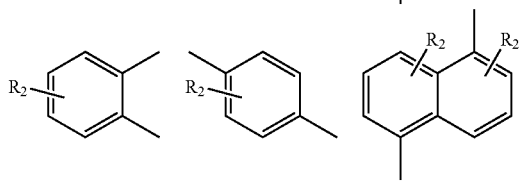

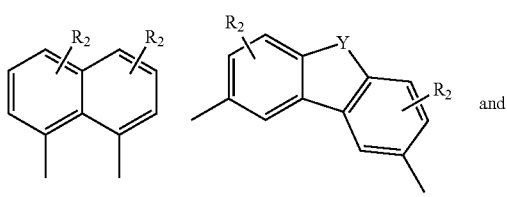

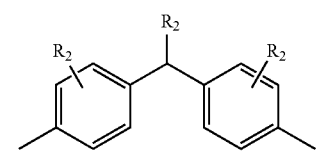

x is an integer from 1 to 10,

X is halogen (F, Cl, Br, I),

Y is selected from $CH_2$, S, O, Se and N—$R_2$, $R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

In one embodiment the transparent N and/or P material of the present disclosure is a thiophene- or selenophene-based material represented by a general formula selected from general formulas IX to XI

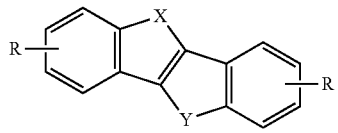

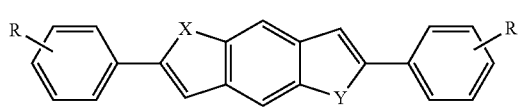

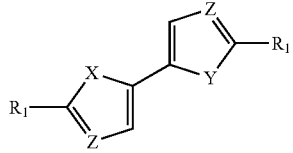

wherein
X and Y are the same or different and are, at each occurrence, independently selected from $CH_2$, S, O, Se, N—R and Si—$R_2$, Z is selected from CH and N, R and $R_1$ are the same or different and are, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group.

In a preferred embodiment of the thiophene- or selenophene-based material of general formulas IX to XI X is selected from S and Se, Y is selected from S and Se, Z is selected from CH and N, R is selected from

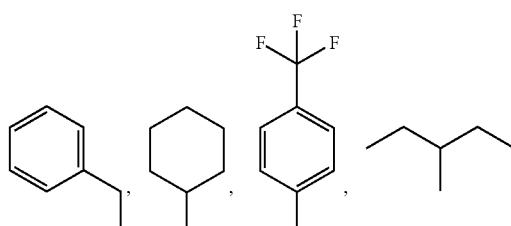

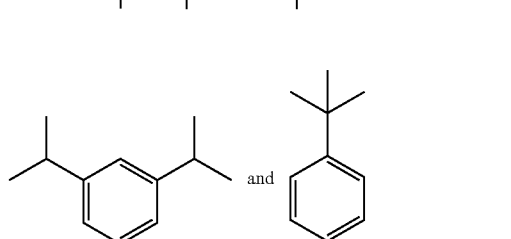

and/or

R₁ is selected from

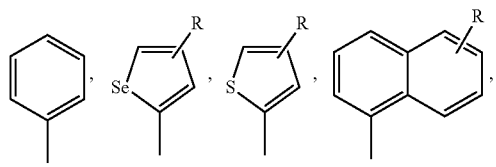

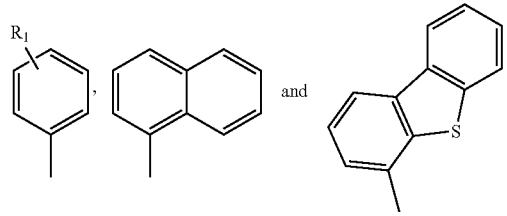

In one embodiment the transparent N and/or P material of the present disclosure is a thiophene- or selenophene-based material represented by the general formula XII or XIIb

XII

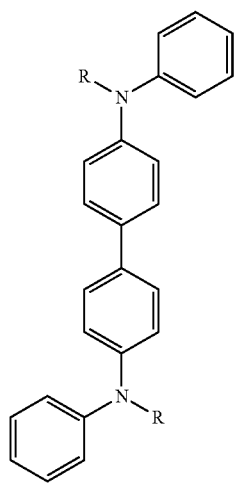

XIIb

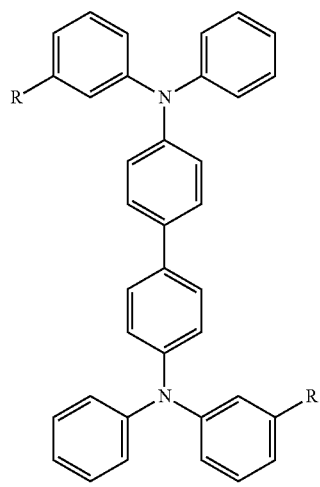

wherein

R is, at each occurrence, independently selected from

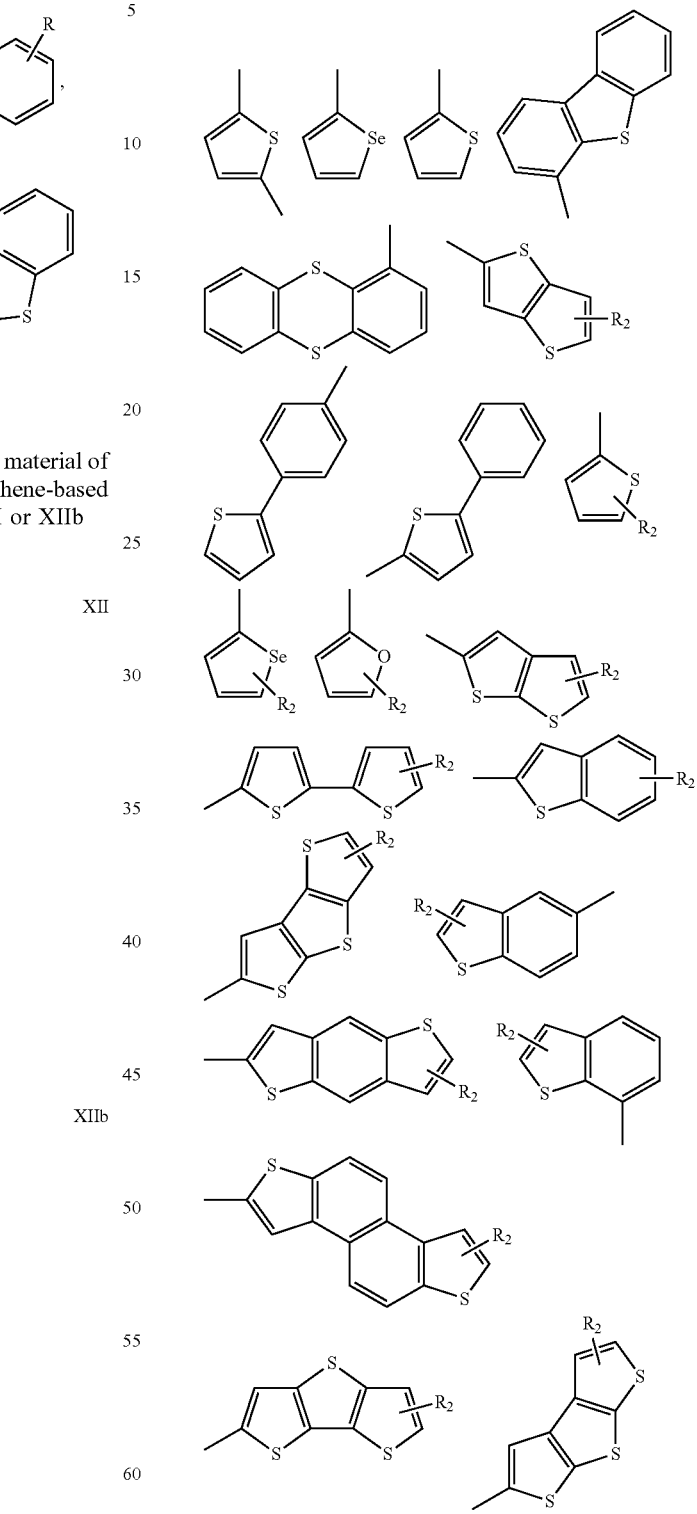

In one embodiment the transparent N and/or P material of the present disclosure is a thiophene- or selenophene-based material represented by the general formulas XXII to XXXVIII:

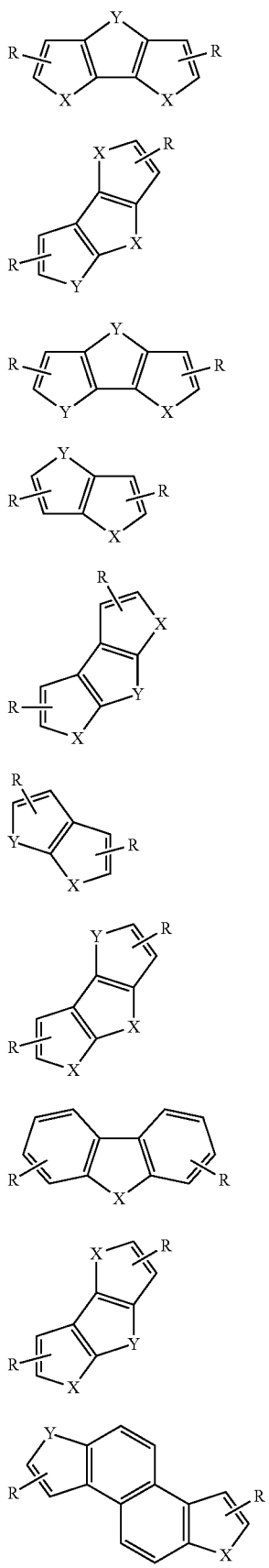
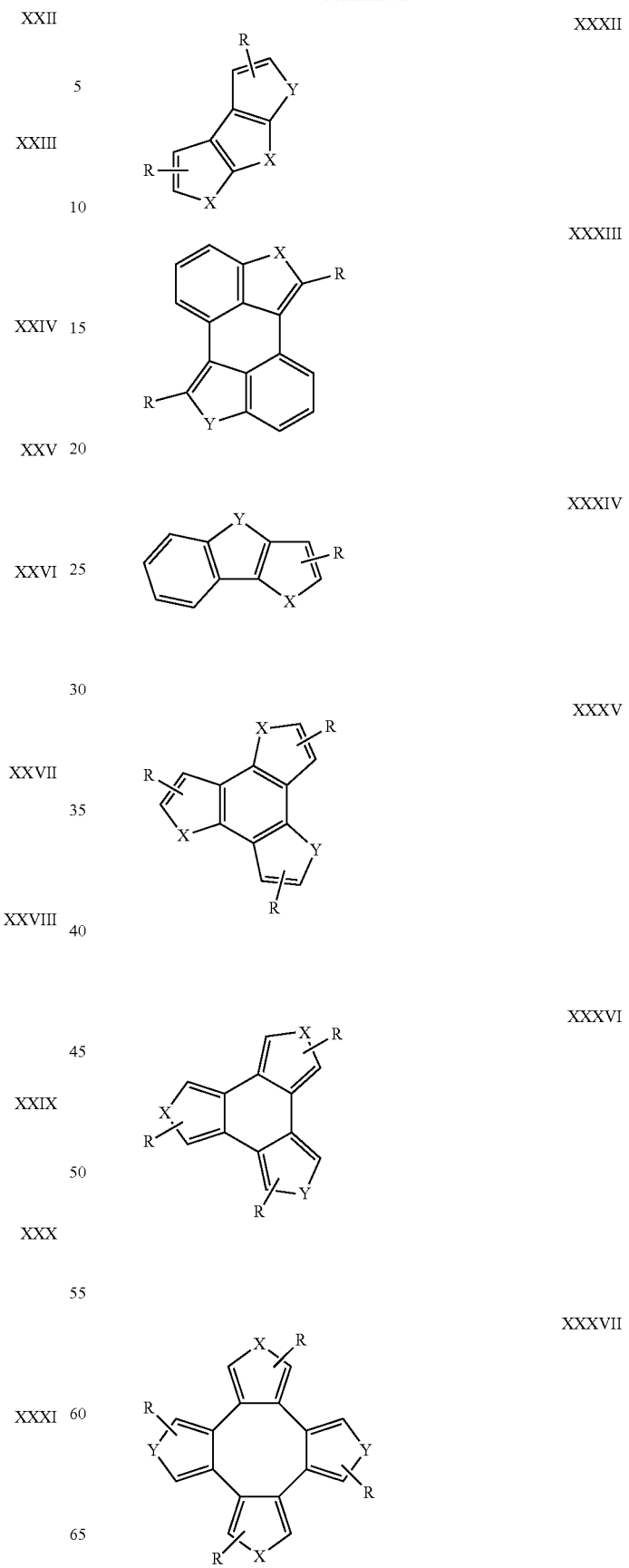

-continued

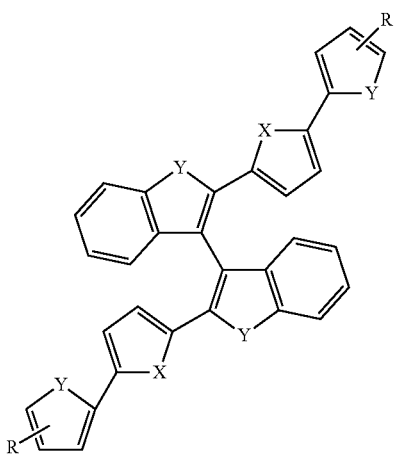

XXXVIII wherein
X and Y are the same or different and are, at each occurrence, independently selected from $CH_2$, S, O, Se, N—R and Si—$R_2$,
Z is selected from CH and N,
R and $R_1$ are the same or different and are, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group, In a preferred embodiment of the thiophene- or selenophene-based material of general formulas XXII to XXXVIII
X is selected from S and Se,
Y is selected from S and Se,
Z is selected from CH and N,
R is selected from

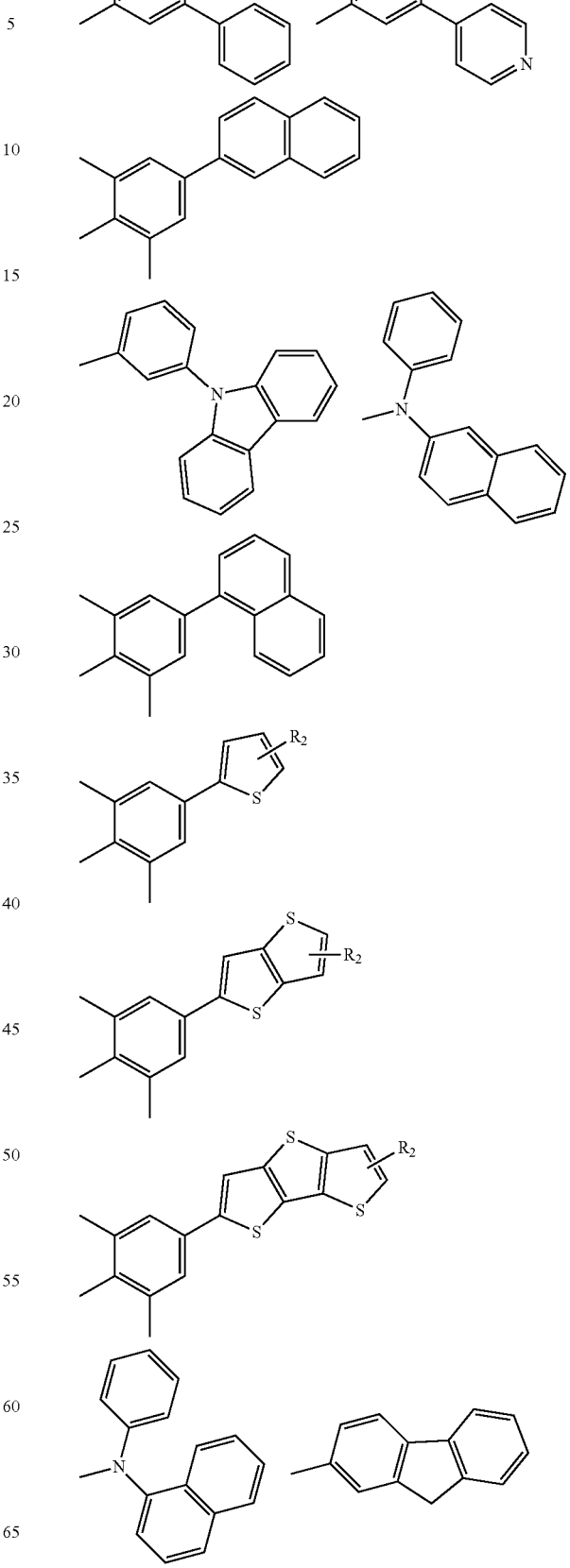

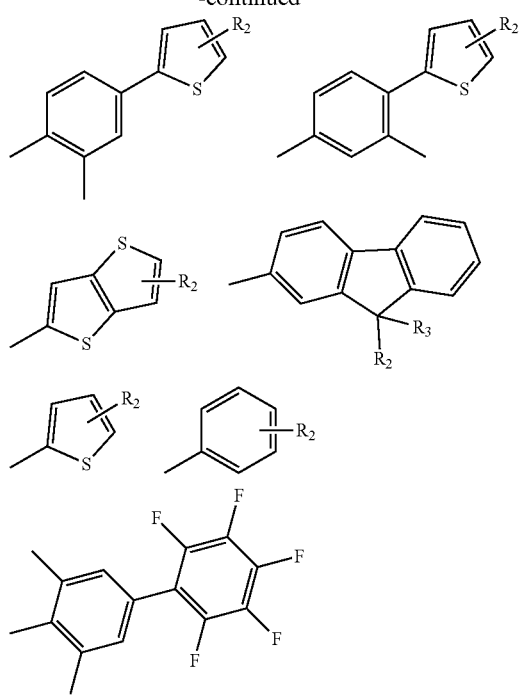

wherein $R_2$ and $R_3$ are the same or different and are, at each occurrence, independently selected from H, $CH_3$, alkyl, aryl.

In one embodiment the transparent N and/or P material of the present disclosure is a thiophene- or selenophene-based material represented by the general formula XXXIX or XL:

T-B-T            XXXIX wherein
T is selected from a structure with one of the general formulas IX, X, XI or XXII to XXXVIII, as defined herein,
with
X and Y being the same or different and being, at each occurrence, independently selected from $CH_2$, S, O, Se, N—R and Si—$R_2$,
Z being selected from CH and N,
B is selected from any one of

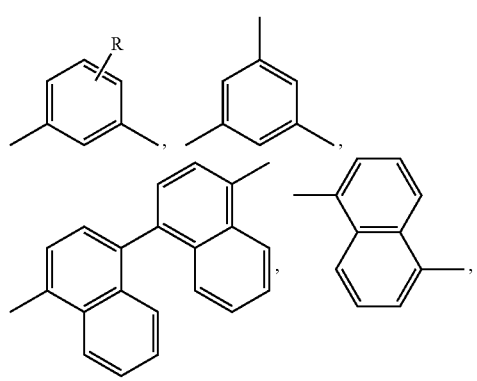

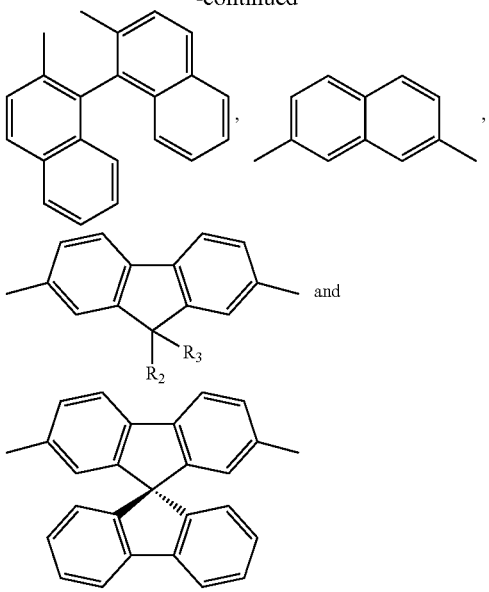

with $R_2$ and $R_3$ being the same or different and are, at each occurrence, independently selected from H, $CH_3$, alkyl, aryl.
R is at each occurrence, independently selected from H, alkyl, aryl,

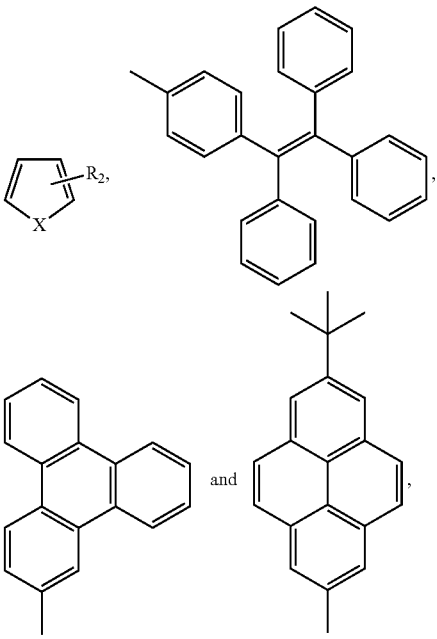

T-H            XL wherein
T is selected from a structure with one of the general formulas IX, X, XI or XXII to XXXVIII, as defined herein,
with
X and Y being the same or different and being, at each occurrence, independently selected from $CH_2$, S, O, Se, N—R and
Z being selected from CH and N, H is selected from any one of

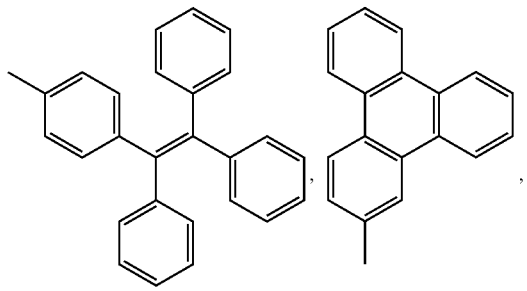

In one embodiment the transparent N and/or P material of the present disclosure is a dithienopyrrol (DTP)-based material represented by the general formula XIII

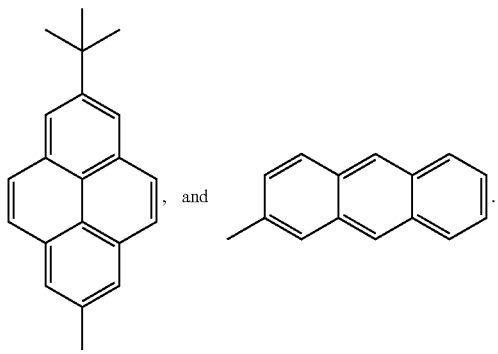 XIII wherein
R is selected from —$C_xH_{2x+1}$, —$C_xX_{2x+1}$, —$C_xH_2X_{2x-1}$,

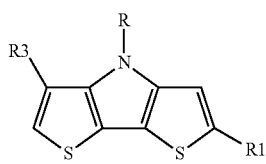

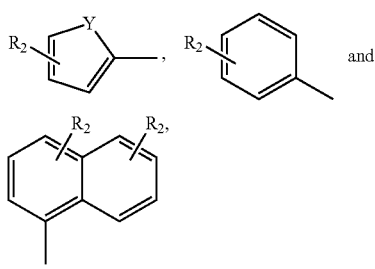

$R_1$ is selected from

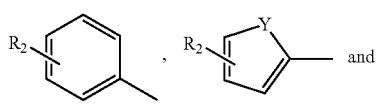

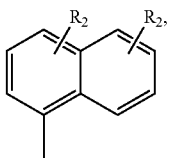

$R_3$ is selected from linear and branched alkyl group, cycloalkyl group, halogenated alkyl group, halogen atoms,
x is an integer from 1 to 10,
X is halogen (F, Cl, Br, I),
Y is selected from $CH_2$, S, O, Se and N—$R_2$,
$R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

In a preferred embodiment of the dithienopyrrol (DTP)-based material represented by the general formula XIII
R is selected from

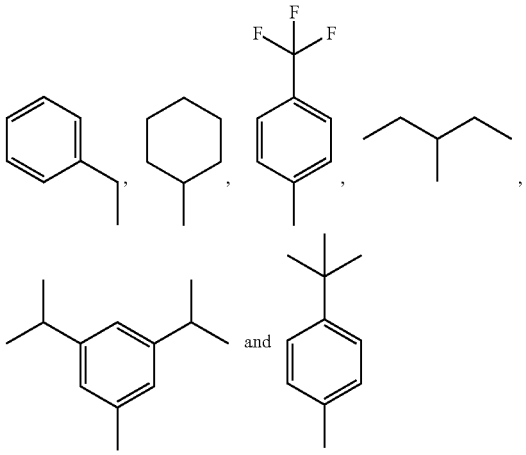

$R_1$ is selected from

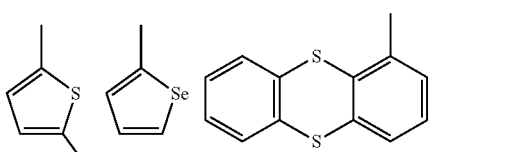

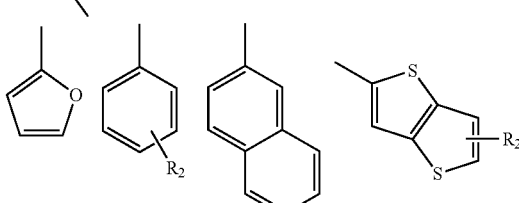

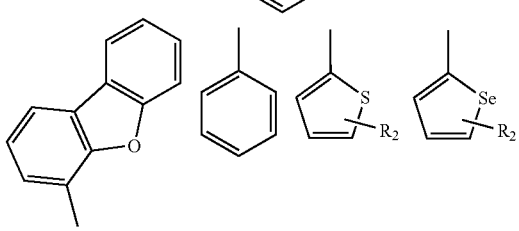

-continued

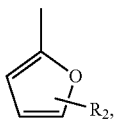

and/or
R₂ is selected from linear and branched alkyl group.

In one embodiment the transparent N and/or P material of the present disclosure is a dithienopyrrol dimer (DTP dimer)-based material represented by a general formula selected from general formulas XIV to XVI

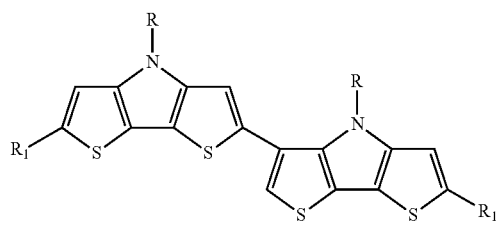
XIV

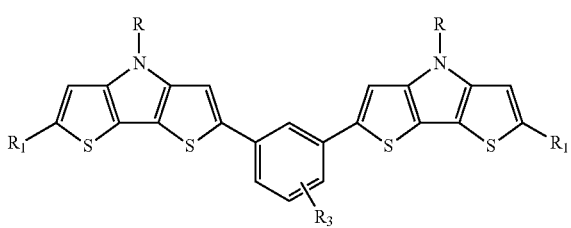
XV

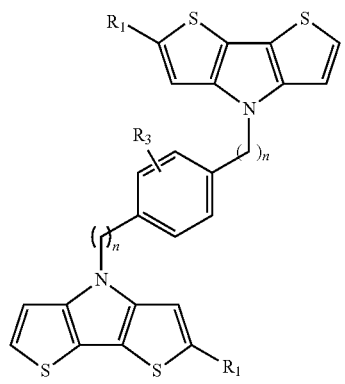
XVI wherein
R is, at each occurrence, independently selected from selected from —$C_xH_{2x+1}$, —$C_xX_{2x+1}$, —$C_xH_2X_{2x-1}$,

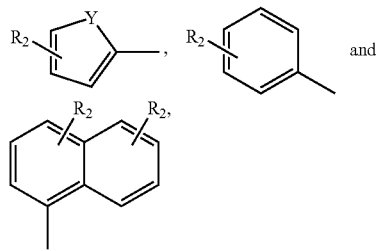
and $R_1$ is, at each occurrence, independently selected from

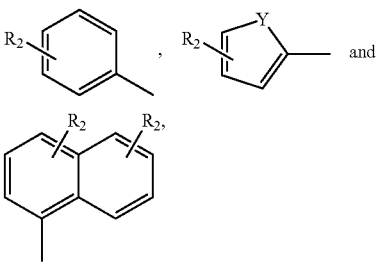
and $R_3$ is selected from linear and branched alkyl group, cycloalkyl group, halogenated alkyl group, halogen atoms, n is 0 or 1, x is an integer from 1 to 10, X is halogen (F, Cl, Br, I), Y is selected from $CH_2$, S, O, Se and N—$R_2$, $R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

In a preferred embodiment of the dithienopyrrol dimer (DTP dimer)-based material represented by general formulas XIV to XVI R is selected from

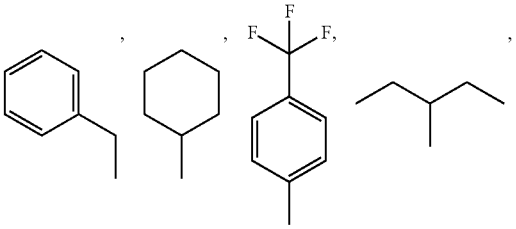

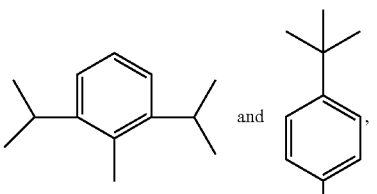

$R_1$ is selected from

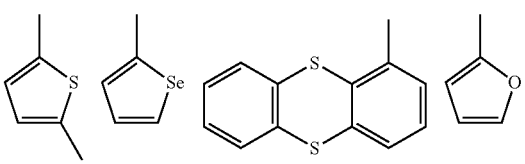

-continued

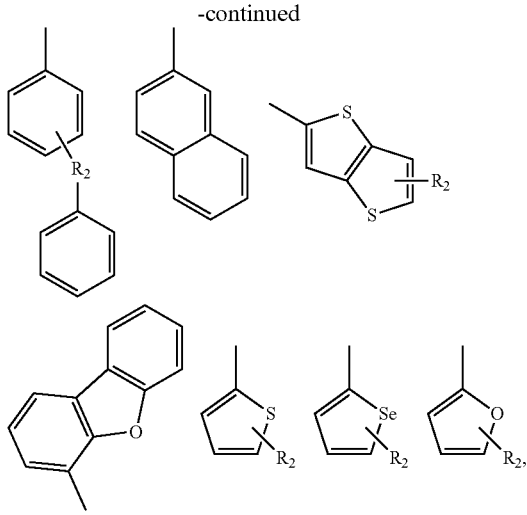

and/or

R$_2$ is selected from linear and branched alkyl group.

In one embodiment the transparent N and/or P material of the present disclosure is an anthracene- or anthracene dimer-based material represented by the general formula XVII or XVIII

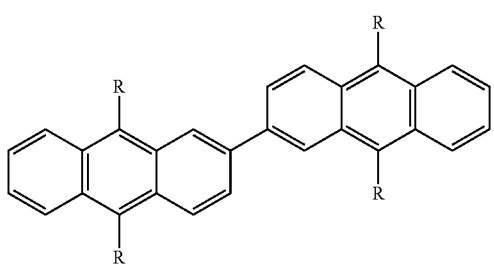
XVII

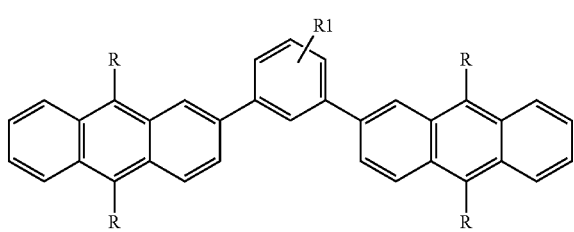
XVIII wherein
R is, at each occurrence, independently selected from

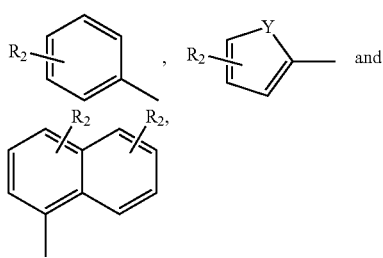

R$_1$ is selected from linear and branched alkyl group, cycloalkyl group, halogenated alkyl group, halogen atoms, Y is selected from CH$_2$, S, O, Se and N—R$_2$, R$_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

In a preferred embodiment of the anthracene- or anthracene dimer-based material represented by the general formula XVII or XVIII R is selected from

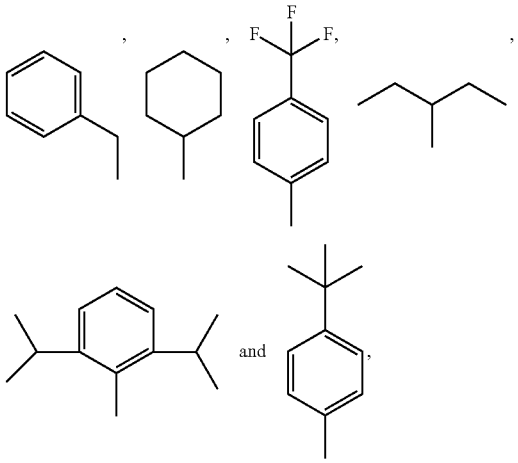

and/or

R$_1$ is selected from linear and branched alkyl group.

In one embodiment the transparent N and/or P material of the present disclosure is a zinc coordination complex-based material.

The zinc complexes are characterized by the presence of Zn—N bonds or a combination of Zn—N and Zn—O bonds, where the N and O atoms are elements of the organic ligands, and the absence of Zn—C bonds. The zinc coordination complexes or zinc coordination complex-based materials are represented by a general formula selected from general formulas XIX to XXI

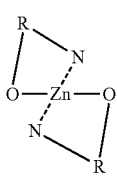
XIX

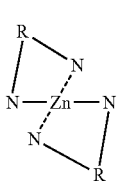
XX

XXI

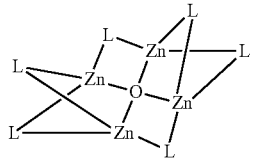

wherein

ORN is, at each occurrence, independently selected from

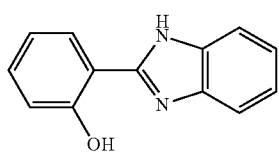

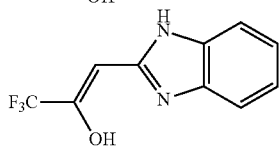

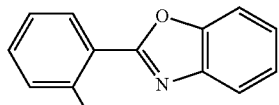

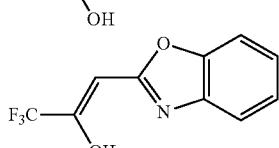

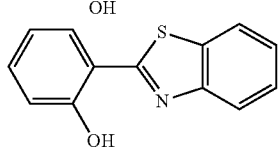

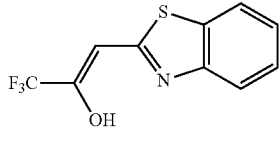

NRN is, at each occurrence, independently selected from

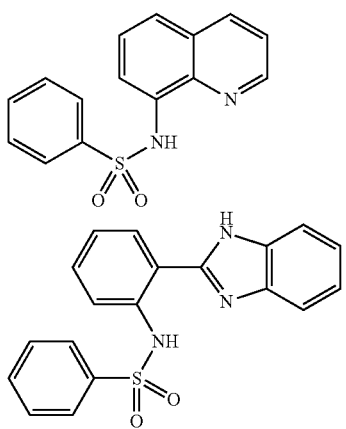

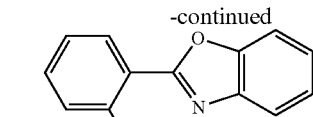

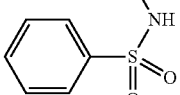

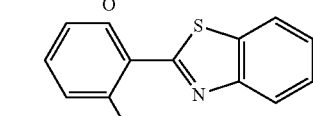

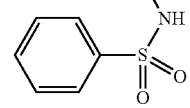

L is, at each occurrence, independently selected from

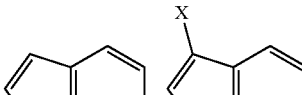 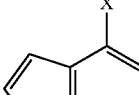

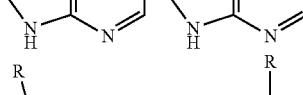 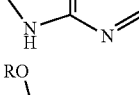

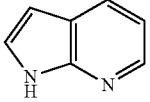

X is selected from halogen (F, Cl, Br, I), CN, $CF_3$, COOH, $NH_2$,

R is selected from alkyl and aryl.

As discussed above, the present disclosure provides a P:N heterojunction, preferably a P1:P2:N1:N2 heterojunction, including a transparent N material according to the present disclosure and/or a transparent P material according to the present disclosure.

In one embodiment, a transparent P material according to the present disclosure is the donor and a transparent N material according to the present disclosure is the acceptor in a P:N heterojunction. See, for example, FIG. 4.

In one embodiment of a P1:P2:N1:N2 heterojunction, one of the P materials could be a transparent P material according to the present disclosure and a donor, as well as one of the N materials could be a transparent N material according to the present disclosure and an acceptor.

In one embodiment, the P:N heterojunction, preferably the P1:P2:N1:N2 heterojunction includes a further N and/or P material, wherein the further N and/or P material preferably exhibits absorption in the visible wavelength range (about 400 to about 700 nm).

As discussed above, the present disclosure provides the use of a transparent N and/or P material according to the present disclosure in an absorption layer.

In one embodiment, the absorption layer includes a further N and/or P material, wherein the further N and/or P material preferably exhibits absorption in the visible wavelength range (about 400 to about 700 nm).

As discussed above, the present disclosure provides the use of a transparent N and/or P material according to the present disclosure
in a photoelectric conversion layer, and/or
in an organic and/or hybrid module
for optoelectronic application, such as image sensor, photodiode, organic photovoltaics, including organic photoelectric conversion layer(s), OLED and OTFT organic modules, In one embodiment, the photoelectric conversion layer and/or the organic and/or hybrid module includes a further N and/or P material,
wherein the further N and/or P material preferably exhibits absorption in the visible wavelength range (about 400 to about 700 nm).

As discussed above, the present disclosure provides a photoelectric conversion layer including a transparent N and/or P material according to the present disclosure.

In one embodiment, the photoelectric conversion layer includes a further N and/or P material, wherein the further N and/or P material preferably exhibits absorption in the visible wavelength range (about 400 to about 700 nm).

In one embodiment, the photoelectric conversion layer includes further molecule(s).

As discussed above, the present disclosure provides an absorption layer including a transparent N and/or P material according to the present disclosure.

In one embodiment, the absorption layer includes a further N and/or P material, wherein the further N and/or P material preferably exhibits absorption in the visible wavelength range (about 400 to about 700 nm).

In one embodiment, the absorption layer includes further molecule(s).

As discussed above, the present disclosure provides a device, including transparent N and/or P material(s) according to the present disclosure or photoelectric conversion layer(s) according to the present disclosure,
Said device can be an organic image sensor, a hybrid image sensor, photodiode, organic photovoltaics, organic light-emitting diode (OLED), organic thin-film transistor (OTFT).

In one embodiment, said photoelectric conversion layer exhibits photo response in the visible absorption range.

In this embodiment, the photoelectric conversion layer of the device includes the transparent N and/or P material(s) according to the present disclosure and further N and/or P material(s), preferably exhibiting absorption in the visible wavelength range (about 400 to about 700 nm).

According to the present disclosure, when one of the active materials is transparent offers the following possibilities:
Tuning overall absorption spectrum via tuning absorption of one active material only;
Tuning of exciton diffusion efficiencies of the partner (absorbing) material only;
Tuning of charge generation efficiencies through HOMO or LUMO independently;
Tuning of only electron (for transparent n) or only hole (transparent p) mobility;
Generally: decoupling of absorption properties in the visible range from electron/hole transfer and transport properties.

In one embodiment, photoelectric conversion layer of the device includes further molecule(s).

The photoelectric conversion layer can include different components (dyes) and combinations thereof.

In one embodiment, the photoelectric conversion layer and/or the absorption layer includes further n and p type materials (molecules) and their derivatives that can be used together with the material(s) of the present disclosure, such as phthalocyanines (Pc), subphthalocyanines (SubPc), merocyanines (MC), diketopyrrolopyrroles (DPP), borondipyrromethenes (BODIPY), isoindigo (ID), perylene diimides (PDI) and perylene monoimides (PMI), and quinacridones (QD), fused acenes, such as pentacene and tetracene and triphenylamine and its derivatives (TPAs) as donor; and/or fullerenes, rylene diimides and monoimides (e.g. PDI and PMIs but not limited to), phthalocyanines and subphthalocyanines, borondipyrromethenes (BODIPY) and cyanopentacenes as acceptor.

As discussed above, the present disclosure provides an organic image sensor, including photoelectric conversion layer(s) according to the present disclosure.

The organic image sensor of the present disclosure preferably includes
(a) an organic photoelectric conversion unit including photoelectric conversion layer(s) according to the present disclosure,
(b) at least one electrode,
(c) a substrate,
(d) optionally, a second electrode on top of said photoelectric conversion layer(s).

The substrate can be silicon, quartz, glass, polymer, such as PMMA, PC, PS, COP, COP, PVA, PVP, PES, PET, PEN, mica, or combinations thereof.

The substrate can also be other photoelectric conversion unit(s).

This means, a device of this disclosure can include (i) two inorganic units with one organic unit, (ii) one inorganic unit with two organic units, or (iii) three organic units combined with each other in the organic image sensor. Any of the organic units can contain molecules/layers/devices according to this disclosure.

In a preferred embodiment, an organic image sensor consists of three organic conversion units containing molecules in layers as of this disclosure (in devices, each with transparent electrodes), combined with each other and operating each in one of the ranges 400 nm to 500 nm, 500 nm to 600 nm and 600 nm to 700 nm.

Combined units can be realized either by vertical and/or horizontal stacking of the organic-organic or organic-inorganic units.

The electrode material can be
transparent metal oxide, such as indium tin oxide (ITO), fluorine-doped indium oxide (IFO), tin oxide, fluorine-doped tin oxide (FTO), antimonium-doped tin oxide (ATO), zinc oxide (including Al, B and Ga doped zinc Oxide), indium oxide-zinc oxide (IZO), $TiO_2$,
non transparent or semitransparent metal or alloy or conductive polymer, such as Au, Ag, Cr, Ni, Pd, AlSiCu, or any metal or metal alloy or metal combination with suitable workfunction; PEDOT/PSS, PANI or PANI/PSS, graphene.

As discussed above, the present disclosure provides a hybrid Silicon-organic image sensor or organic image sensor, including
(a) an organic photoelectric conversion unit or units including photoelectric conversion layer(s) according to the present disclosure,
(b) optionally, a Si based photoelectric conversion unit,
(c) metal wiring,
(d) a (CMOS) substrate,
(e) insulating layer(s), preferably oxide.

In one embodiment, said organic photoelectric conversion unit of the image sensors of the present disclosure includes different layers within the organic based photoelectrical conversion unit(s), such as n-type material,
p-type material,
n-buffer layer,
p-buffer layer, or combinations and/or mixtures (e.g. n material and p material co-deposited in one layer) thereof.

For example, the organic image sensor of the present disclosure can have the structure:

substrate/first electrode/n-buffer layer/n-material/p-material/p buffer layer/second electrode;
substrate/first electrode/n-buffer layer/n-material/mixture of n- and p-material/p-material/p buffer layer/second electrode;
substrate/first electrode/n-buffer layer/n-material/mixture of n- and p-material/p buffer layer/second electrode;
substrate/first electrode/p-buffer layer/p-material/n-material/n buffer layer/second electrode.
substrate/first electrode/p-buffer layer/p-material/mixture of n- and p-material/n-material/n buffer layer/second electrode.
substrate/first electrode/p-buffer layer/p-material/mixture of n- and p-material/n buffer layer/second electrode.

The organic image sensor of the present disclosure can include different layer structures, in particular regarding the position of the n and p material with respect to the CMOS part.

The organic photoconversion unit can be used in combination with a Si based photoelectrical conversion unit where different layers absorb different color (BGR) in a hybrid silicon-organic image sensor (see FIG. 2) or can be used without Si based photoelectrical conversion unit. In this case the organic photoconversion unit has the capability of absorbing different color (BGR) (see FIG. 3).

The BGR ranges are 400-500 nm, 500-600 nm and 600-700 nm and the absorption outside of the range is preferably less than 20%, more preferably less than 10 and 5%.

As discussed above, the substrate can also be other photoelectric conversion unit(s).

As discussed above, a device of this disclosure can include (i) two inorganic units with one organic unit, (ii) one inorganic unit with two organic units, or (iii) three organic units combined with each other in the organic image sensor. Any of the organic units can contain molecules/layers/devices according to this disclosure.

The deposition methods to produce the organic photoelectrical conversion layer are PVD, CVD, spin coating, dipping coating, casting process, inkjet printing, screen printing, spray coating, offset printing.

Different process temperatures for processing the layer are possible, namely from 50 to 245° Celsius. The processing (annealing) of the layers can be done before and/or after the deposition of the top electrode.

As discussed above, the present disclosure provides a method for synthesis of a naphtalene monoimide (NMI)-based materials (represented by the general formula I) and naphtalene monoimide dimer (NMI-NMI)-based materials (represented by the general formula II), including the step(s) of imidization of 4-Bromo-1,8-naphthalic anhydride derivatives in the presence of a primary amine and acid,
followed by the palladium catalyzed Suzuki Coupling with the specific boronic ester or "bridge"—boronic ester.

The present disclosure provides also a method for synthesis of a naphtalene diimide (NDI)-based materials (represented by the general formula III), including the steps of:

imidization of 2,6-dibromonaphthalene-1,4,5,8-tetracarboxylic dianhydride derivatives in the presence of a R-primary amine and acid,
followed by the palladium catalyzed Suzuki Coupling with the specific R1-boronic ester.

The present disclosure provides also a method for synthesis of a naphtalene diimide dimer (NDI-NDI)-based material (represented by the general formula IV or V) including (i) in the case of general formula IV the steps of mono imidization of 2,6-dibromonaphthalene-1,4,5,8-tetracarboxylic dianhydride derivatives in the presence of a R-primary amine and acid,
followed by a second imidization in the presence of a "Bridge"-diamine and acid, and (ii) in the case of general formula V, the steps of
imidization of 2,6-dibromonaphthalene-1,4,5,8-tetracarboxylic dianhydride derivatives in the presence of a R-primary amine and acid,
followed by a mono palladium catalyzed Suzuki Coupling with the specific R1-boronic ester,
followed by a second palladium catalyzed Suzuki Coupling with the specific Bridge-diboronic ester.

The present disclosure provides also a method for synthesis of a naphtalene mono-diimide dimer (NMI-NDI)-based material (represented by a general formula selected from general formulas VI to VIII) including the steps of imidization of corresponding 2,6-dibromonaphthalene-1,4,5,8-tetracarboxylic dianhydride with the appropriate amine derivatives,
followed by one or several palladium catalyzed Suzuki Coupling with the specific diboronic ester.

The present disclosure provides also a method for synthesis of dithienopyrrol dimer (DTP dimer)-based materials (represented by a general formula selected from general formulas XIV and XV) including the steps of palladium catalyzed Buchwald-Hartwig coupling of 3,3'-dibromo-2,2'-bithiophene with the corresponding R-amine to receive the N-substituted dithienopyrrole (DTP) core unit.

Further steps include
bromination with N-bromo-succinimide,
followed by mono-palladium catalyzed Suzuki Coupling with R1-boronic ester, and
followed by a further palladium catalyzed Suzuki Coupling with the specific R2-phenylsubstituted di boronic ester.

The present disclosure provides also a method for synthesis of dithienopyrrol dimer (DTP dimer)-based material (represented by a general formula XVI) including the steps of palladium catalyzed Buchwald-Hartwig coupling of 3,3'-dibromo-2,2'-bithiophene with the corresponding R2-phenylsubstituted diamine to receive the N-substituted dithienopyrrole (DTP) dimer core unit.

Further steps include
bromination with N-bromo-succinimide,
followed by mono-palladium catalyzed Suzuki Coupling with R1-boronic ester, and
followed by a further palladium catalyzed Suzuki Coupling with the specific R2-phenylsubstituted di boronic ester.

The present disclosure provides also a method for synthesis of zinc coordination complex-based materials (represented by a general formula selected from general formulas XIX, XX and XI) including the steps of
combining ligands of the type (HO—RN) and (HN—RN) with zinc acetate dehydrate and a base in refluxing methanol.

Note that the present technology can also be configured as described below.

(1) A transparent N material,
which has the quality when included in a P:N heterojunction or bilayer or multilayer junction, preferably a P1:P2:N1:N2 or P1:P2:N or P:N1:N2 heterojunction or multilayer junction, to dissociate efficiently the excitons created on colored P or a mixture of colored P materials (P1:P2) or of another colored N or mixture of colored N and P materials (P:N2 or P1:P2:N2) via a process of LUMO dissociation,
wherein transparent refers to an absorption coefficient of less than about 60,000 cm$^{-1}$ in the visible wavelength range (about 400 to about 700 nm), or to an extinction coefficient of less than about 60,000 M$^{-1}$ cm$^{-1}$ (in toluene),
and colored refers to an absorption coefficient of more than about 60,000 cm$^{-1}$ in the visible wavelength range in the region from about 400 nm to about 700 nm (with maxima anywhere in this region or absorbing everywhere in this region).

(2) A transparent P material,
which has the quality when included in a P:N heterojunction or P:N bilayer or multilayer junction, preferably a P1:P2:N1:N2 or a P1:P2:N1 or a P:N1:N2 heterojunction or multilayer junction, to dissociate efficiently the excitons created on colored N or a mixture of colored N materials (N1:N2) materials or of another colored P or mixture of colored P and N materials (P2:N or P2:N1:N2)
via a process of HOMO dissociation,
wherein transparent refers to an absorption coefficient of less than about 60,000 cm$^{-1}$ in the visible wavelength range (about 400 to about 700 nm), or to an extinction coefficient of less than about 60,000M$^{-1}$ cm$^{-1}$ (in toluene),
and colored refers to an absorption coefficient of more than about 60,000 cm$^{-1}$ in the visible wavelength range in the region from about 400 nm to about 700 nm (with maxima anywhere in this region or absorbing everywhere in this region).

(3) The transparent N or P material of (1) or (2), wherein the material
has an absorption coefficient of less than about 60,000 cm$^{-1}$ in the visible wavelength range (about 400 to about 700 nm), or an extinction coefficient of less than about 60,000 M$^{-1}$ cm$^{-1}$ (in toluene),
is an organic based compound forming high quality homogenous films when using deposition methods (such as vacuum deposition or spincoating).

(4) The transparent N or P material of any one of (1) to (3) which is selected from the group of
naphtalene monoimides (NMI),
naphtalene dimides (NDI),
dimers of naphtalene monoimides and/or naphtalene dimides (NMI-NMI, NDI-NDI or NMI-NDI),
thiophene- or selenophene-based materials,
dithienopyrrol (DTP)-based and DTP-dimer materials,
anthracene-based materials, and
zinc coordination complexes.

(5) The transparent N or P material of (4), wherein the material is a naphtalene monoimide (NMI)-based material represented by the general formula I

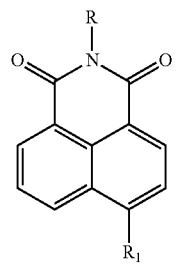

wherein
R is selected from —C$_x$H$_{2x+1}$, —C$_x$H$_{2x+1}$, —C$_x$H$_2$H$_{2x-1}$,

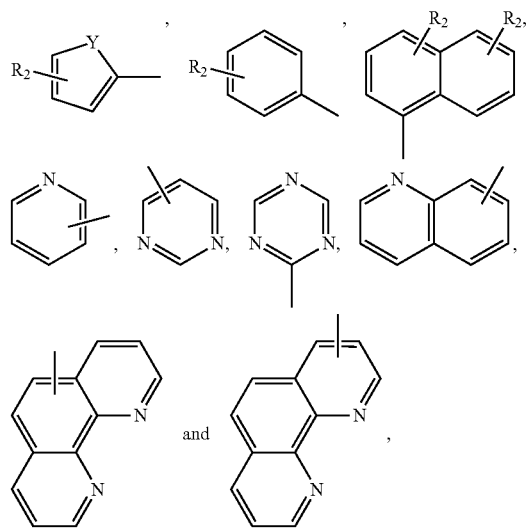

and
R$_1$ is selected from

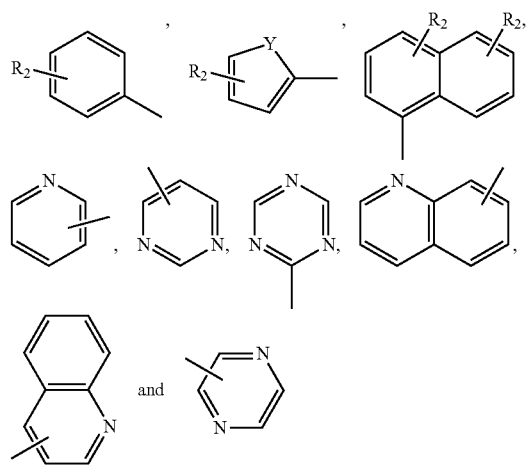

x is an integer from 1 to 10,
X is halogen (F, Cl, Br, I),
Y is selected from CH$_2$, S, O, Se and N—R$_2$,
R$_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group,
wherein preferably
R is, preferably, selected from
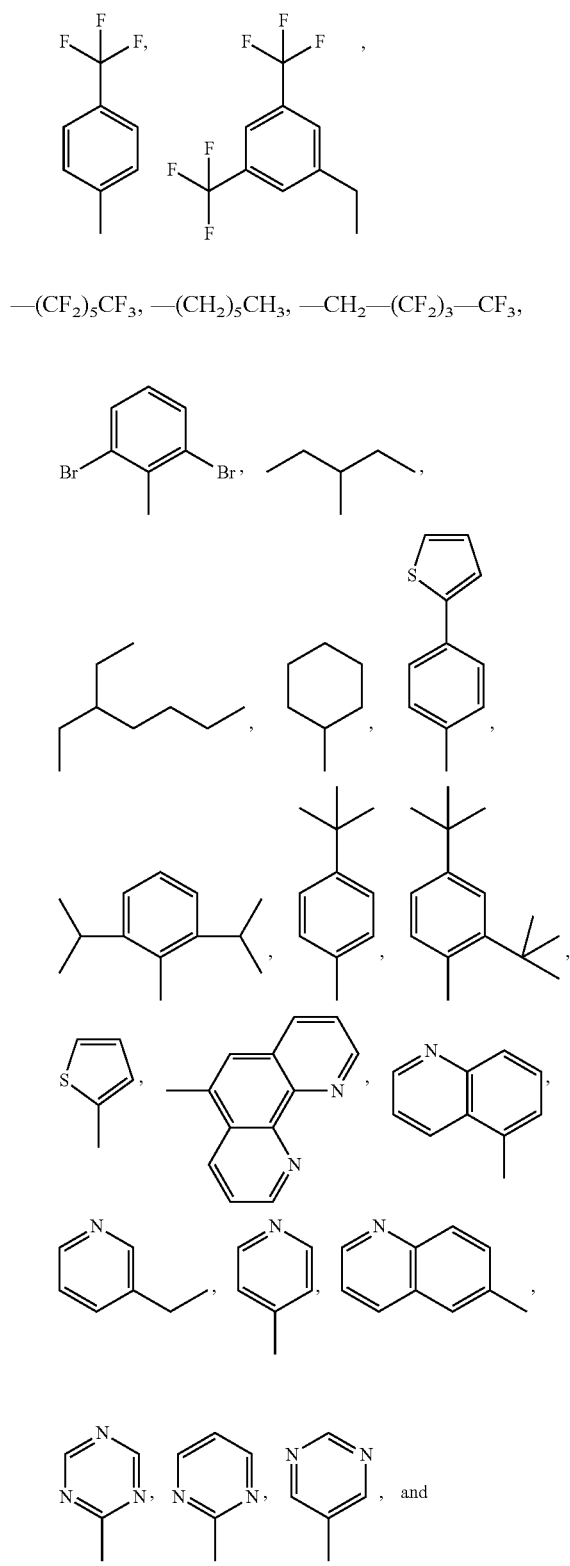
$R_1$ is, preferably, selected from
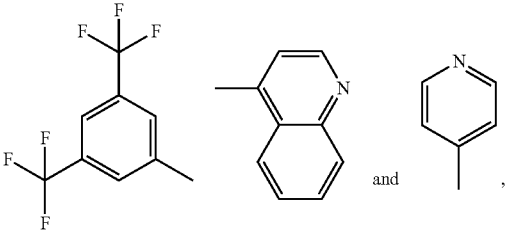
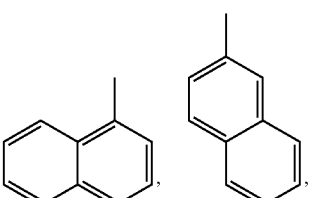
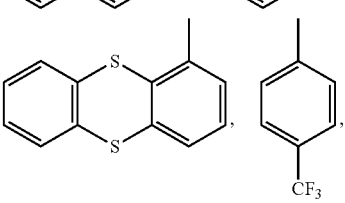
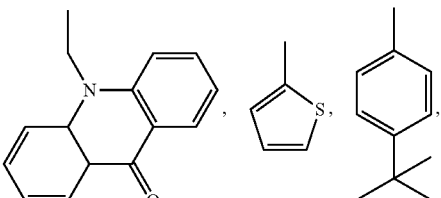
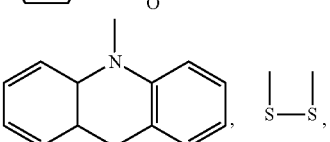
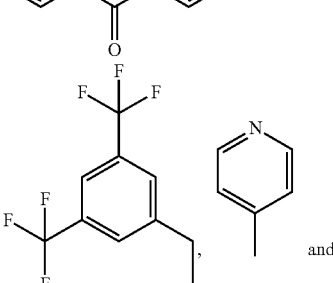
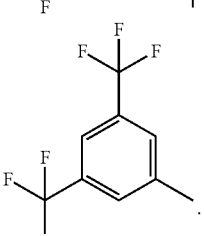
(6) The transparent N or P material of (4) or (5), wherein the material is a naphtalene monoimide dimer (NMI-NMI)-based material represented by the general formula II

II

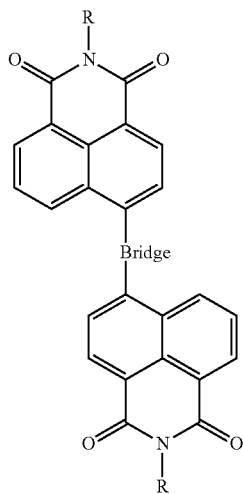

wherein
R is, at each occurrence, independently selected from
—$C_xH_{2x+1}$, —$C_xH_{2x+1}$, —$C_xH_2X_{2x-1}$,

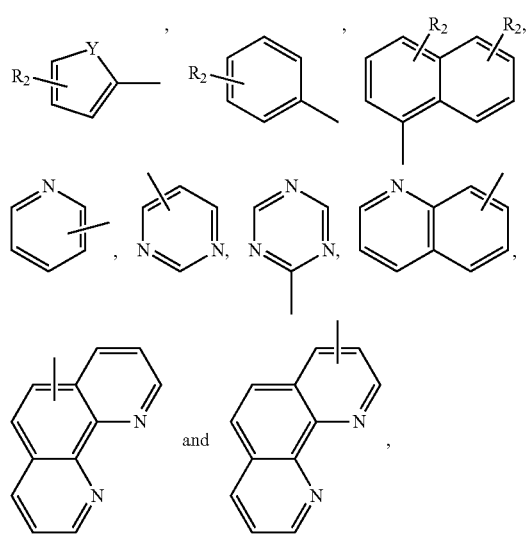

and
Bridge is selected from

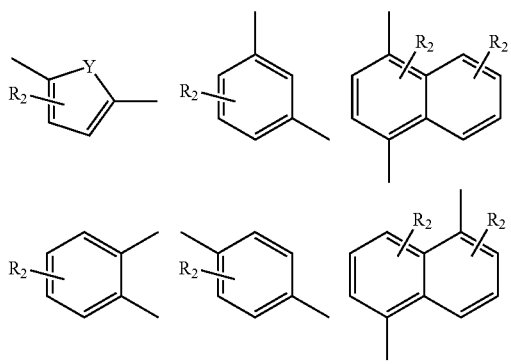

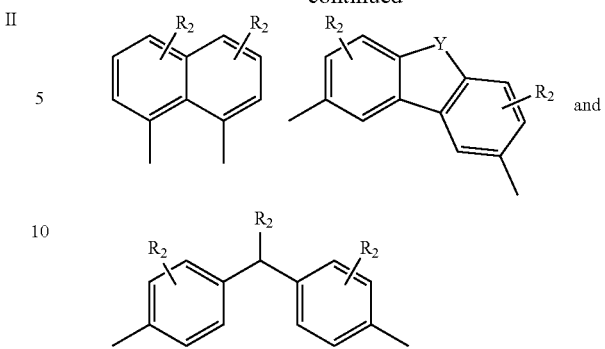

x is an integer from 1 to 10,
X is halogen (F, Cl, Br, I),
Y is selected from $CH_2$, S, O, Se and N—$R_2$,
$R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group,
wherein preferably
R is, preferably, selected from

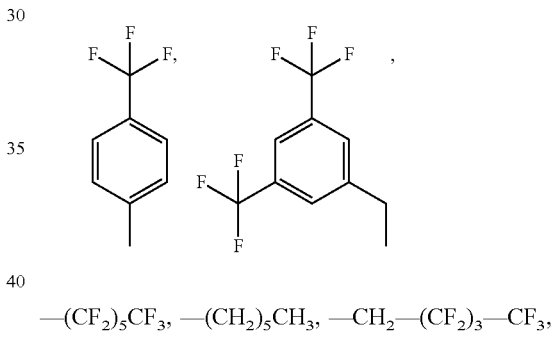

—$(CF_2)_5CF_3$, —$(CH_2)_5CH_3$, —$CH_2$—$(CF_2)_3$—$CF_3$,

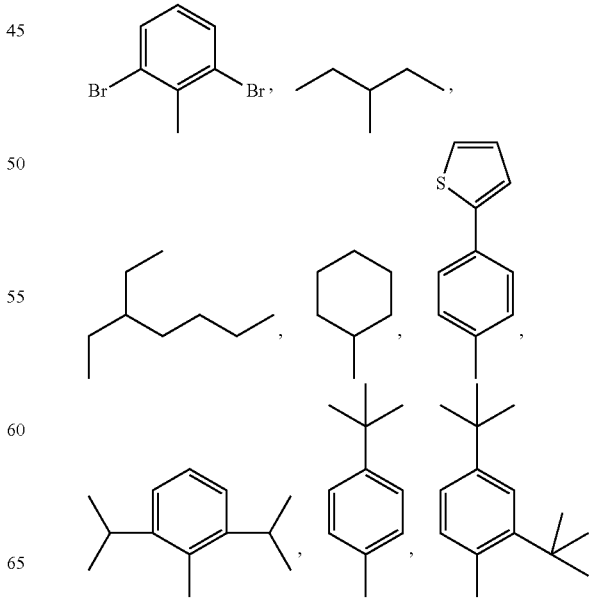

-continued
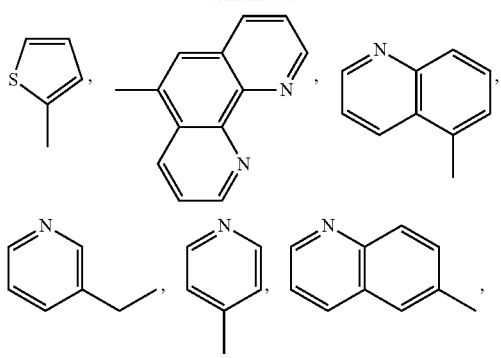
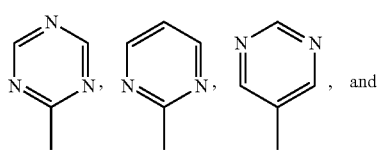
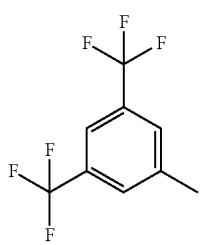
Bridge is, preferably, selected from
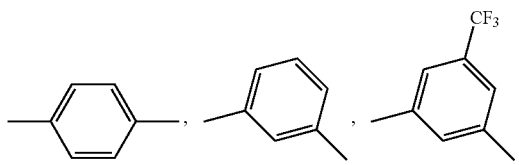
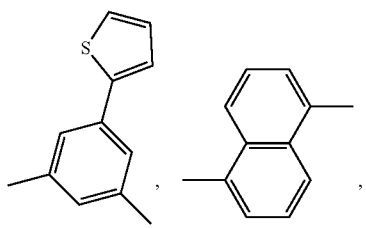
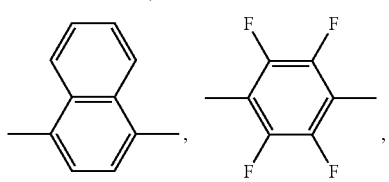
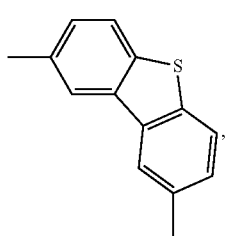
-continued
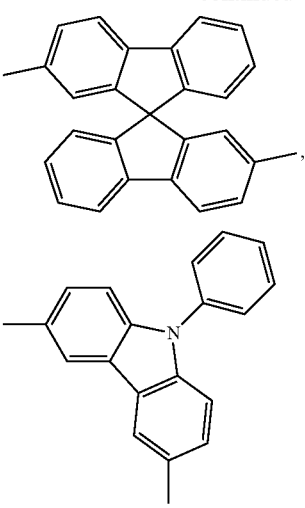
and none (i.e. a direct connection).
(7) The transparent N or P material of (4), wherein the material is a naphtalene diimide (NDI)-based material represented by the general formula III
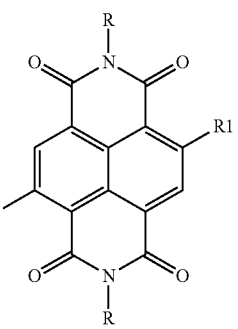
III
wherein
R is, at each occurrence, independently selected from —$C_xH_{2x+1}$, —$C_xX_{2x+1}$, —$C_xH_2X_{2x-1}$,
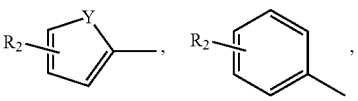
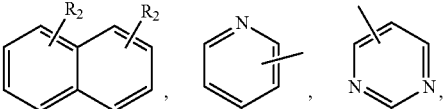
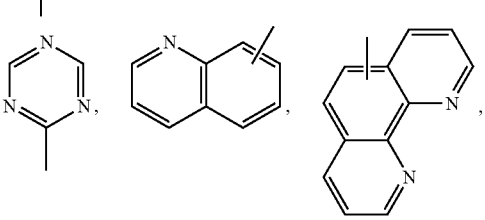

-continued

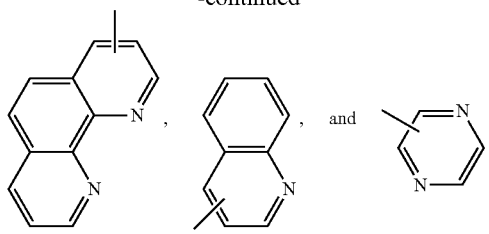

R₁ is, at each occurrence, independently selected from

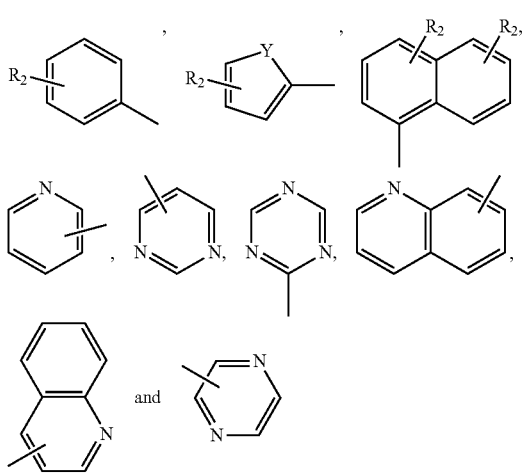

x is an integer from 1 to 10,
X is halogen (F, Cl, Br, I),
Y is selected from CH₂, S, O, Se and N—R₂,
R₂ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group, wherein preferably
R is, preferably, selected from

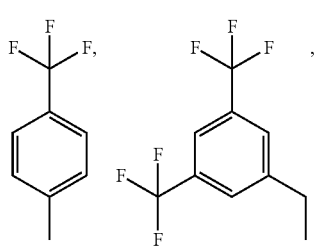

—(CF₂)₅CF₃, —(CH₂)₅CH₃, —CH₂—(CF₂)₃—CF₃,

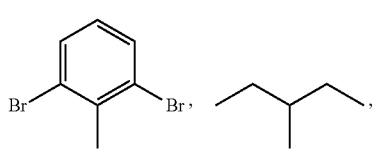

-continued

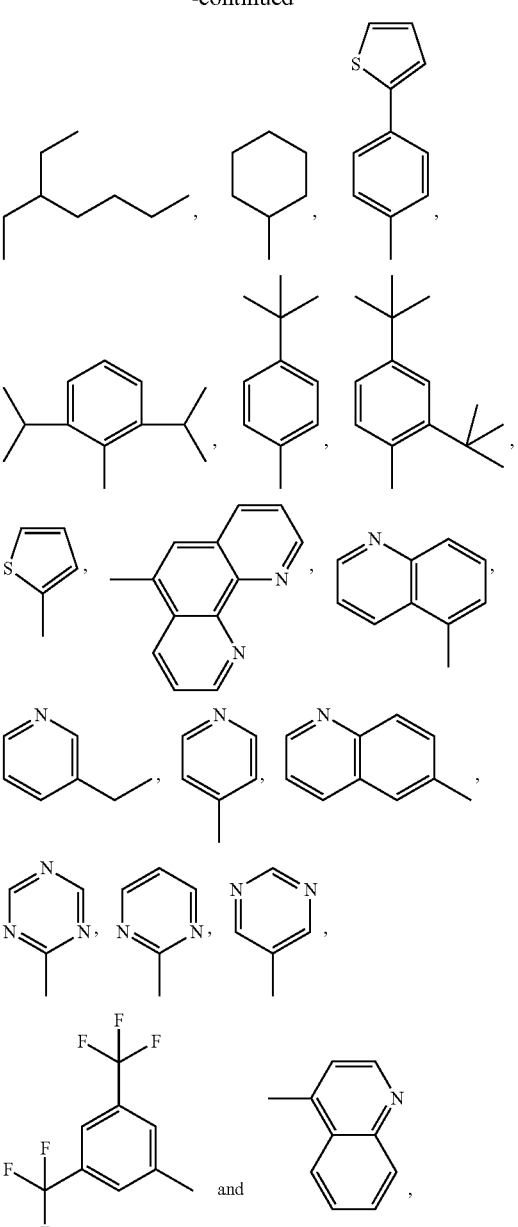

R₁ is, preferably, selected from

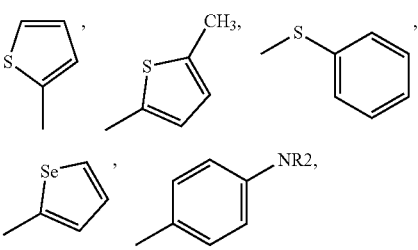

—OCH₂CH₃, —Br, —H,

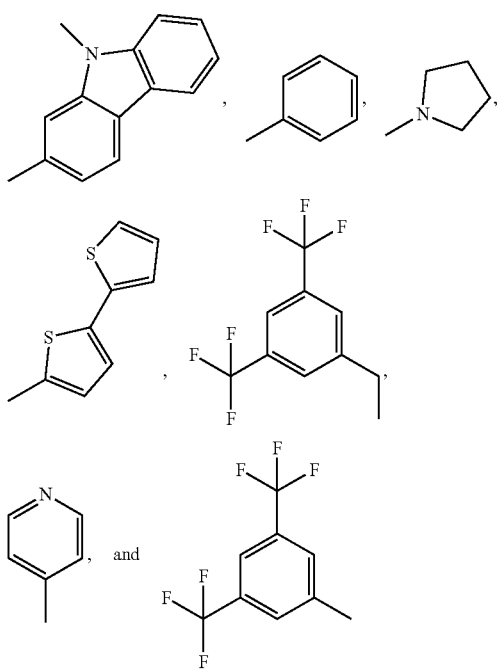

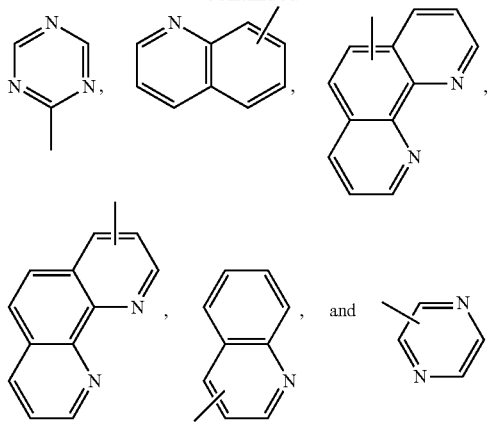

x is an integer from 1 to 10,
X is halogen (F, Cl, Br, I),
Y is selected from $CH_2$, S, O, Se and $N-R_2$,
$R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group,
wherein preferably
R is, preferably, selected from

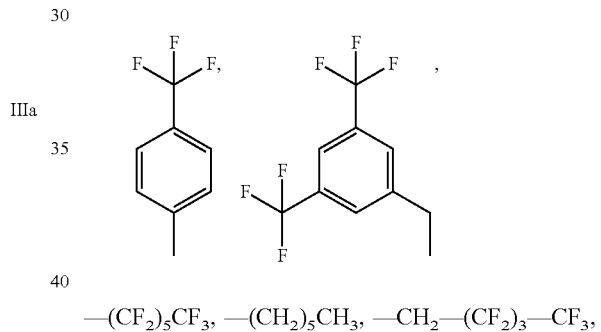

$-(CF_2)_5CF_3$, $-(CH_2)_5CH_3$, $-CH_2-(CF_2)_3-CF_3$,

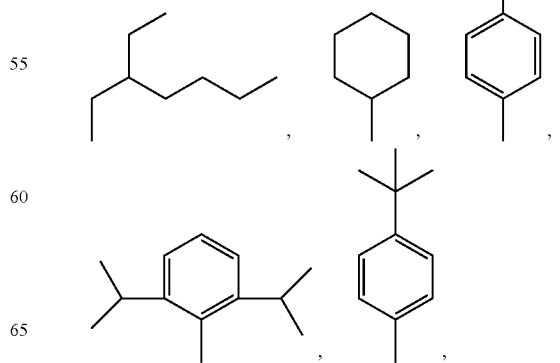

or wherein the material is a naphtalene diimide (NDI)-based material represented by the general formula IIIa

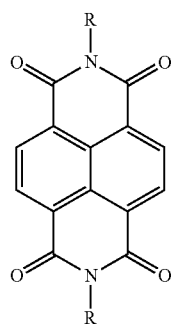

IIIa wherein
R is, at each occurrence, independently selected from $-C_xH_{2x+1}$, $-C_xX_{2x+1}$, $-C_xH_2X_{2x-1}$,

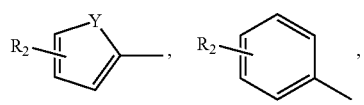

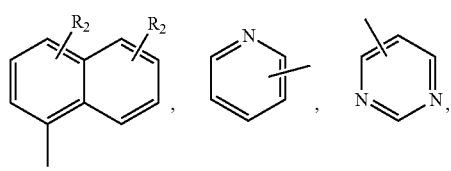

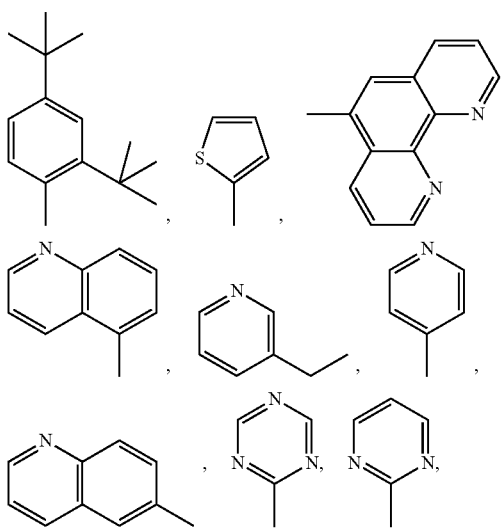
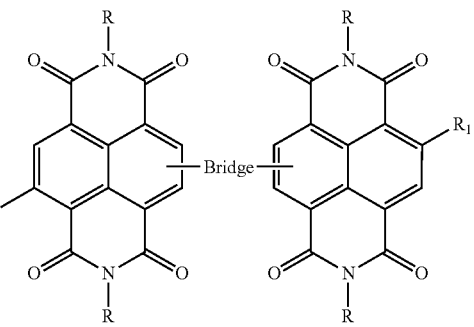
wherein in general formula IV
R is, at each occurrence, independently selected from $-C_xH_{2x+1}$, $-C_xX_{2x+1}$, $-C_xH_2X_{2x-1}$,
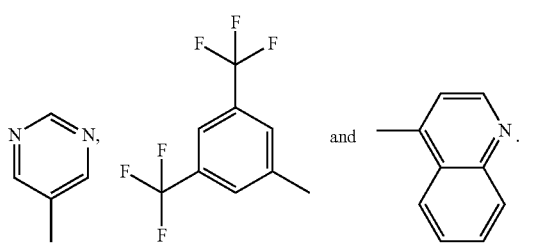
(8) The transparent N or P material of (4) or (7), wherein the material is a naphtalene diimide dimer (NDI-NDI)-based material represented by the general formula IV or V
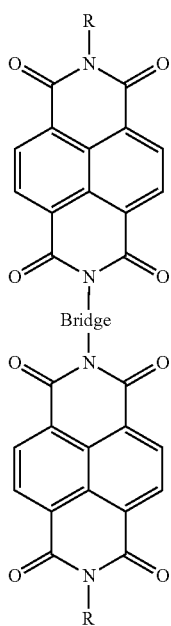
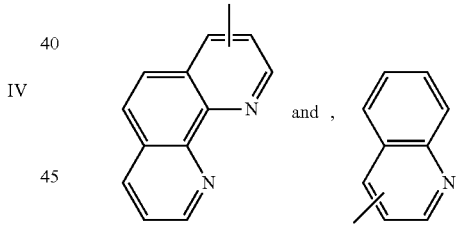
and
Bridge is selected from
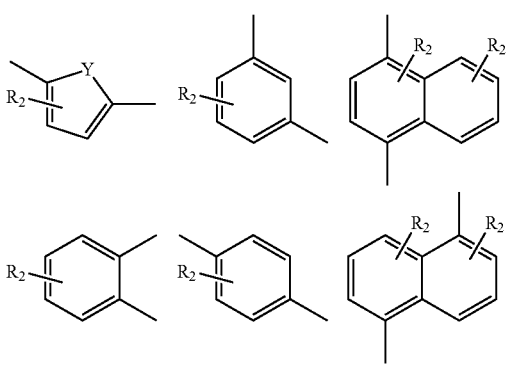

-continued

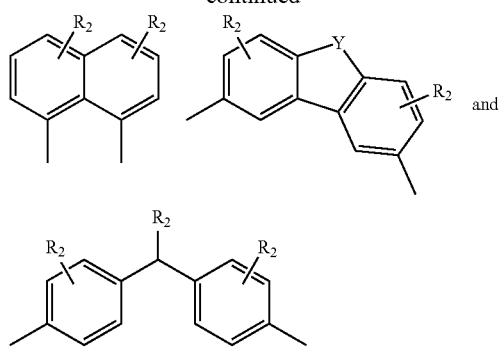
and

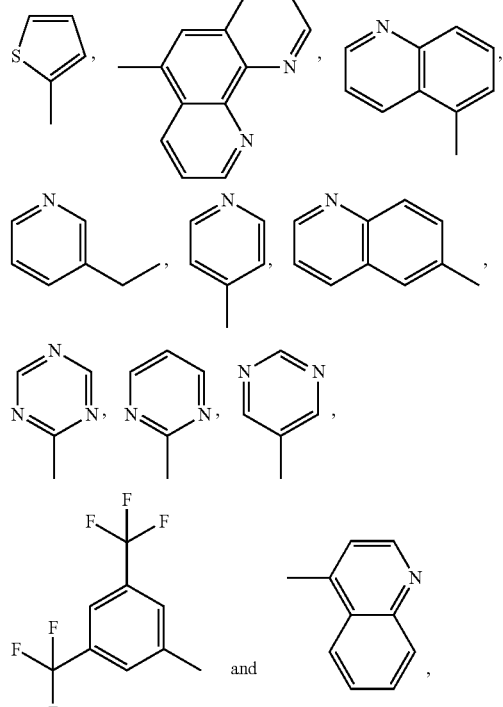
and

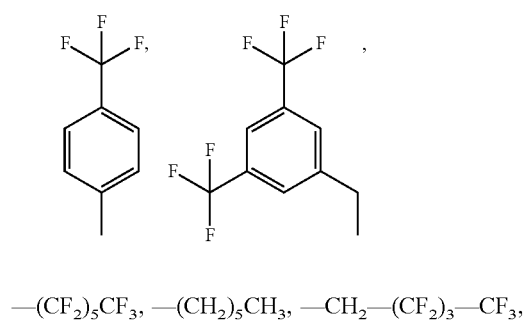

x is an integer from 1 to 10,
X is halogen (F, Cl, Br, I),
Y is selected from CH$_2$, S, O, Se and N—R$_2$,
R$_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group, wherein in general formula IV preferably
R is, preferably, selected from

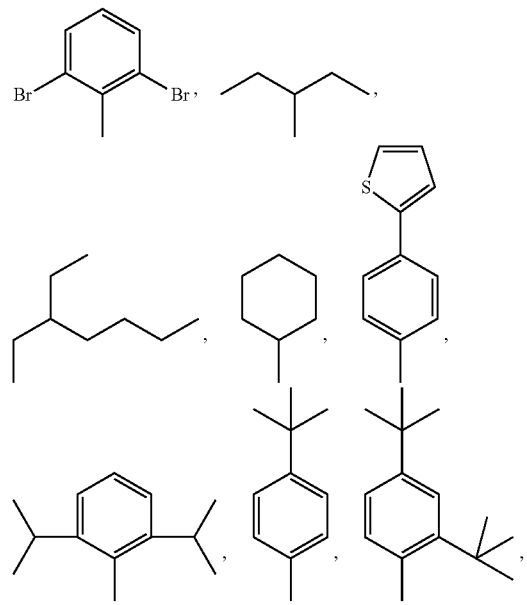

—(CF$_2$)$_5$CF$_3$, —(CH$_2$)$_5$CH$_3$, —CH$_2$—(CF$_2$)$_3$—CF$_3$,

Bridge is, preferably, selected from

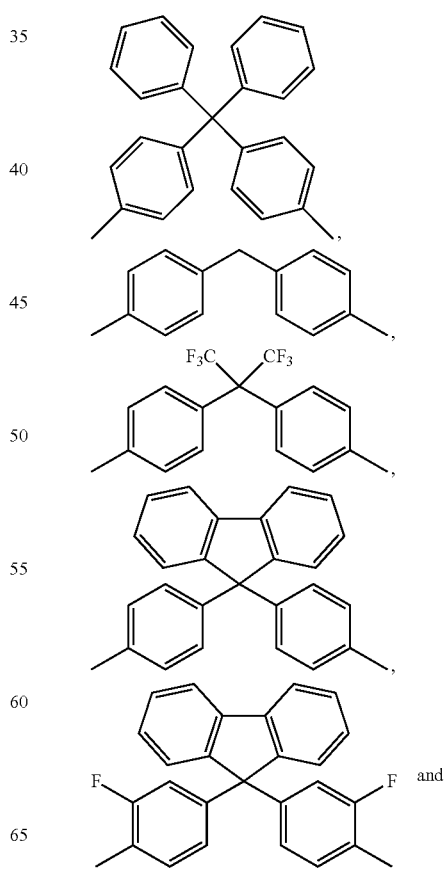
and

-continued

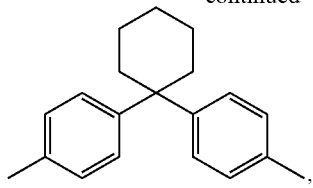

wherein in general formula V
R is, at each occurrence, independently selected from
—$C_xH_{2x+1}$, —$C_xX_{2x+1}$, —$C_xH_2X_{2x-1}$,

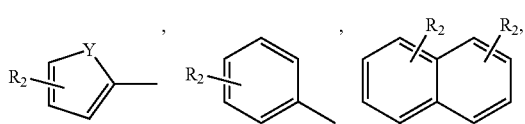

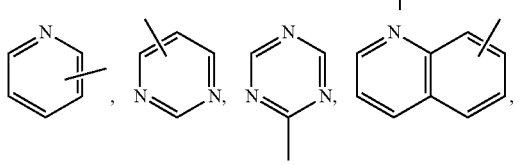

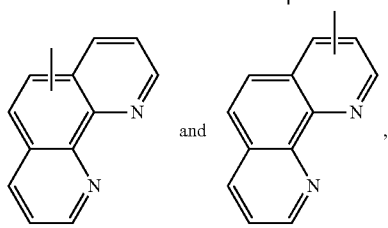

and
$R_1$ is, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated alkyl group, heteroaryl group, fluorenyl group, and
Bridge is selected from

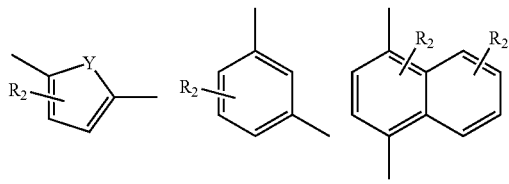

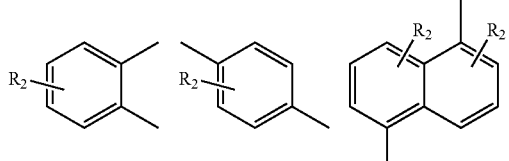

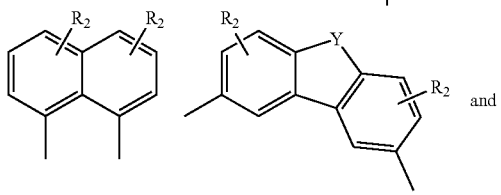

-continued

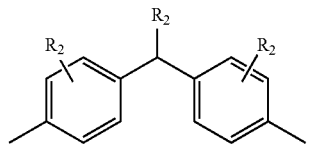

x is an integer from 1 to 10,
X is halogen (F, Cl, Br, I),
Y is selected from $CH_2$, S, O, Se and N—$R_2$,
$R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group, wherein in general formula V preferably
R is, preferably, selected from

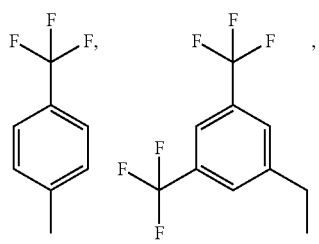

—$(CF_2)_5CF_3$, —$(CH_2)_5CH_3$, —$CH_2$—$(CF_2)_3$—$CF_3$,

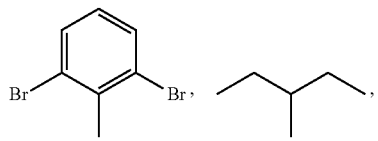 

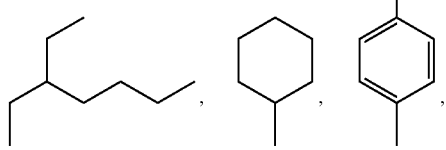

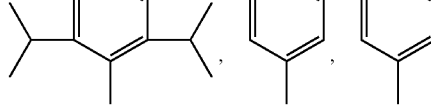

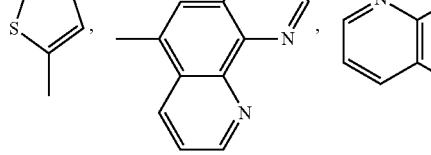

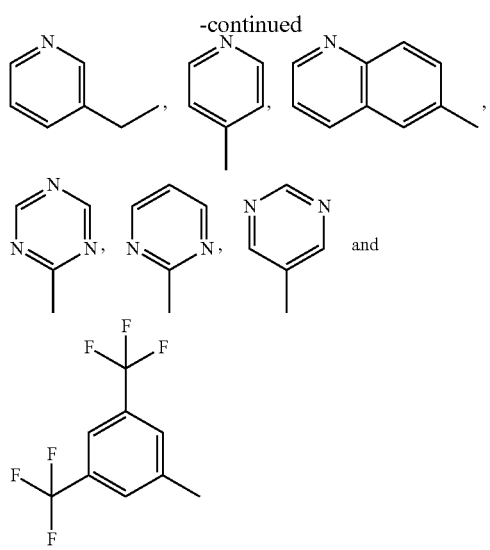
$R_1$ is, preferably, selected from —Br, —H, —OCH$_2$CH$_3$,
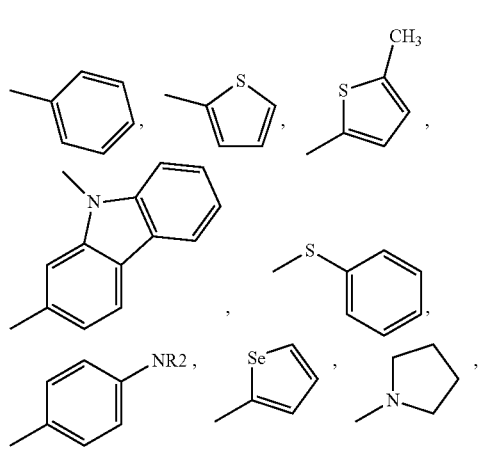
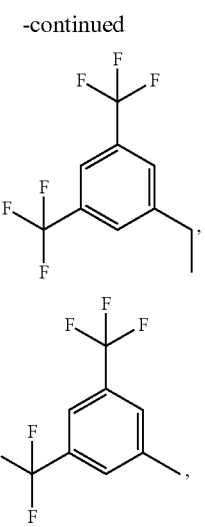
Bridge is, preferably, selected from
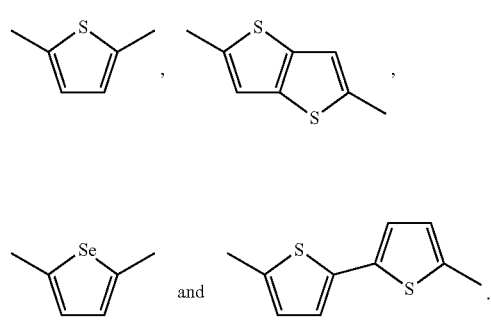
(9) The transparent N or P material of any one of (4) to (8), wherein the material is a naphtalene mono-diimide dimer (NMI-NDI)-based material represented by a general formula selected from general formulas VI to VIII
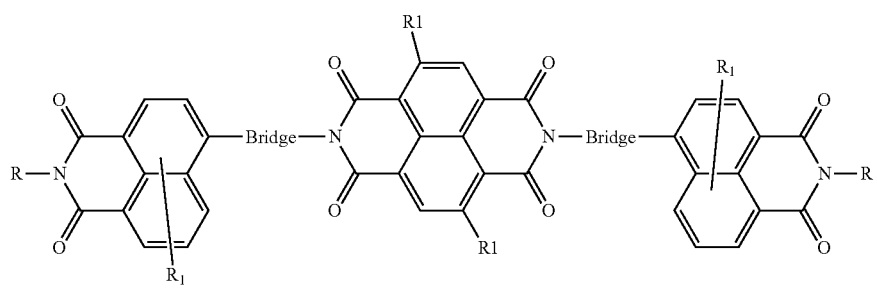
VI
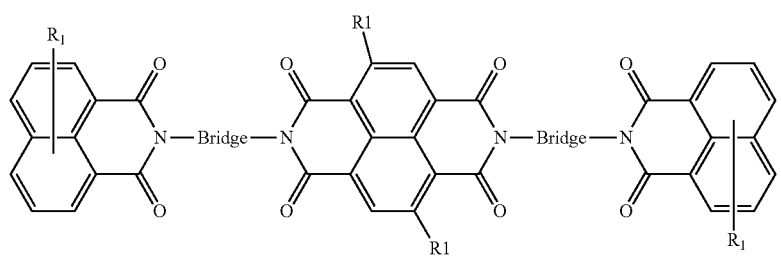
VII -continued

VIII

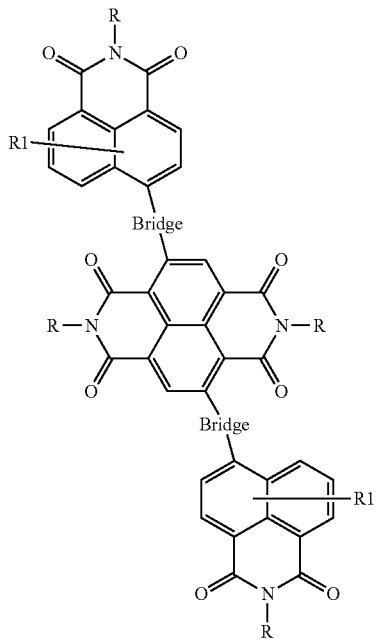

wherein

R is, at each occurrence, independently selected from —$C_xH_{2x+1}$, —$C_xX_{2x+1}$, —$C_xH_2X_{2x-1}$,

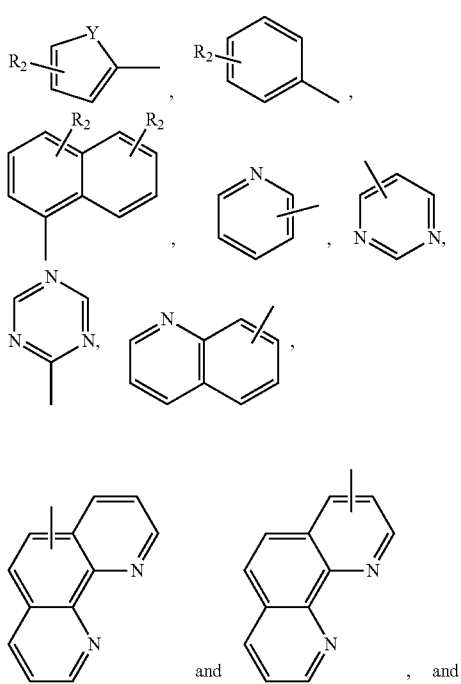

$R_1$ is, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated alkyl group, heteroaryl group, fluorenyl group, and Bridge is selected from x is an integer from 1 to 10,
X is halogen (F, Cl, Br, I),
Y is selected from $CH_2$, S, O, Se and N—$R_2$,
$R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group.

(10) The transparent N or P material of (4), wherein the material is a thiophene- or selenophene-based material represented by a general formula selected from general formulas IX to XI

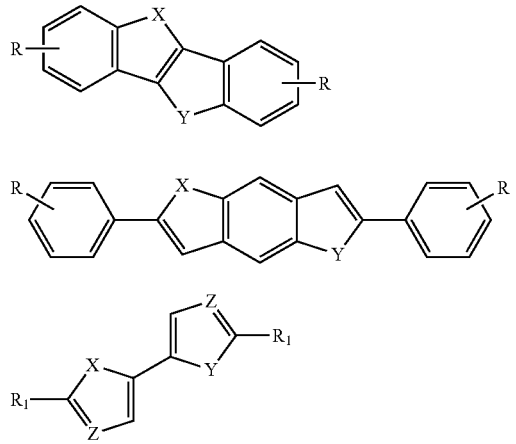

IX

X

XI wherein
- X and Y are the same or different and are, at each occurrence, independently selected from $CH_2$, S, O, Se, N—R and Si—$R_2$,
- Z is selected from CH and N,
- R and $R_1$ are the same or different and are, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group, wherein preferably
- X is, preferably, selected from S and Se,
- Y is, preferably, selected from S and Se,
- Z is, preferably, selected from CH and N, R is, preferably, selected from

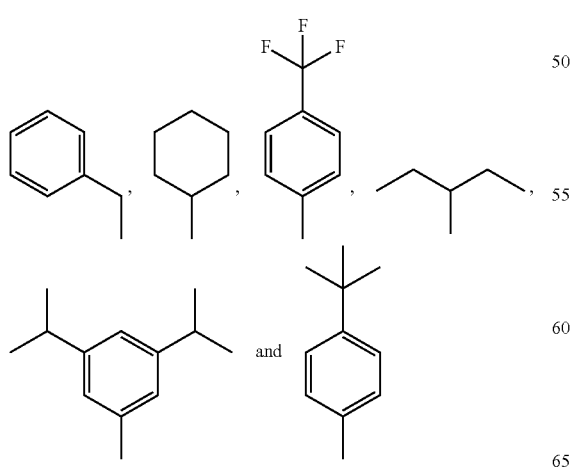

$R_1$ is, preferably, selected from

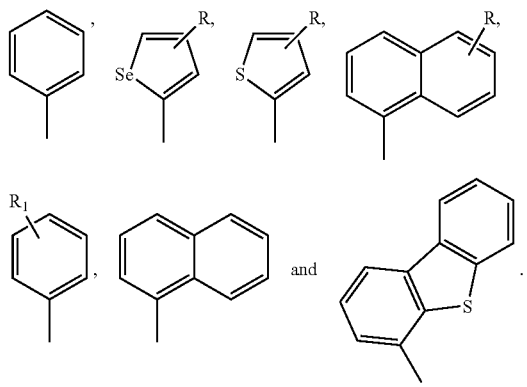

(11) The transparent N or P material of (4) or (10), wherein the material is a thiophene- or selenophene-based material represented by the general foiniula XII or XIIb

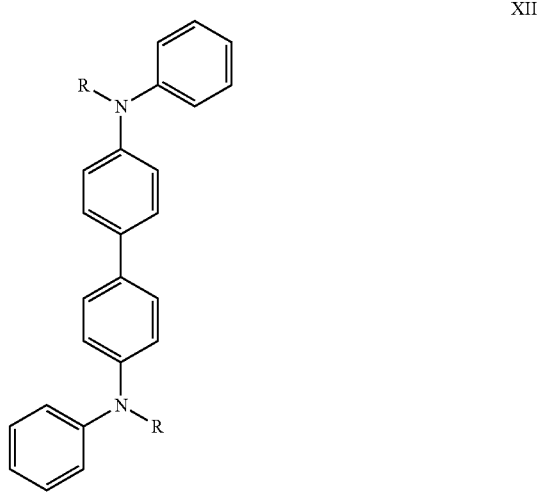

XII

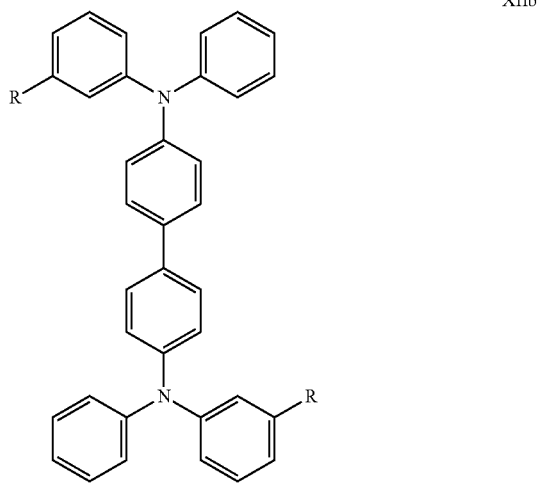

XIIb wherein
R is, at each occurrence, independently selected from
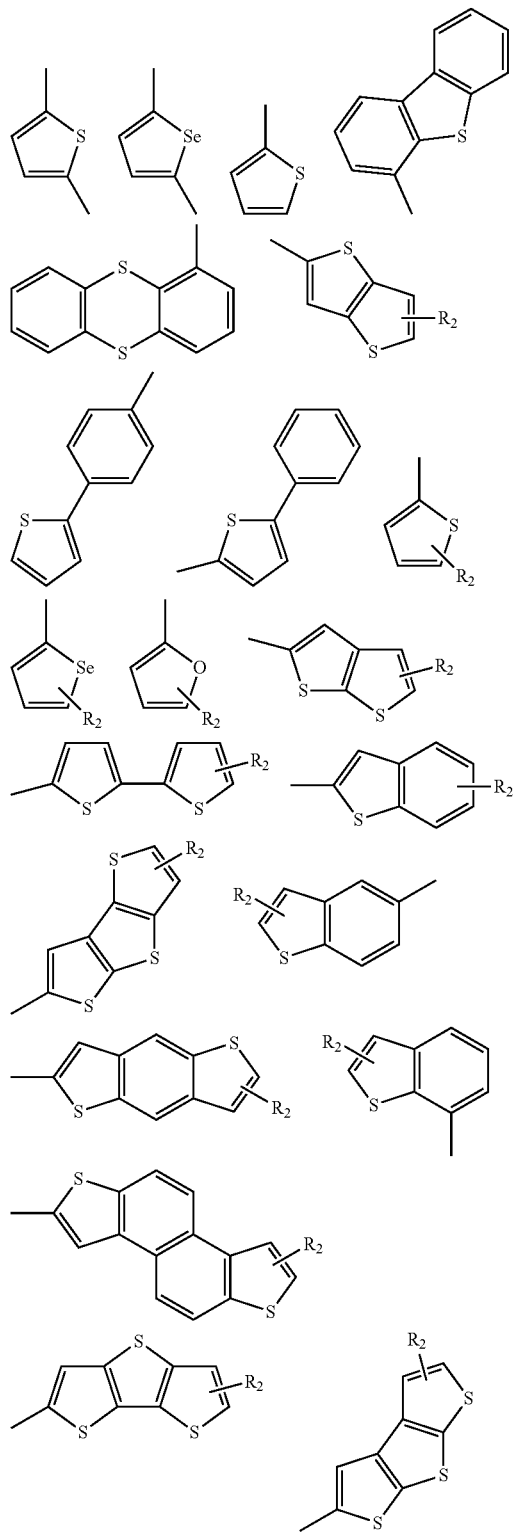
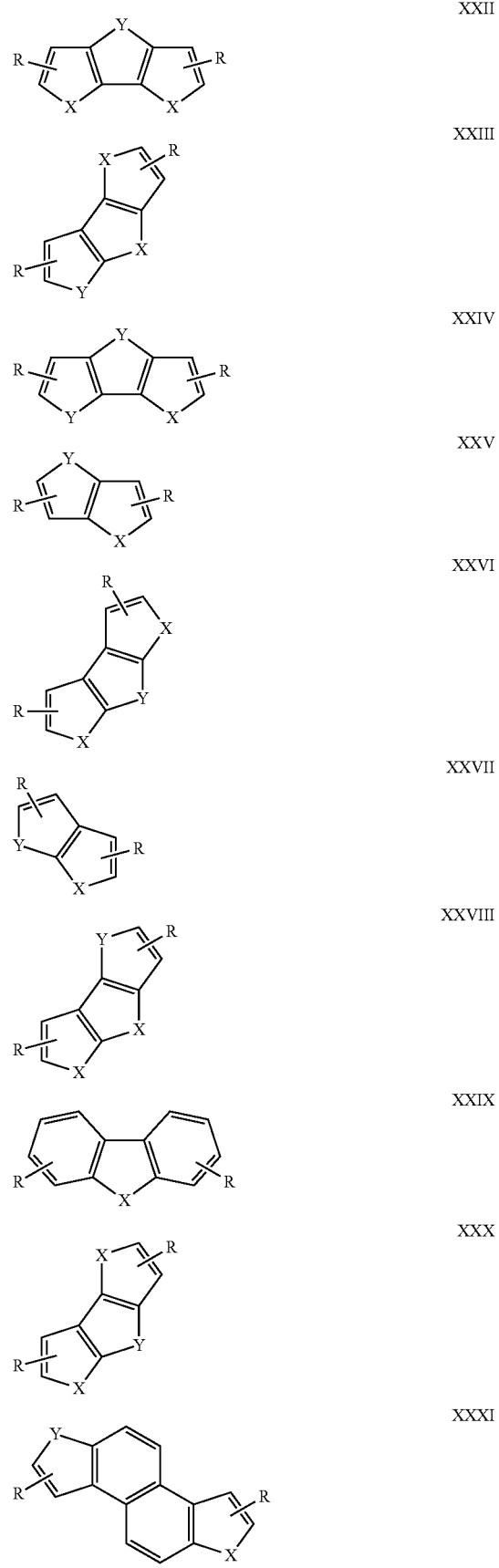
(12) The transparent N or P material of (4), wherein the material is a thiophene- or selenophene-based material represented by the general formulas XXII to XXXIII:

XXXII 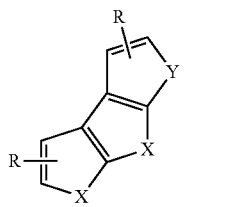

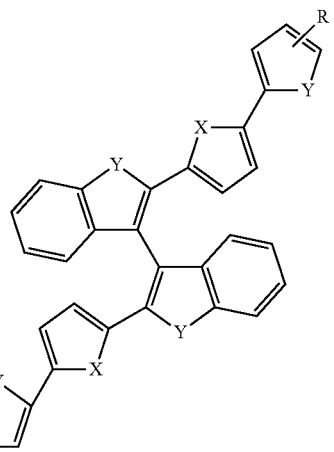

XXXIII 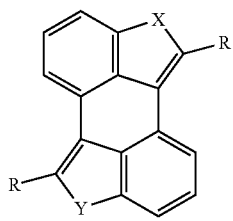

XXXIV 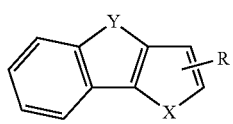

XXXV 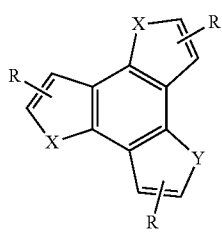

wherein
X and Y are the same or different and are, at each occurrence, independently selected from CH₂, S, O, Se, N—R and Si—R₂,
Z is selected from CH and N,
R and R₁ are the same or different and are, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group,
wherein preferably
X is, preferably, selected from S and Se,
Y is, preferably, selected from S and Se,
Z is, preferably, selected from CH and N,
R is, preferably, selected from XXXVI 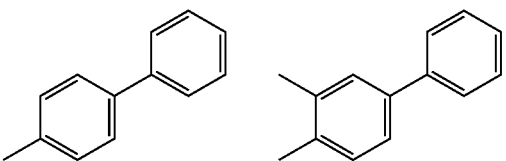

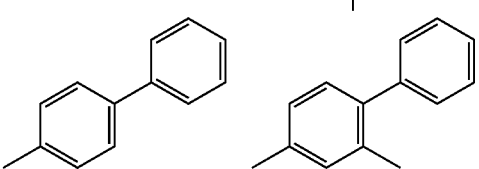

XXXVII 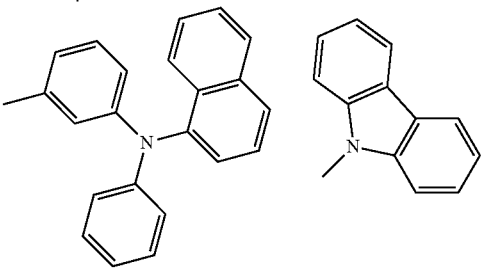

XXXVIII 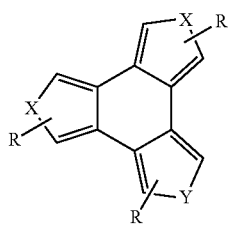

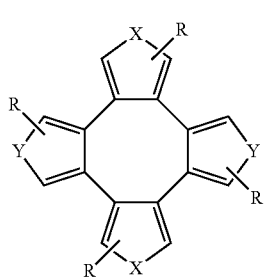

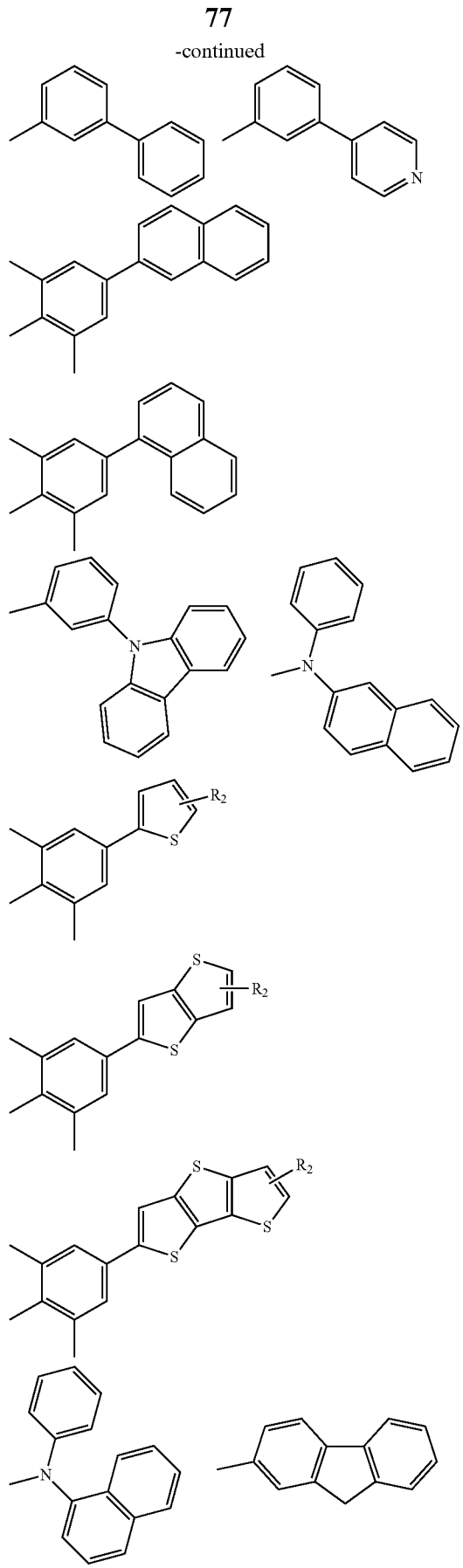
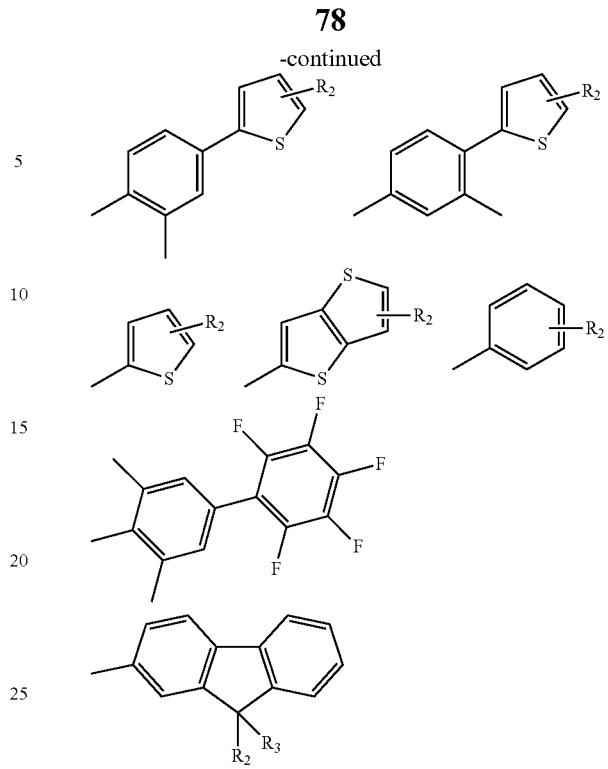

wherein $R_2$ and $R_3$ are the same or different and are, at each occurrence, independently selected from H, $CH_3$, alkyl, aryl.

(13) The transparent N or P material of (10) or (12), wherein the material is a thiophene- or selenophene-based material represented by the general formula XXXIX or XL:

$$T\text{-}B\text{-}T \qquad\qquad XXXIX$$

wherein

T is selected from a structure with one of the general formulas IX, X, XI or XXII to XXXVIII, as defined in (10) or (12), with X and Y being the same or different and being, at each occurrence, independently selected from $CH_2$, S, O, Se, N—R and Si—$R_2$, Z being selected from CH and N, B is selected from any one of

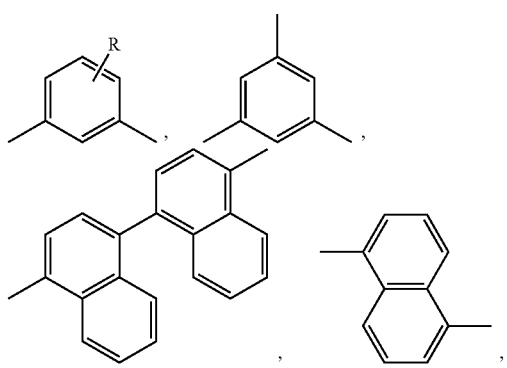

-continued

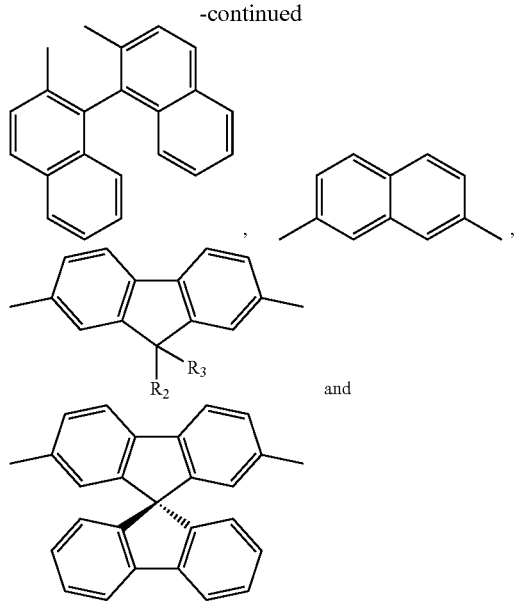

with R₂ and R₃ being the same or different and are, at each occurrence, independently selected from H, CH₃, alkyl, aryl.

R is at each occurrence, independently selected from H, alkyl, aryl,

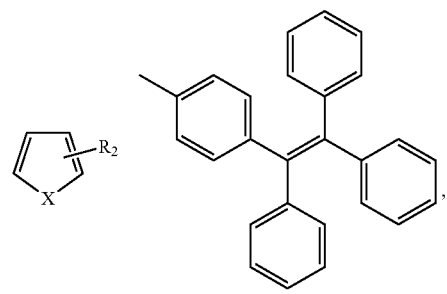

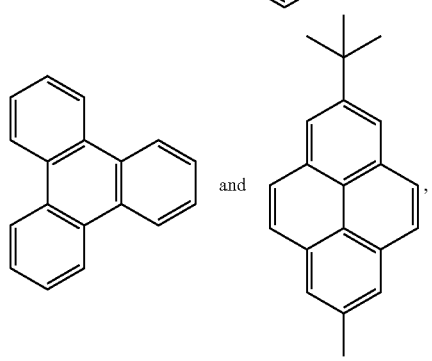

T-H  XL wherein

T is selected from a structure with one of the general formulas IX, X, XI or XXII to XXXVIII, as defined (10) or (12), with X and Y being the same or different and being, at each occurrence, independently selected from CH₂, S, O, Se, N—R and Si—R₂, Z being selected from CH and N, H is selected from any one of

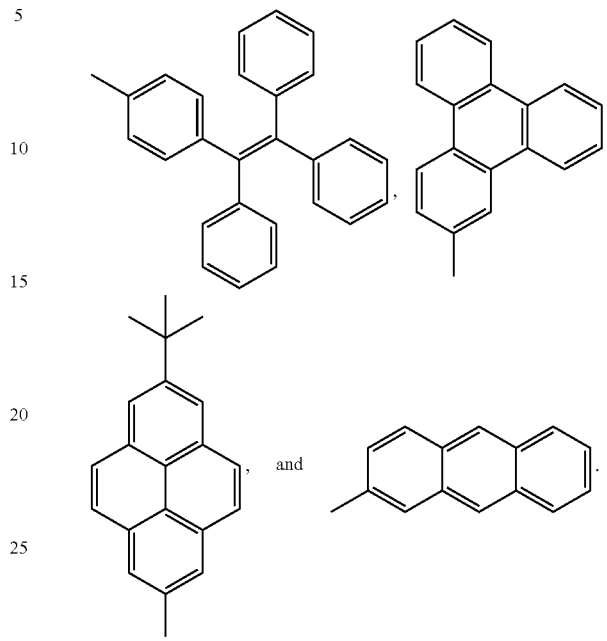

(14) The transparent N or P material of (4), wherein the material is a dithienopyrrol (DTP)-based material represented by the general formula XIII

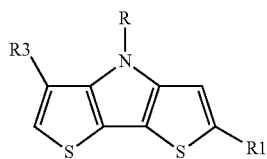
XIII wherein

R is selected from selected from $-C_xH_{2x+1}$, $-C_xX_{2x+1}$, $-C_xH_2X_{2x-1}$,

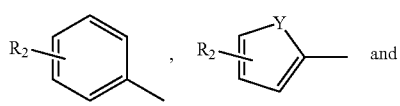

R₁ is selected from

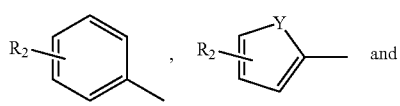

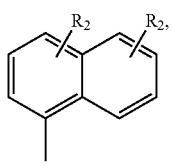

R₃ is selected from linear and branched alkyl group, cycloalkyl group, halogenated alkyl group, halogen atoms, x is an integer from 1 to 10, X is halogen (F, Cl, Br, I), Y is selected from CH₂, S, O, Se and N—R₂, R₂ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group, wherein, preferably, R is, preferably, selected from

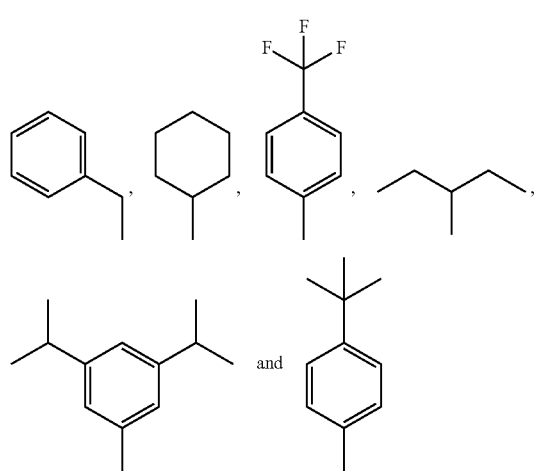

R₁ is, preferably, selected from

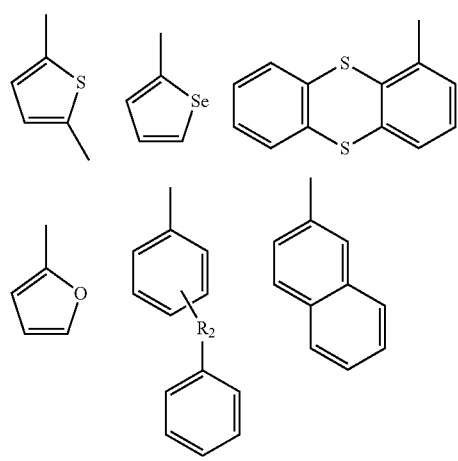

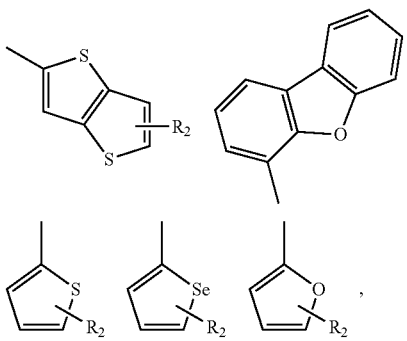

R₂ is, preferably, selected from linear and branched alkyl group.

(15) The transparent N or P material of (4) or (14), wherein the material is a dithienopyrrol dimer (DTP dimer)-based material represented by a general formula selected from general formulas XIV to XVI

XIV

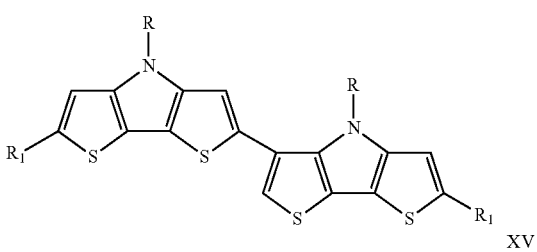

XV

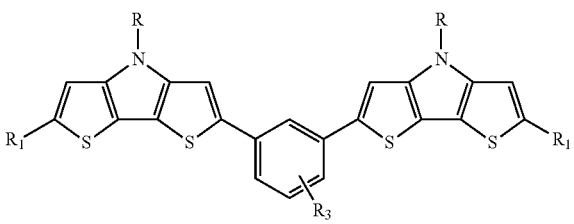

XVI

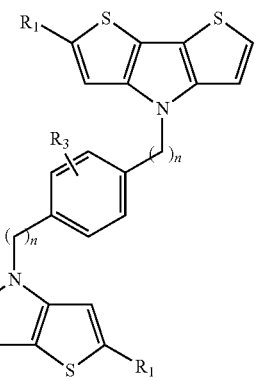

wherein

R is, at each occurrence, independently selected from selected from —C$_x$H$_{2x+1}$, —C$_x$X$_{2x+1}$, —C$_x$H$_2$X$_{2x-1}$,

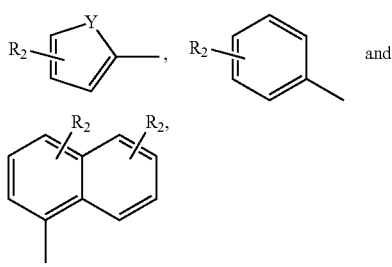

$R_1$ is, at each occurrence, independently selected from

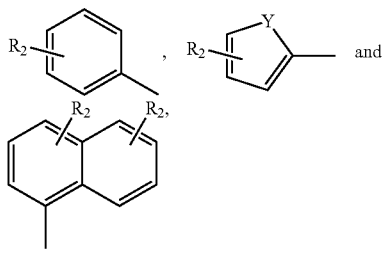

$R_3$ is selected from linear and branched alkyl group, cycloalkyl group, halogenated alkyl group, halogen atoms, n is 0 or 1, x is an integer from 1 to 10, X is halogen (F, Cl, Br, I), Y is selected from $CH_2$, S, O, Se and $N-R_2$, $R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group, wherein, preferably, R is, preferably, selected from

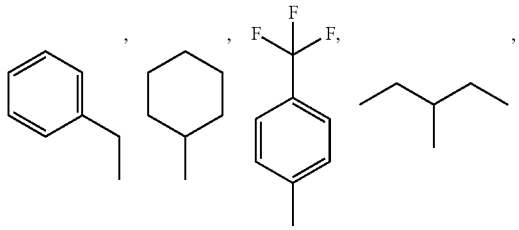

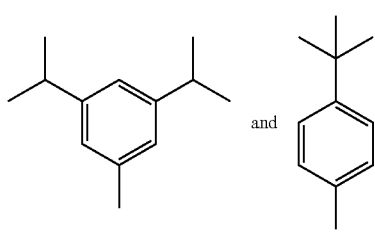

$R_1$ is, preferably, selected from

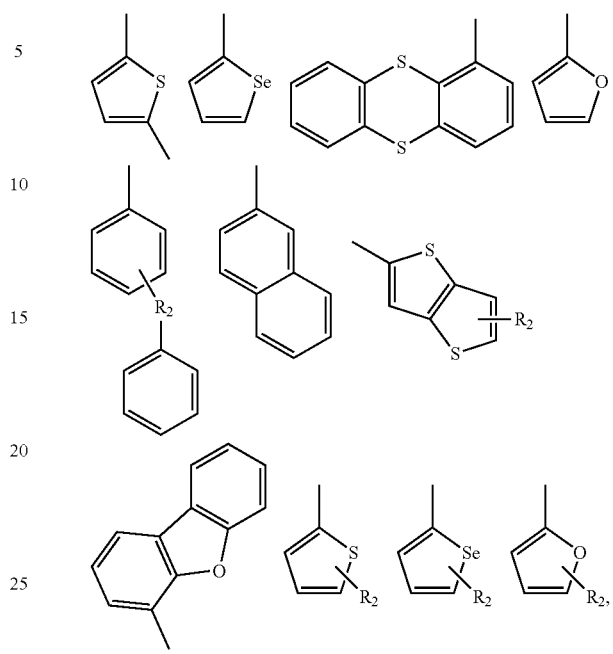

$R_2$ is, preferably, selected from linear and branched alkyl group.

(16) The transparent N or P material of (4), wherein the material is an anthracene- or anthracene dimer-based material represented by the general formula XVII or XVIII

XVII

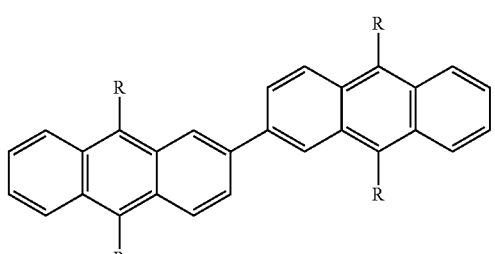

XVIII

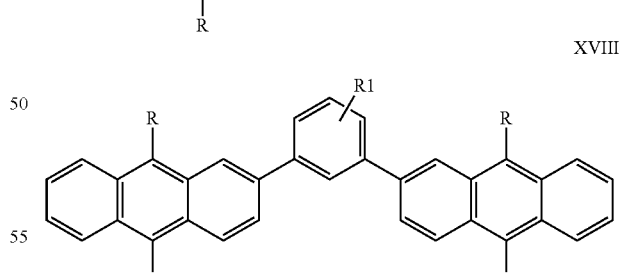

wherein

R is, at each occurrence, independently selected from

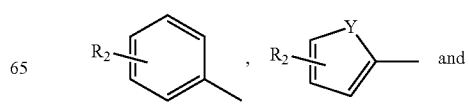

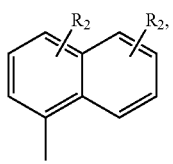

$R_1$ is selected from linear and branched alkyl group, cycloalkyl group, halogenated alkyl group, halogen atoms, Y is selected from $CH_2$, S, O, Se and $N-R_2$, $R_2$ is, at each occurrence, independently selected from H, linear and branched alkyl group, cycloalkyl group, halogenated alkyl group, halogen atoms, alkyl or aryl sulfanyl group, alkyl or aryl amine, aryl group, halogenated alkyl group, heteroaryl group, fluorenyl group, wherein, preferably, R is, preferably, selected from

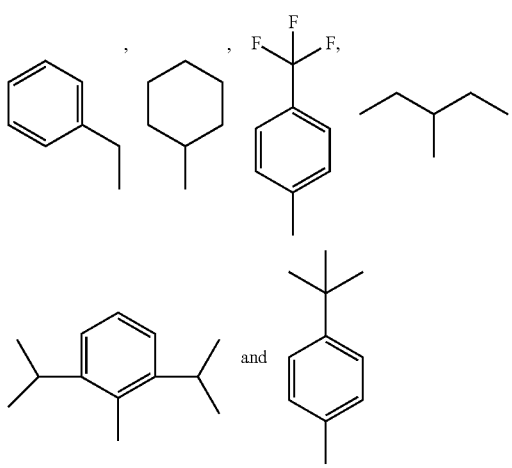

$R_1$ is, preferably, selected from linear and branched alkyl group.

(17) The transparent N or P material of (4), wherein the material is a zinc coordination complex-based material represented by a general formula selected from general formulas XIX to XXI

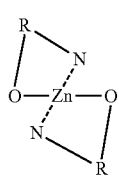
XIX

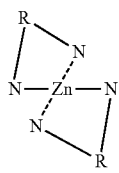
XX

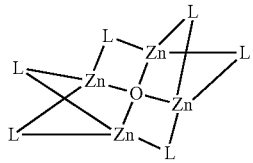
XXI wherein

ORN is, at each occurrence, independently selected from

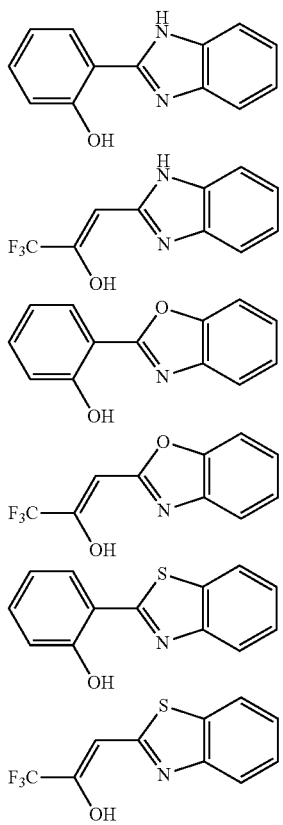

NRN is, at each occurrence, independently selected from

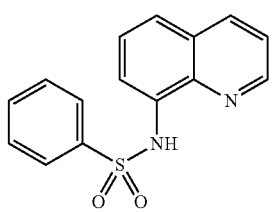

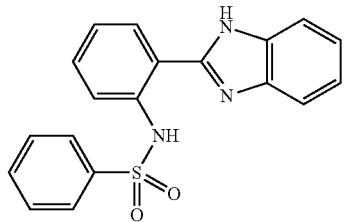

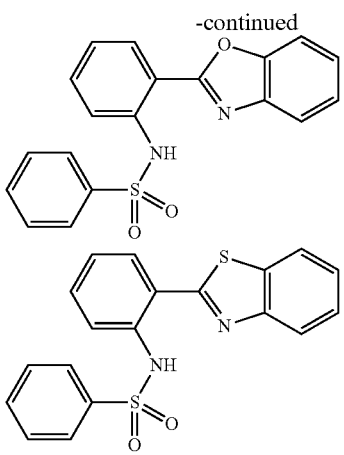

L is, at each occurrence, independently selected from

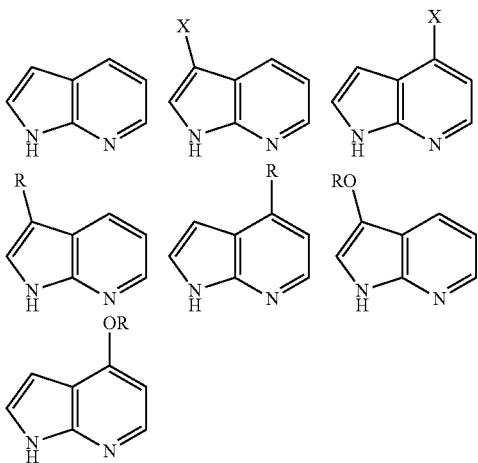

X is selected from halogen (F, Cl, Br, I), CN, CF$_3$, COOH, NH$_2$,

R is selected from alkyl and aryl.

(18) A P:N heterojunction, preferably a P1:P2:N1:N2 heterojunction, including a transparent N material according to any one of (1) to (17) and/or a transparent P material according to any one of (1) to (17),
and including a further N and/or P material,
wherein the further N and/or P material preferably exhibits absorption in the visible wavelength range (about 400 to about 700 nm).

(19) Use of a transparent N and/or P material according to any of (1) to (17) in an absorption layer,
and including a further N and/or P material,
wherein the further N and/or P material preferably exhibits absorption in the visible wavelength range (about 400 to about 700 nm).

(20) Use of a transparent N and/or P material according to any one of (1) to (17) in a photoelectric conversion layer and/or in an organic and/or hybrid module for optoelectronic application, such as image sensor, photodiode, organic photovoltaics, including organic photoelectric conversion layer(s), OLED and OTFT organic modules,
and including a further N and/or P material,
wherein the further N and/or P material preferably exhibits absorption in the visible wavelength range (about 400 to about 700 nm).

(21) A photoelectric conversion layer including a transparent N and/or P material according to any one of (1) to (17),
and including a further N and/or P material,
wherein the further N and/or P material preferably exhibits absorption in the visible wavelength range (about 400 to about 700 nm).
and optionally including further molecule(s).

(22) An absorption layer including a transparent N and/or P material according to any one of (1) to (17),
and including a further N and/or P material, and
optionally including further molecule(s).
wherein the further N and/or P material preferably exhibits absorption in the visible wavelength range (about 400 to about 700 nm).

(23) A device, including transparent N and/or P material(s) according to any one of (1) to (17) or photoelectric conversion layer(s) according to (21),
wherein said device is preferably an organic image sensor, an hybrid image sensor, photodiode, organic photovoltaics, organic light-emitting diode (OLED), organic thin-film transistor (OTFT).

(24) The device according to (23), wherein said photoelectric conversion layer exhibits photo response in the visible absorption range.

(25) The device according (23) or (24), including transparent N and/or P material(s) according to any one of (1) to (17) or photoelectric conversion layer(s) according to (21), and/or including further N and/or P material(s) preferably exhibiting absorption in the visible wavelength range (about 400 to about 700 nm),
and/or including further molecule(s).

(26) An organic image sensor, including
(a) an organic photoelectric conversion unit including photoelectric conversion layer(s) according to (21),
(b) at least one electrode,
(c) a substrate,
(d) optionally, a second electrode on top of said photoelectric conversion layer(s).

(27) A hybrid Silicon-organic image sensor or organic image sensor, including
(a) an organic photoelectric conversion unit or units including photoelectric conversion layer(s) according to (21),
(b) optionally, a Si based photoelectric conversion unit,
(c) metal wiring,
(d) a (CMOS) substrate,
(e) insulating layer(s), preferably oxide.

(28) The organic image sensor according to (26) or (27), wherein said organic photoelectric conversion unit includes different layers,
such as n-type material, p-type material, n-buffer layer and/or p-buffer layer or combinations or mixtures thereof.

(29) A method for synthesis of a naphtalene monoimide (NMI)-based materials (represented by the general formula I) and naphtalene monoimide dimer (NMI-NMI)-based materials (represented by the general formula II), including the step(s) of
imidization of 4-Bromo-1,8-naphthalic anhydride derivatives in the presence of a primary amine and acid,
followed by the palladium catalyzed Suzuki Coupling with the specific boronic ester or "bridge"—boronic ester.

(30) A method for synthesis of a naphtalene diimide (NDI)-based materials (represented by the general formula III), including the steps of:
imidization of 2,6-dibromonaphthalene-1,4,5,8-tetracarboxylic dianhydride derivatives in the presence of a R-primary amine and acid, followed by the palladium catalyzed Suzuki Coupling with the specific R1-boronic ester.

(31) A method for synthesis of a naphtalene diimide dimer (NDI-NDI)-based material (represented by the general formula IV) including the steps of mono imidization of 2,6-dibromonaphthalene-1,4,5,8-tetracarboxylic dianhydride derivatives in the presence of a R-primary amine and acid, followed by a second imidization in the presence of a "Bridge"-diamine and acid.

(32) A method for synthesis of a naphtalene diimide dimer (NDI-NDI)-based material (represented by the general formula V) including the steps of imidization of 2,6-dibromonaphthalene-1,4,5,8-tetracarboxylic dianhydride derivatives in the presence of a R-primary amine and acid, followed by a mono palladium catalyzed Suzuki Coupling with the specific R1-boronic ester, followed by a second palladium catalyzed Suzuki Coupling with the specific Bridge-diboronic ester.

(33) A method for synthesis of a naphtalene mono-diimide dimer (NMI-NDI)-based material (represented by a general formula selected from general formulas VI to VIII) including the steps of imidization of corresponding 2,6-dibromonaphthalene-1,4,5,8-tetracarboxylic dianhydride with the appropriate amine derivatives, followed by one or several palladium catalyzed Suzuki Coupling with the specific diboronic ester.

(34) A method for synthesis of dithienopyrrol dimer (DTP dimer)-based materials (represented by a general formula selected from general formulas XIV and XV) including the steps of palladium catalyzed Buchwald-Hartwig coupling of 3,3'-dibromo-2,2'-bithiophene with the corresponding R-amine to receive the N-substituted dithienopyrrole (DTP) core unit, bromination with N-bromo-succinimide, followed by mono-palladium catalyzed Suzuki Coupling with R1-boronic ester, and followed by a further palladium catalyzed Suzuki Coupling with the specific R2-phenylsubstituted di boronic ester.

(35) A method for synthesis of dithienopyrrol dimer (DTP dimer)-based material (represented by a general formula XVI) including the steps of palladium catalyzed Buchwald-Hartwig coupling of 3,3'-dibromo-2,2'-bithiophene with the corresponding R2-phenylsubstituted diamine to receive the N-substituted dithienopyrrole (DTP) dimer core unit, bromination with N-bromo-succinimide, followed by mono-palladium catalyzed Suzuki Coupling with R1-boronic ester, and followed by a further palladium catalyzed Suzuki Coupling with the specific R2-phenylsubstituted di boronic ester.

(36) A method for synthesis of zinc coordination complex-based materials (represented by a general formula selected from general formulas XIX, XX and XI) including the steps of—combining ligands of the type (HO—RN) and (HN—RN) with zinc acetate dehydrate and a base in refluxing methanol.

The term "N material", as used herein, refers to refers to a material accepting an electron.

The term "P material", as used herein, refers to refers to a material donating an electron.

The term "naphtalene monoimide" or "NMI" or naphtalene monoimide-based material", as used herein, refers to a molecule based on 1,4-naphthalenemonoimides structures.

The term "naphtalene diimide" or "NDI" or naphtalene diimide-based material", as used herein, refers to a molecule based on 1,4,5,8-naphthalenediimides structures.

The term "thiophene material" or "thiophene-based material", as used herein, refers to a molecule in which at least a thiophene or a thiophene derivative is present in the molecular structure.

The term "selenophene material" or "selenophene-based material", as used herein, refers to a molecule in which at least a selenophene or a selenophene derivative is present in the molecular structure.

The term "anthracene material" or "anthracene-based material", as used herein, refers to a molecule containing at least an anthracene molecule in the molecular structure.

The term "zinc complex material", "zinc coordination complex" or "zinc coordination complex-based material", as used herein, refers to a molecule containing a zinc atom coordinated to a bidentate ligand being an nitrogen containing heterocycle.

The term "absorption in the visible wavelength range" or "molecule exhibiting absorption in the visible wavelength range", as used herein, is meant to refer to a molecule/dye that is able to absorb light in only one or several parts of the entire range indicated or over the total range. For example a molecule may only absorb in the range of from 500-700 nm, whereas another molecule may absorb in the range of from 400-700 nm or 500-600 nm, whereas a third molecule may absorb over the range of from 400-500 nm (or the above described sub-ranges of preferably 400 nm to 500 nm, or 500 nm to 600 nm, or 600 nm to 700 nm). All these scenarios are meant to be encompassed by such wording.

The term "narrow absorption band", as used herein, is meant to refer to/means that the width of the absorption band at 0 intensity is 200 nm, more preferably 150 nm, more preferably 100 nm.

The term "transparent" or "transparent material", as used herein, refers to a material having an absorption coefficient of less than about 60,000 cm$^{-1}$ or an extinction coefficient of less than about 60,000 M$^{-1}$ cm$^{-1}$ (in toluene) in the visible wavelength range (about 400 to about 700 nm).

The term "colored" or "colored material", as used herein, refers to a material having an absorption coefficient of more than about 60,000 cm$^{-1}$ in the visible wavelength range with blue, green or red maximum, in particular in the region from about 400 nm to about 700 nm (with maxima anywhere in this region or absorbing everywhere in this region).

In accordance with the present disclosure, the term "electrode" refers to an electrical lead to apply voltage. An electrode may be "interdigitated", meaning that it has a comb-like shape with two combs lying opposite each other and the respective figures of the combs engaging with each other. Alternatively, an electrode may be a non-interdigitated. An electrode may be transparent or non-transparent. A transparent electrode may, for example, be formed from indium tin oxide (ITO) or from fluorinated tin oxide (FTO). A non-transparent electrode may be reflective and may, for example, be formed from silver (Ag) or gold (Au).

The requirements of a photoelectric conversion layer to be used in image sensors are demanding and can be summarised as followed:
  (i) narrow absorption band of at least one active material;
  (ii) high extinction coefficient, $\varepsilon > 10^4$ L mol$^{-1}$ cm$^{-1}$— correspondingly high absorption coefficient of at least one active material;
  (iii) heat resistant;
  (iv) high photoelectric conversion efficiency (EQE);
  (v) high-speed responsivity/high charge carrier mobility;

(vi) low dark-current in device;
(vii) thin film by thermal vapour deposition (Tvp<Tdec).

The present inventors have found—for the use as active materials for the organic photoconversion unit—material of specific structure which no or very low absoption in the visible range (400 to 650 nm), belonging to the following different families:

Naphtalene Mono Imides (NMI),
Naphtalene dimides (NDI) and
Dimers of this two previous type of molecules (NMI-NMI, NDI-NDI or NMI-NDI),
Thiophene-based materials
Anthracene-based materials
Zinc coordination complexes.

Said materials are used in a bulk heterojucntion (mixed p-n layer) or PN heterojunction (formed between a p layer and n layer or PiN junction (p layer—mixed layer as p-n bulk heterojunction—n-layer) in the photoelectric conversion material layer together with a material that absorbs in the visible range.

The materials of the present disclosure can be used as active materials for the organic photoconversion unit.

The organic photoconversion unit can be used in combination with a Si based photoelectrical conversion unit where different layer absorbed different colour (BGR) in a hybrid Silicon-organic image sensor or can be used without Si based photoelectrical conversion unit. In this case the organic photoconversion unit having the capability of absorbing different colour (BGR).

Figure 2:
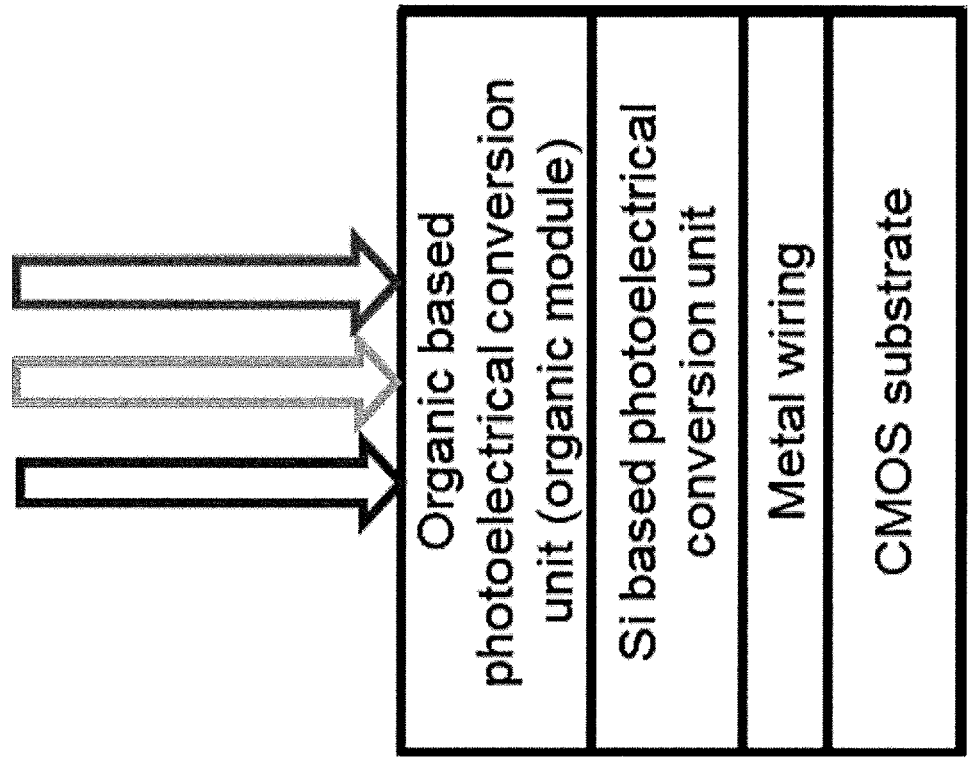
FIG. 2 shows a schematic representation of the hybrid silicon-organic image sensor.
Figure 3:
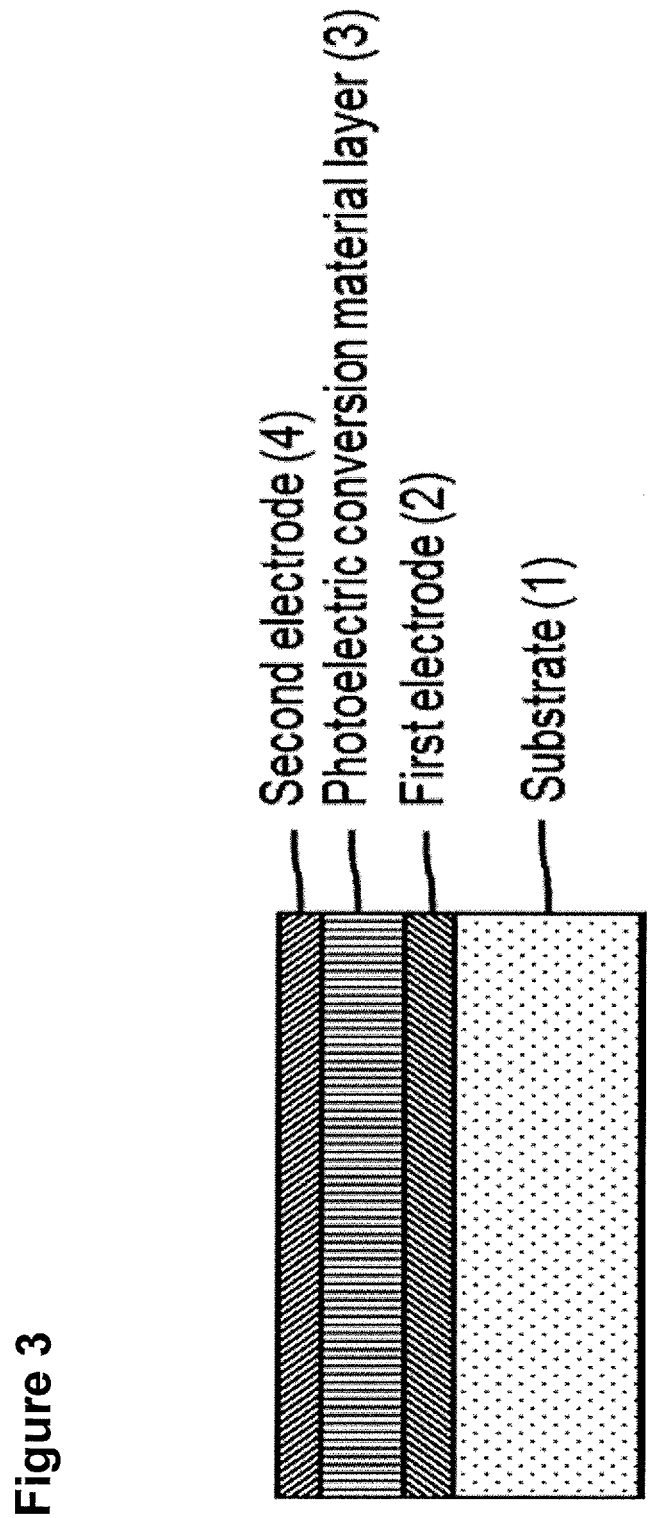
FIG. 3 shows a schematic representation of the organic based photoelectrical conversion unit with the different layers.

The general structure of the resulting hybrid image sensor device as well as the details of the organic based photoelectrical conversion unit are schematic represented in the FIGS. 2 and 3.

The present inventors have found a transparent N or a transparent P material (transparent=400 nm to 700 nm absorption coefficient of films <60000 cm$^{-1}$ or extinction coefficient (in toluene)<60,000 M$^{-1}$ cm$^{-1}$) and which in devices with P:N (generally P1:P2:N1:N2) heterojunctions can:

If N—dissociate efficiently the excitons created on the coloured (coloured=absorption coefficient in Vis is >60 000 in the VIS region with blue, green or red maximum) P (or the mixture of coloured P materials) or of another coloured N (or mixture of coloured N materials) via the process of LUMO dissociation—accepting electron from the excited state of the donor (the P material(s) or the N material(s) absorbing photons))

Figure 4:
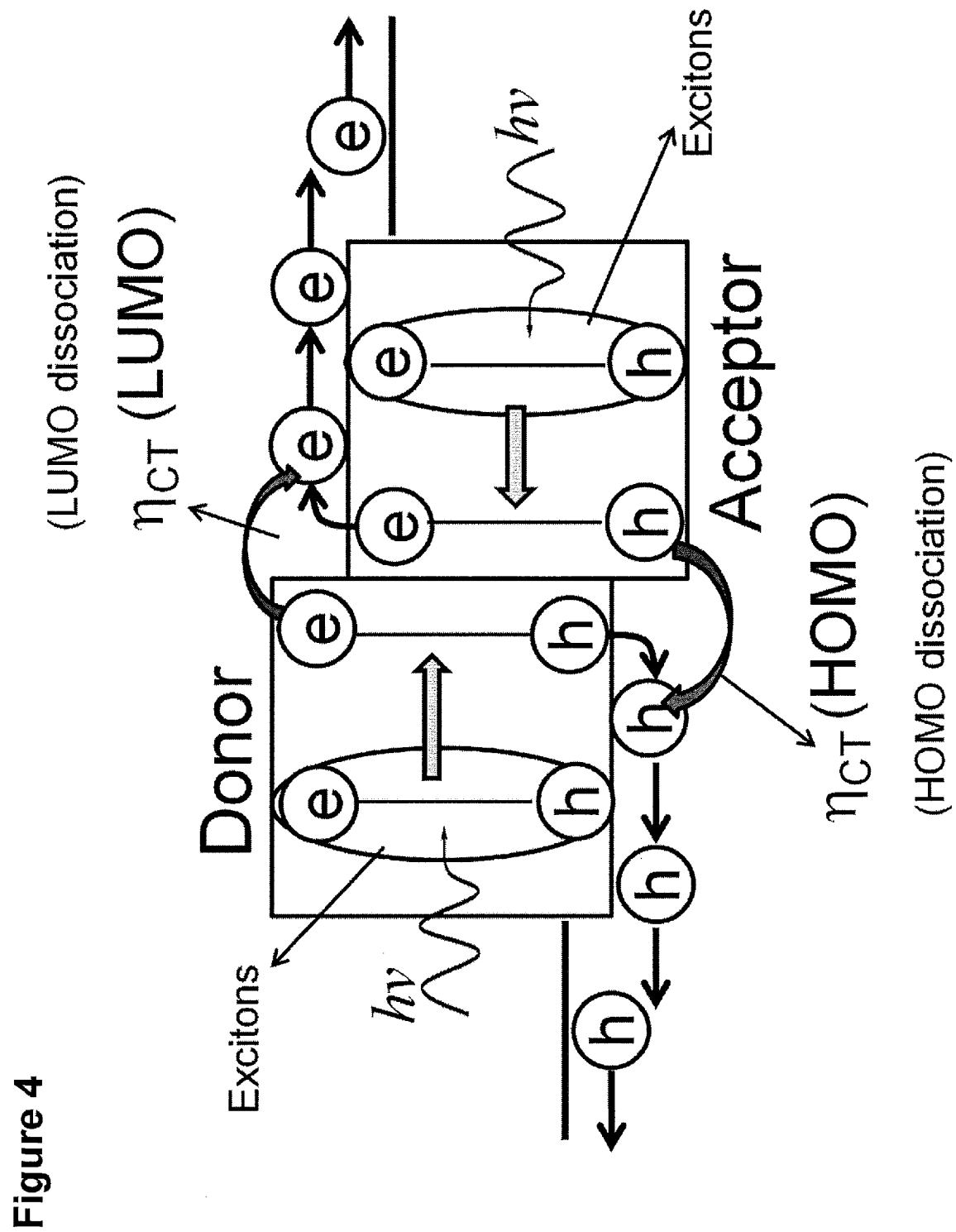
FIG. 4 describes the HOMO and LUMO dissociation process.

If P—dissociate efficiently the excitons created on the coloured (coloured=absorption coefficient in VIS is >60 000 in the VIS region with blue, green or red maximum) N (or the mixture of coloured N materials) or of another coloured P (or mixture of coloured P materials) via the process of HOMO dissociation—donating electron into the HOMO of the excited coloured material (the P material(s) or the N material(s) absorbing photons)) which is equivalent to accepting a hole from them For example, in a P:N example the P material is the donor and the N material the Acceptor (as e.g. shown in FIG. 4). In an embodiment, where P1:P2:N1:N2: one of the N materials could be a Donor as well one of the P materials could be an acceptor Dissociation/charge transfer efficiency (ηCT) general description:
ηCT has ηCT(HOMO) and ηCT(LUMO) parts
In FIG. 4 (as example)

The Acceptor is the N material accepting an electron—either in its LUMO (transparent N) with $r_1$CT(LUMO) or in its HOMO (transparent P) state with ηCT(HOMO) (this last one is equivalent to hole transferred to the donor);

The Donor is the material donating an electron—from its LUMO (when in excited state=colored P) or from its HOMO (transparent P);

For transparent N—the ηCT(LUMO) has to be high;
For transparent P—the ηCT(HOMO) has to be high.

The main advantages of the transparent n and/or p materials of the present disclosure, in particular for the application in photoelectrical conversion layers and devices are as follows:

1. The possibility to adjust the absorption spectrum of the active device via adjusting the absorption spectrum of only one active component. This will be the spectrum of the partner material—the p partner material absorption when using transparent n materials and n partner material absorption when using transparent p materials.
2. Possibility for tuning the electron mobility only in transparent n materials and the hole mobility only of transparent p materials
3. HOMO or LUMO level tuning (together with ensuring large band gap for high transparency in the visible range.
4. Possibility for optimising one exciton dissociation/charge generation efficiency only—either through the LUMO (for transparent n) or through the HOMO (for transparent p materials (see FIG. 4).

The main advantages of the new n and p materials without absorption or with a very low absorption in the visible wavelengths (400-700 nm) as active materials for the application in photoelectrical conversion layers are as follows:

excellent photostability—especially due to UV absorption only;
possibility for tuning of the absorbtion spectrum of the device via the absorption of the partner (the other) active component—i.e. the absorption spectrum of p material in case of transparent n and the absorption of n material in case of transparent p;
easy alteration of HOMO and LUMO energy levels;
high theinial stability (300 to 500° C. depending on substituents but at least 300° C.);
high electrons (for n) and/or holes (for p) mobilities—especially the independent tuning of mobilities—e.g. only high electrones mobility for transparent n material is needed;
high exciton dissociation ability—to allow for photoconversion devices with high EQE;
high charge generation efficiencies of the devices—high charge transfer efficiency and charge separation efficiency;
especially independent tuning of the charge generation efficiency—through the LUMO (for transparent n) and through the HOMO (for transparent p);
can be used as n-buffer or p-buffer layers correspondingly—allows for further device optimisation via possible tuning of morphology of the active layer and/or energy level alignment through the device.

The main advantages of the naphtalene monoimide (NMI) and naphtalene diimide (NDI) as well as the dimer combinations of this naphtalene based molecules for the application in photoelectrical conversion layers are as follows:

exhibit excellent photo- and thermal stability (300 to 500°);
easy alteration of HOMO and LUMO energies is possible;

very low extinction coefficients in the visible range;
high electron mobilities;
in case of dimers:
3D structure and LUMO degeneration which increases dissociation efficiency (LUMO dissociation);
higher electron mobilities;
give possibility for highly efficient LUMO based dissociation of the excitons formed in the absorbing p partner.

The energy levels and the morphology in thin film are tunable by the type of substituents R, $R_1$ and bridge. This makes the naphtalene monoimide (NMI) and naphtalene diimide (ND) as well as the dimer combinations of this naphtalene based molecules very versatile molecules to be used in the organic photoelectric conversion layer in combination with a material that absorbs in the visible range.

The main advantages of the transparent thiophene based molecules for the application in photoelectrical conversion layers are as follows:
exhibit good photo- and thermal stability (until 300° C.);
easy alteration of HOMO and LUMO energies is possible;
very low extinction coefficients in the visible range;
high hole mobilities:
give possibility for highly efficient HOMO based dissociation of the excitons foiitied in the absorbing n partner;
in case of dimers:
3D structure and HOMO degeneration which increases dissociation efficiency (HOMO dissociation);
higher hole mobilities.

The energy levels and the morphology in thin film are tunable by the type of substituents R, $R_1$, $R_2$ as well as the heteroatoms in the core structure. This makes the thiophene based molecules very versatile molecules to be used in the organic photoelectric conversion layer in combination with a material that absorbs in the visible range.

The main advantages of the anthracene based molecules for the application in photoelectrical conversion layers are as follows:
exhibit good photostabilty
and thermal stability (until 300° C.)
easy alteration of HOMO and LUMO energies is possible;
very low extinction coefficients in the visible range;
high hole mobilities;
give possibility for highly efficient HOMO based dissociation of the excitons formed in the absorbing n partner;
they are dimers:
3D structure and HOMO degeneration which increases dissociation efficiency (HOMO dissociation);
higher hole mobilities.

The main advantages of the zinc complex molecules for the application in photoelectrical conversion layers are as follows:
exhibit good photo- and thermal stability (until 350° C.);
alteration of HOMO and LUMO energies is possible;
extremely low extinction coefficients in the visible range;
high electrons and hole mobilities possible—tuning required;
3D structure—expected to support high exciton dissociation efficiencies.

According to the present disclosure, when one of the active materials is transparent this offers the following possibilities for respective devices and so on:
Tuning overall absorption spectrum via tuning absorption of one active material only;
Tuning of exciton diffusion efficiencies of the partner (absorbing) material only;
Tuning of charge generation efficiencies through HOMO or LUMO independently;
Tuning of only electron (for transparent n) or only hole (transparent p) mobility;
Generally: decoupling of absorption properties in the visible range from electron/hole transfer and transport properties.

EXAMPLES

Example 1: Naphtalene Mono Imide (NMI)-Based Material

Figure 5:
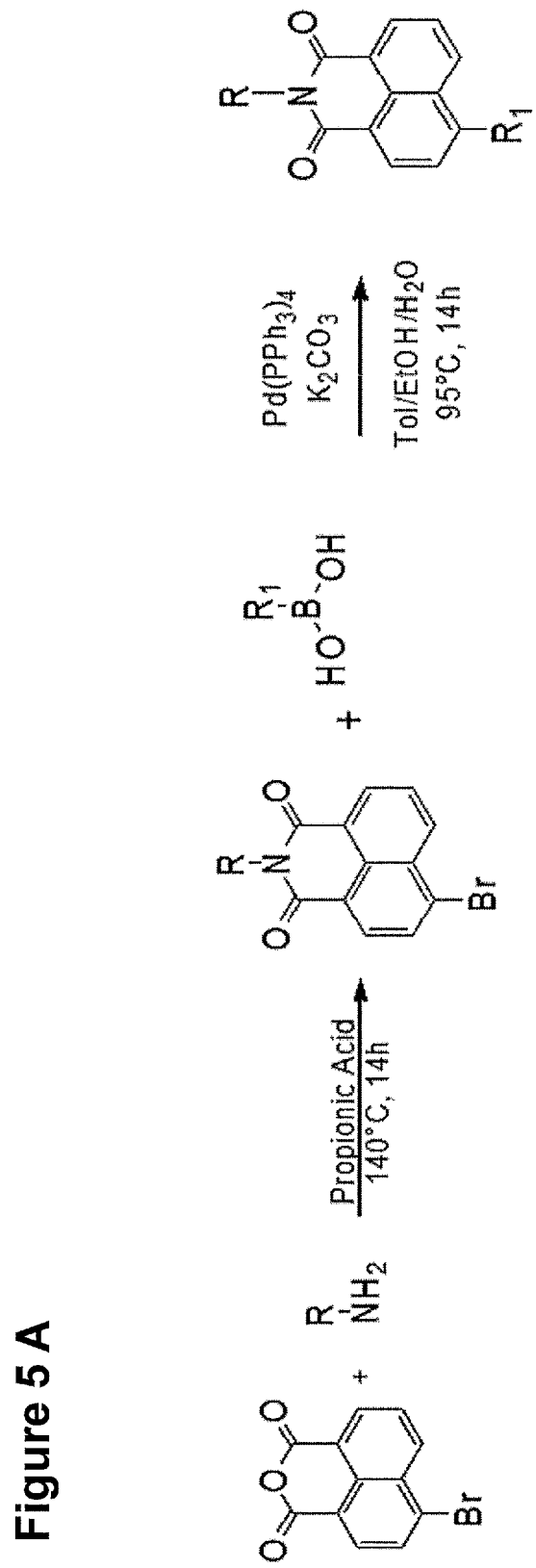
FIG. 5A shows the general synthetic route for naphthalene monoimide (NMI)-based materials.
FIG. 5B shows compound NMI1 of Example 1 and its TG, DSC and its absorption in solution.
Figure 5:
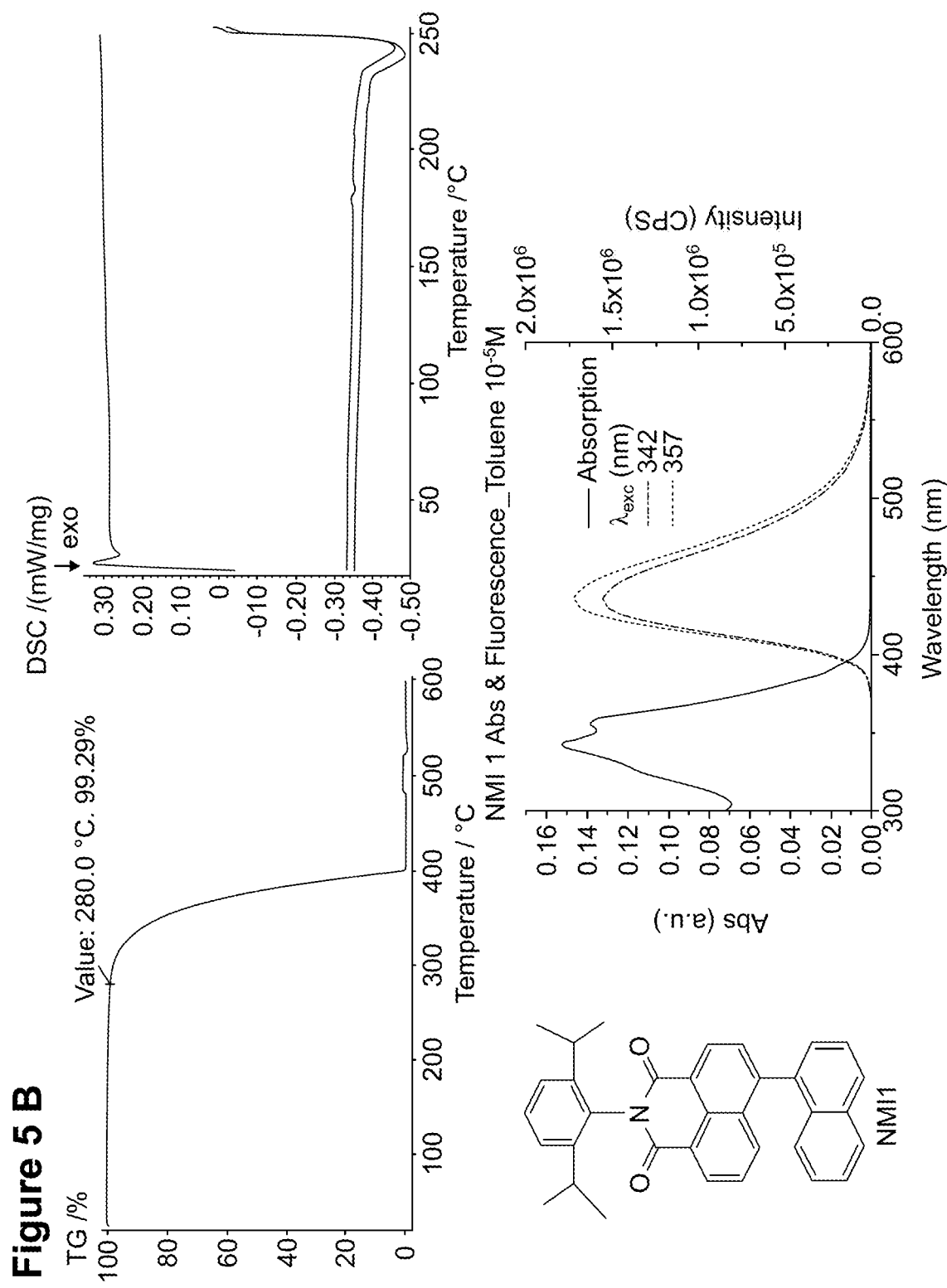

In the scheme shown in FIG. 5A, the general synthetic route for a naphthalene monoimide is reported.
Using this synthetic route several compounds have been synthesized, such as compound NMI1.

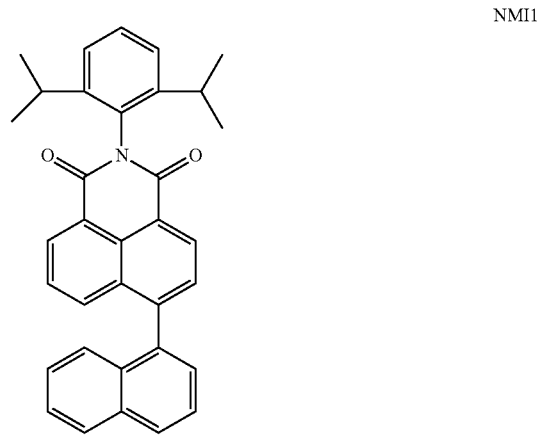 [SMILES: CC(C)c1cccc(C(C)C)c1N1C(=O)c2cccc3c(-c4cccc5ccccc45)ccc(c23)C1=O]

NMI1

NMI1 shows good thermal stability as it can be seen from the TG (T onset circa 280° C.), no crystallinity (DSC traces do not show melting and crystallization transitions) and no absorption in the visible range. See FIG. 5B.

The NMI1 derivate was used as n material in combination with quinacridone (QD) as p material (the absorbing partner) in the following configuration: ITO/QD:NMI1=70:30 (120 nm)/LiF(0.5 nm)/AlSiCu 100 nm/. The device gave an EQE at 550 nm of 28% @ 0V and 40% @ −1V. With device optimisation EQEs of up to 45% were achieved (FIG. 5C).

The electron mobility of this material is $1 \times 10^{-9}$ cm$^2$/Vs

Example 2: NMI Dimer-Based Materials

Figure 6:
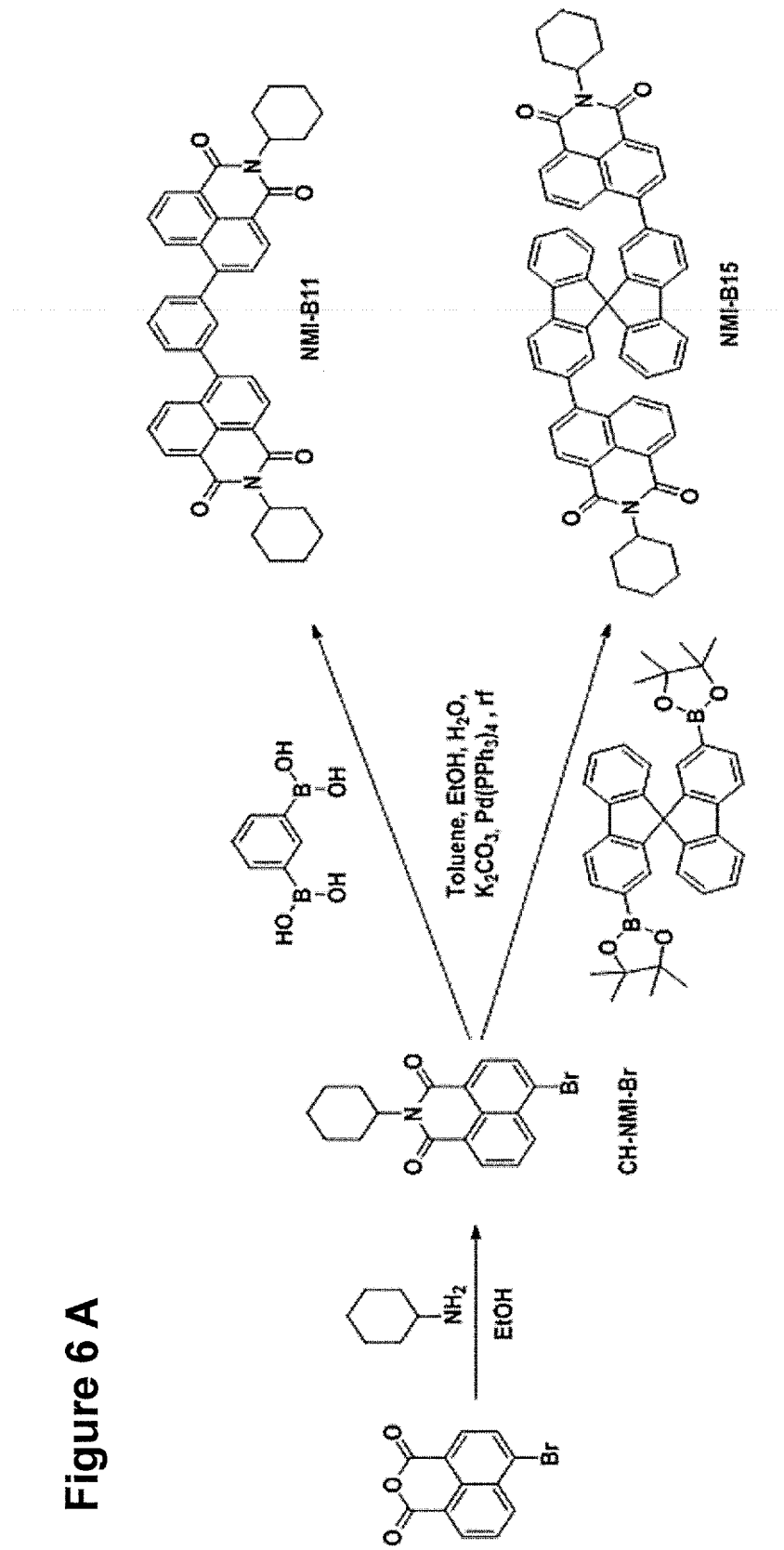
FIG. 6A shows the synthetic route for the prepartion of two naphtalene monoimide dimer (NMI dimer)-based materials, called NMI-B11 and NMI-B15.
FIG. 6B shows the TG and absorption in solution of both NMI-B11 and NMI-B15.
FIG. 6C shows the External Quantum Efficiency (EQE) of a photoelectric conversion layer wherein NMI-B11 was used as transparent n material in combination with quinacridone (QD) as absorbing p material.
Figure 6:
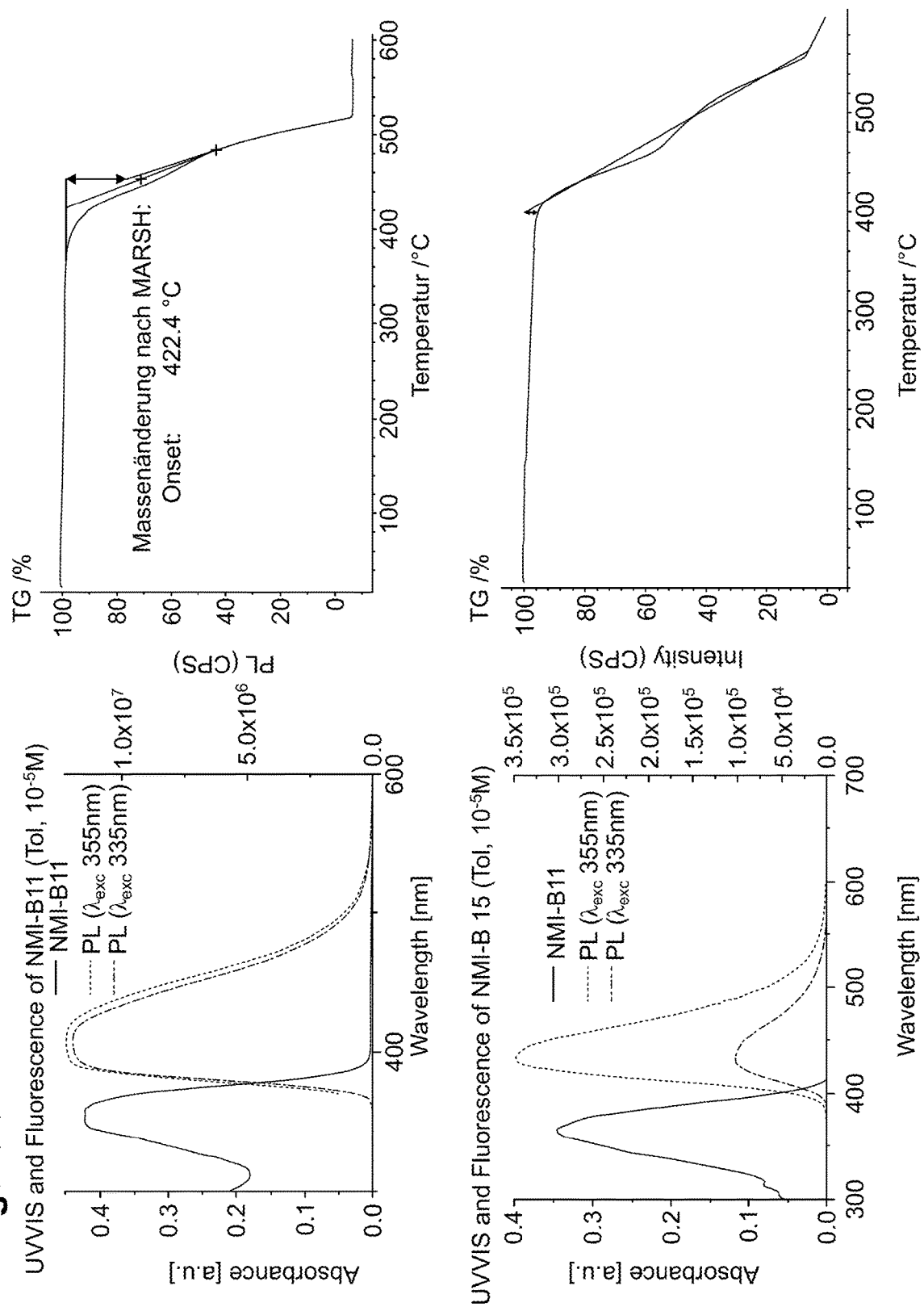
Figure 6:
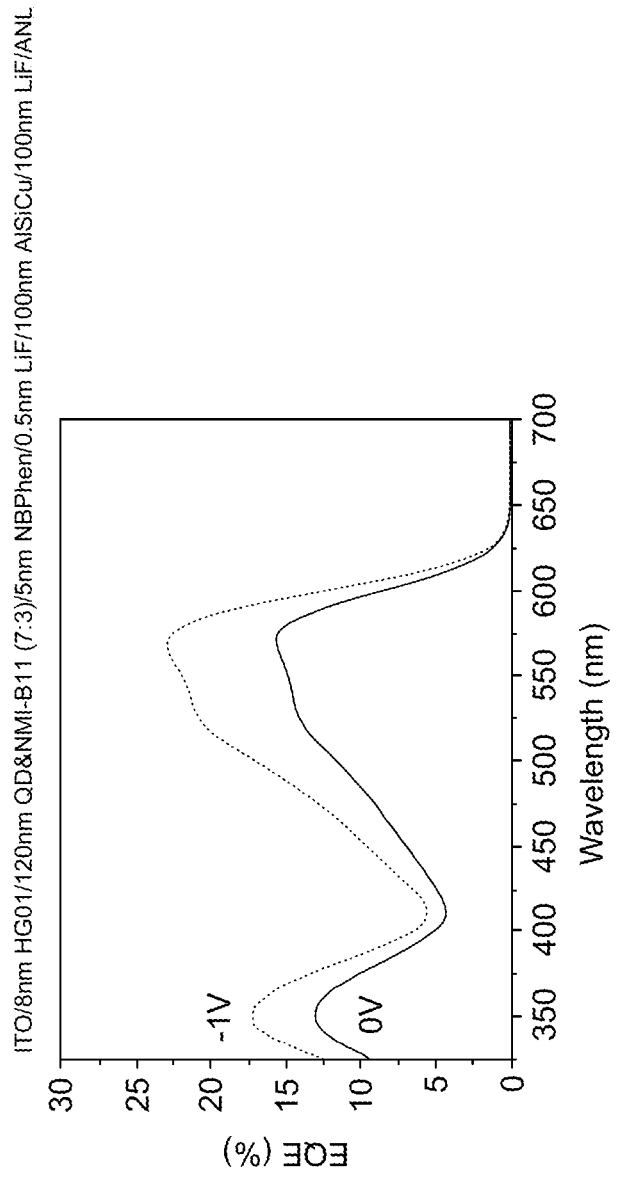

In the scheme shown in FIG. 6A, the synthetic route for the prepartion of the two different naphtalene monoimide dimers NMI-B11 and NMI-B15 is reported.

The two compounds shows both an excellent thermal stability as it can be seen from the TG ($T_{onset}$ circa 400° C.) and no absorption in the visible range. See FIG. 6B.

The NMI-B11 derivate was used as transparent n material in combination with quinacridone (QD) as absorbing p material in the following configuration: ITO/8 nm HG01/120 nm QD&NMI-B11 (7:3)/5 nm NBPhen/0.5 nm LiF/100 nm AlSiCu/100 nm LiF. The device gave an EQE at 550 nm of 15% @ 0V and 23% @ −1V (FIG. 6C). The charge transfer efficiency ηCT (−1V, 10 ns) is 95%. The electron mobility of this material is $3 \times 10^{-5}$ cm$^2$/Vs.

The improvement of the electron mobility of the NMI-dimers as compared to NMIs is for all synthesized and characterised molecules 2-4 orders of magnitude. For this reason all the NMI-dimers are suitable to be used as electron-buffer or electron transport layers.

Example 3: DTP-Based Materials

Figure 7:
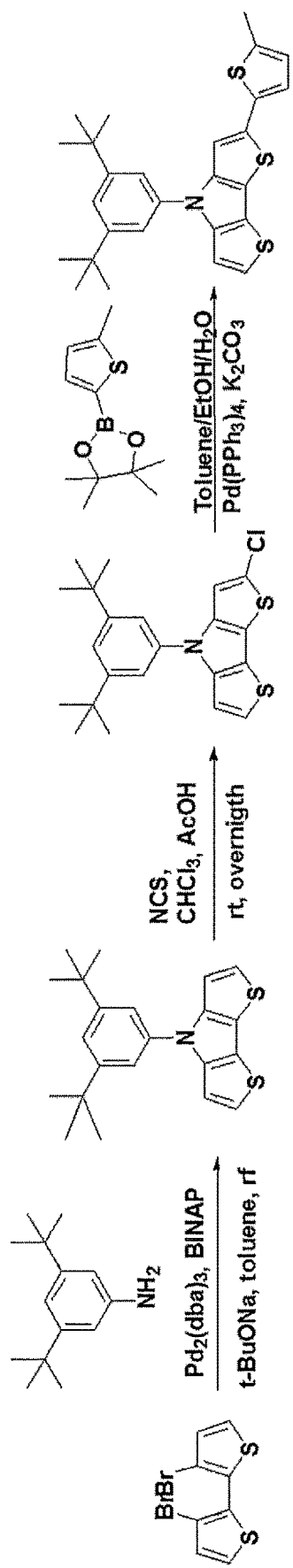
FIG. 7A shows the synthetic route for the prepartion of the dithioenopyrrol (DTP)-based material DTP6.
FIG. 7B shows DTP6's TG, DSC and its absorption in solution.
FIG. 7C shows the External Quantum Efficiency (EQE) of a photoelectric conversion layer wherein DTP6 was used as transparent n material (donor) in combination with Subphtalocyanineclhoride (SubPcCl) as absorbing p material (acceptor).
Figure 7:
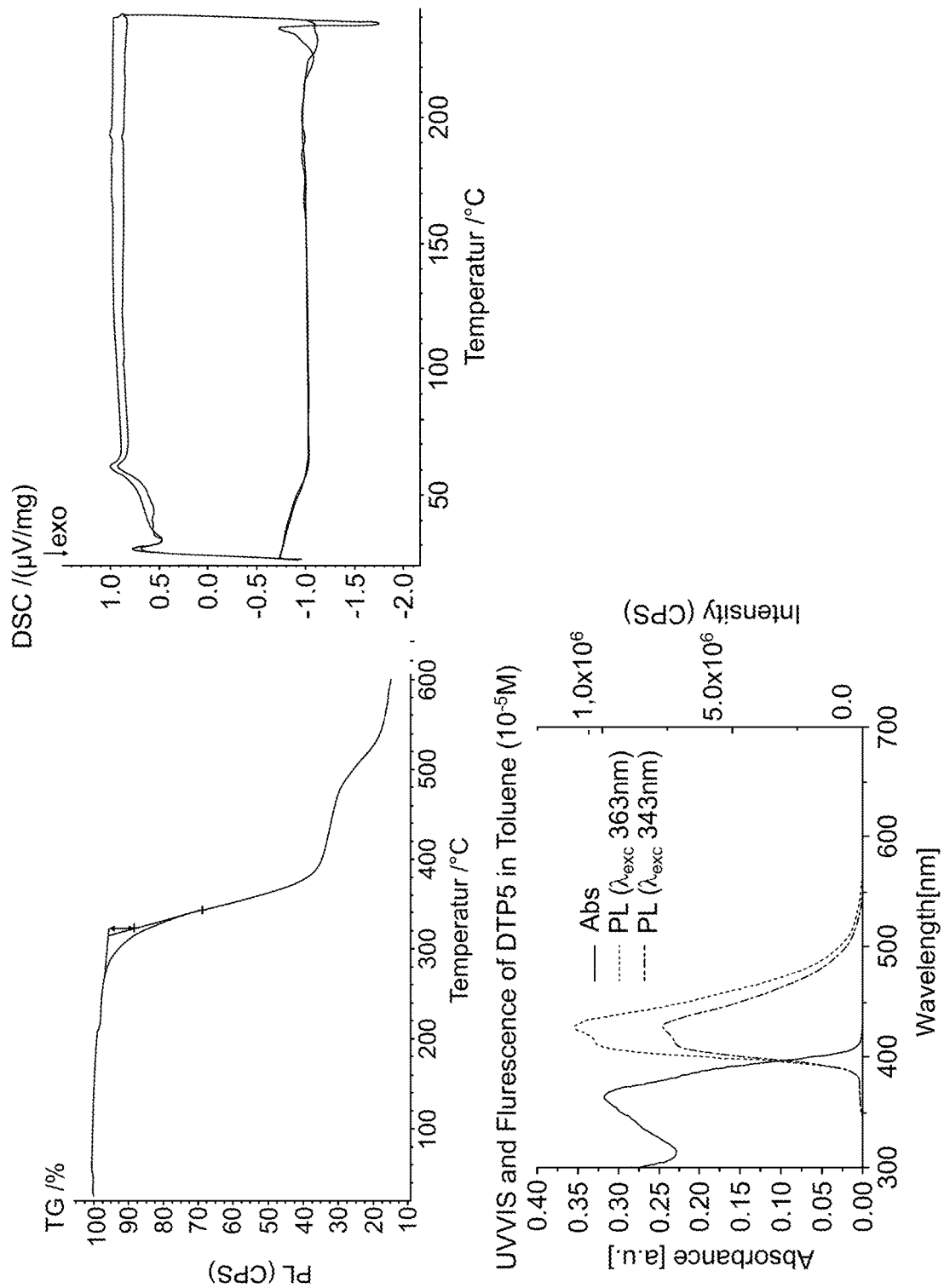
Figure 7:
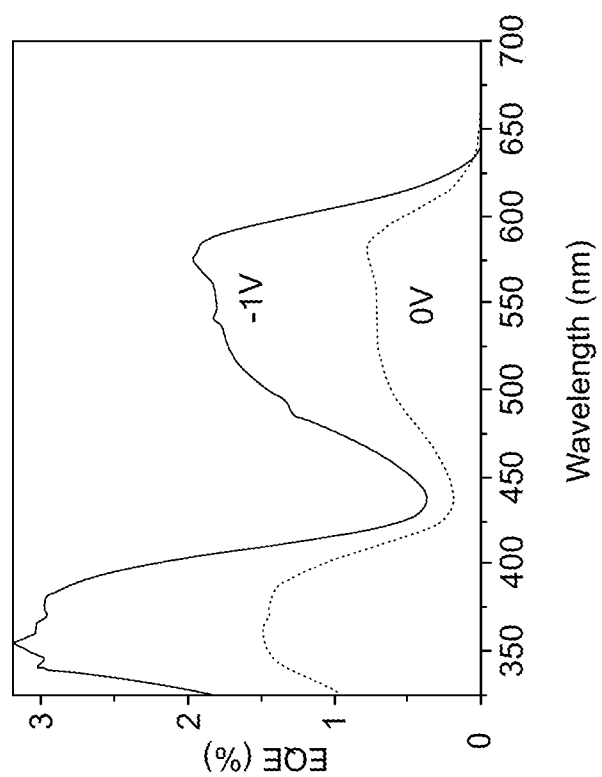

In the scheme shown in FIG. 7A, the synthetic route for the dithioenopyrrol (DTP)-based material DTP6 is reported.

The DTP6 as it can be seen from the TG ($T_{onset}$ circa 310° C.), no crystallinity (DSC traces do not show melting and crystallization transitions) and no absorption in the visible range. See FIG. 7B.

The DTP6 derivate was used as donar in combination with Subphtalocyanineclhoride (SubPcCl) as acceptor in the following configuration: ITO/8 nm alpha-NPD/120 nm DTP5&SubPcCl/5 nm NBPhen/100 nm AlSiCu/100 nm LiF. The device gave an EQE at 580 nm of 0.7% @ 0V and 2% @ -1V (FIG. 7C).

Example 4: Naphtalene Diimide (NDI)-Based Material

The naphtalene diimide (NDI) NDI1 has the following chemical structure:

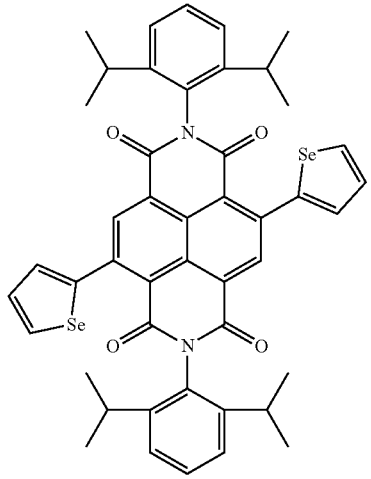

NDI 1

Chemical Formula: $C_{46}H_{42}N_2O_4Se_2$
Molecular Weight: 844.77

Figure 8A:
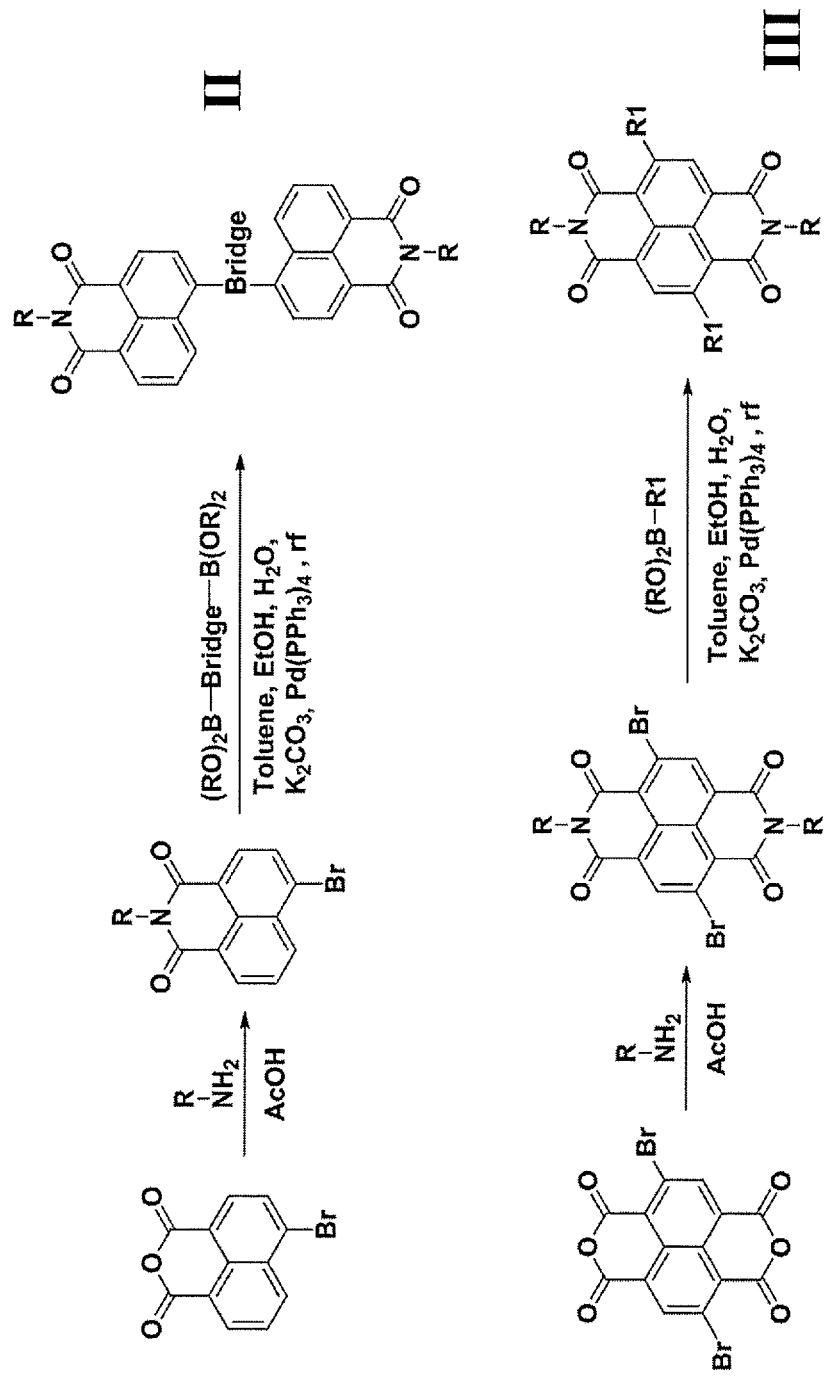
FIG. 8A shows the general synthetic route for naphtalene monoimide dimer (NMI dimer)-based materials (general foiniula II) and naphtalene diimide (NDI)-based materials (general formula III).
Figure 8:
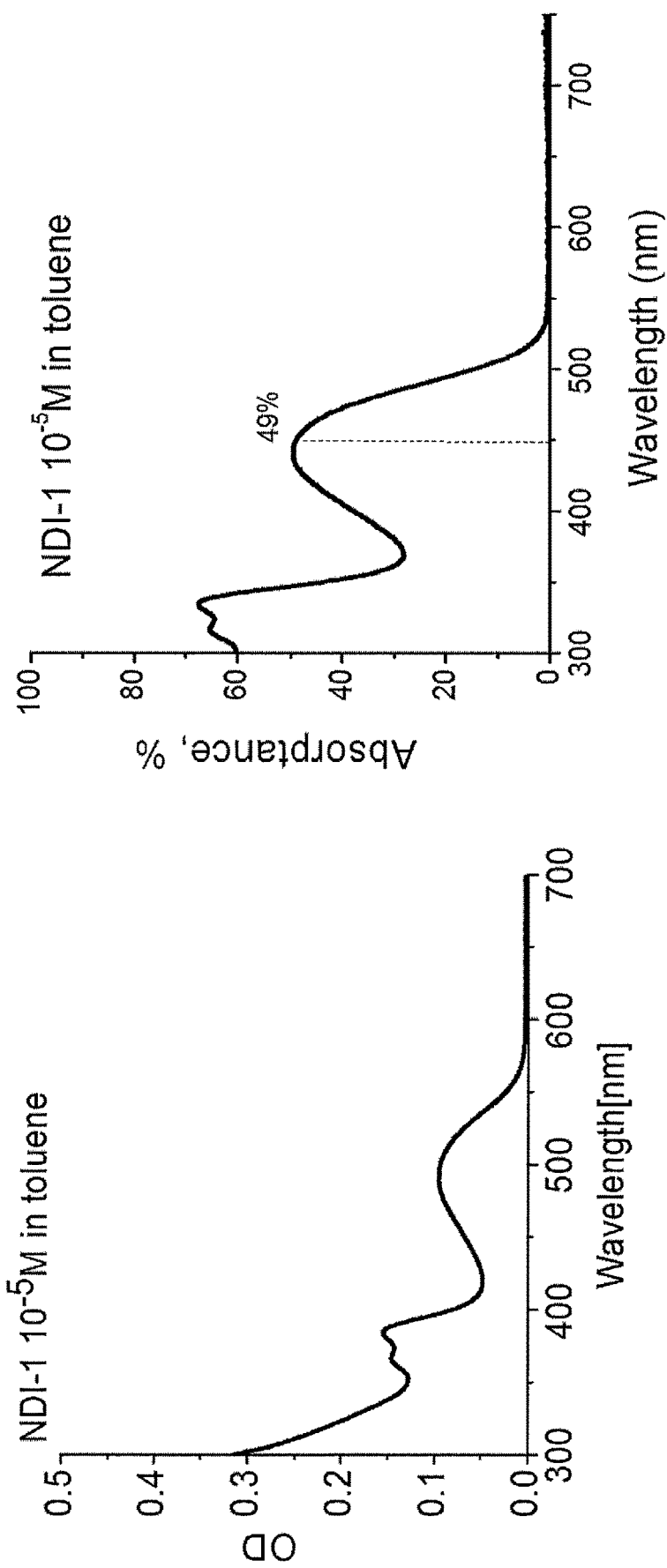
FIG. 8B shows UV VIS spectra of the naphthalene diimide-based material NDI1.
FIG. 8C shows electron mobilities of NDI1
FIG. 8D shows a PiN junction device of NDI1 with QD.
FIG. 8E shows a PIN junction device of NDI1 with BQD.
FIG. 8F shows a PiN junction device of NDI1 with SubPcCl and of NMI-NDI1 with SubPcCl.
Figure 8:
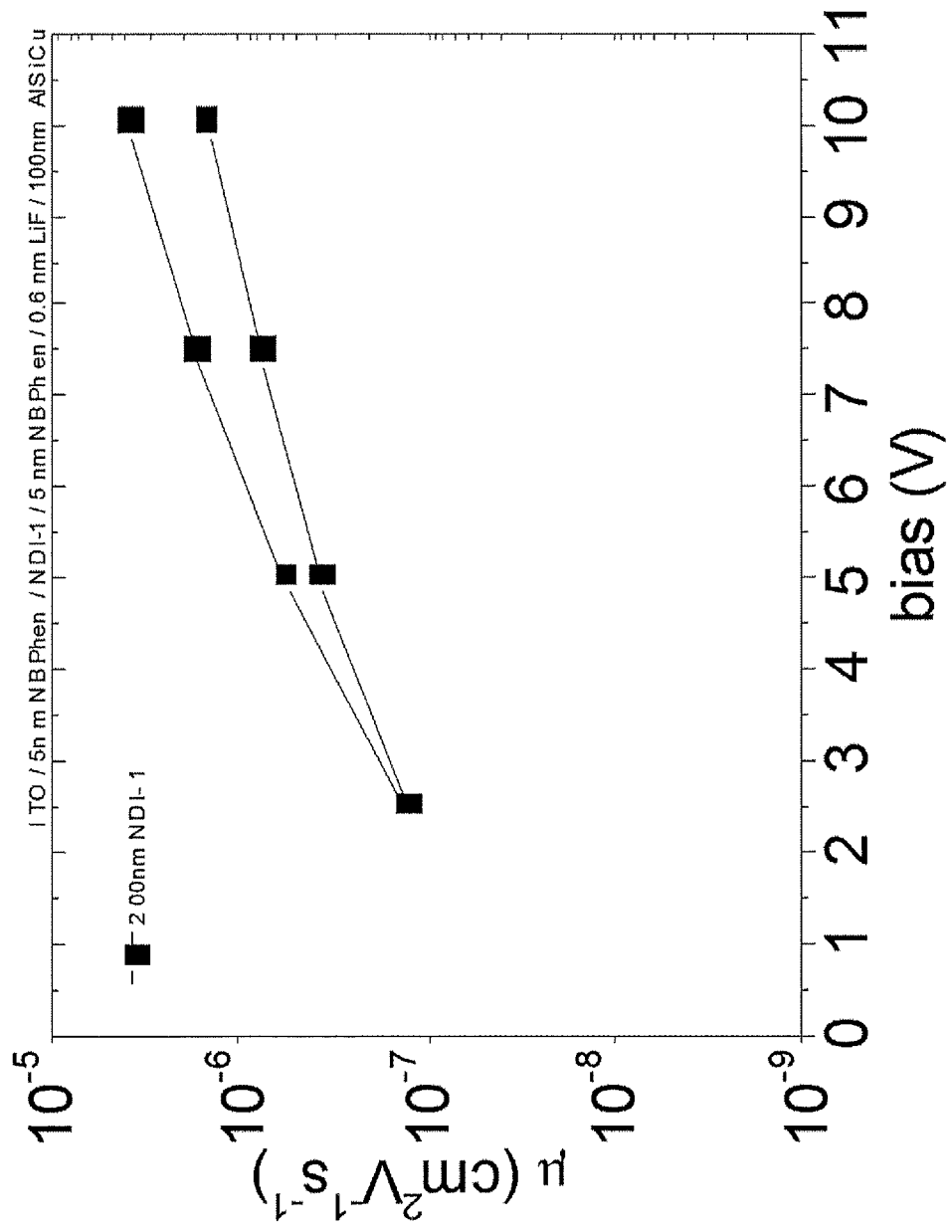
Figure 8:
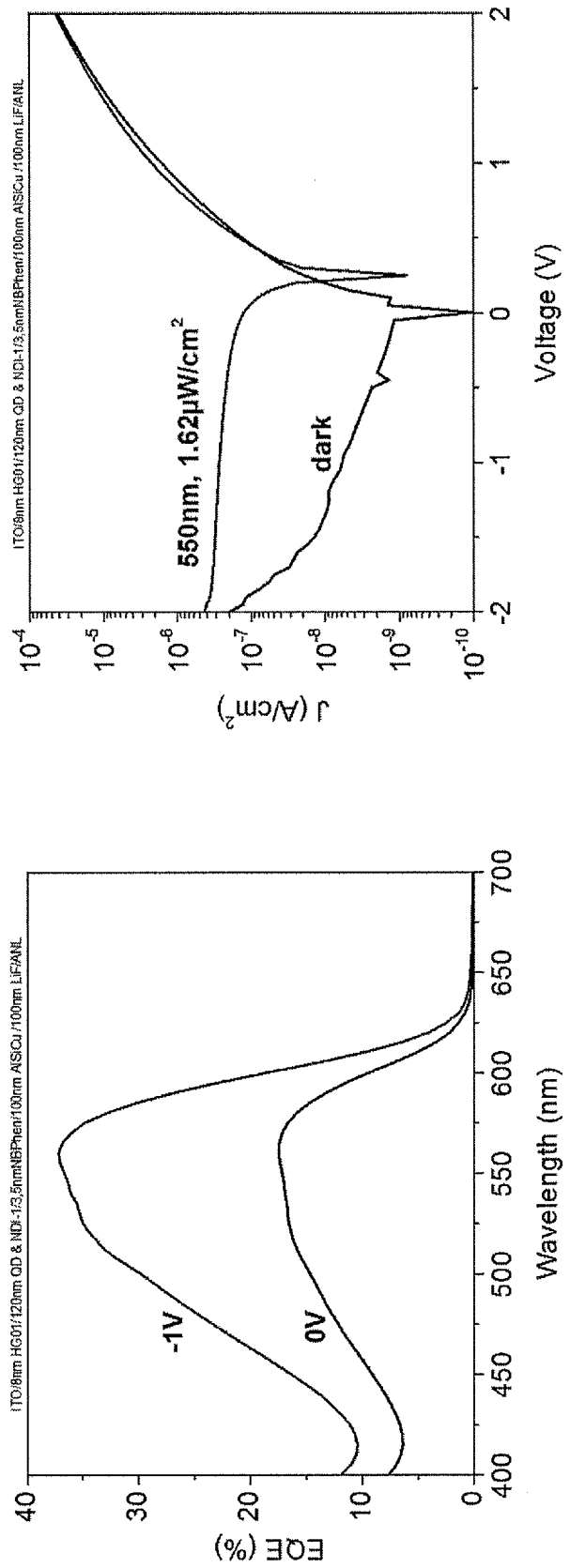
Figure 8:
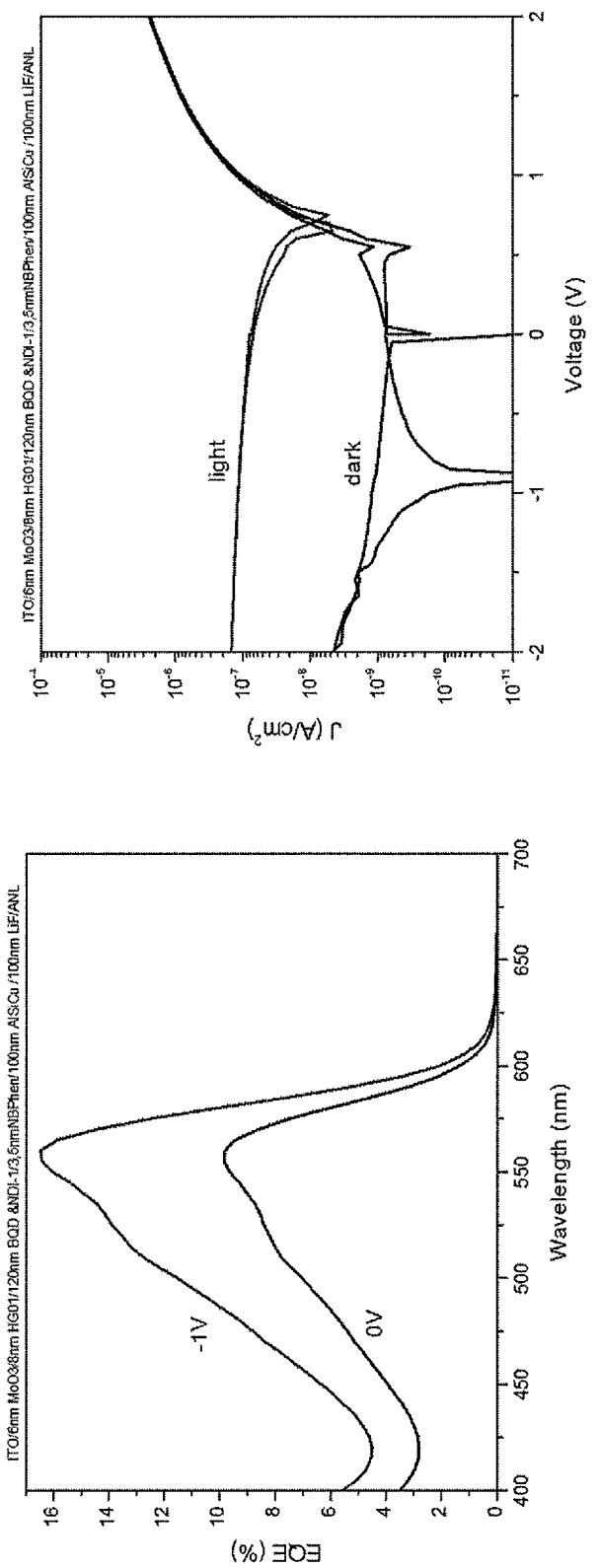
Figure 8:
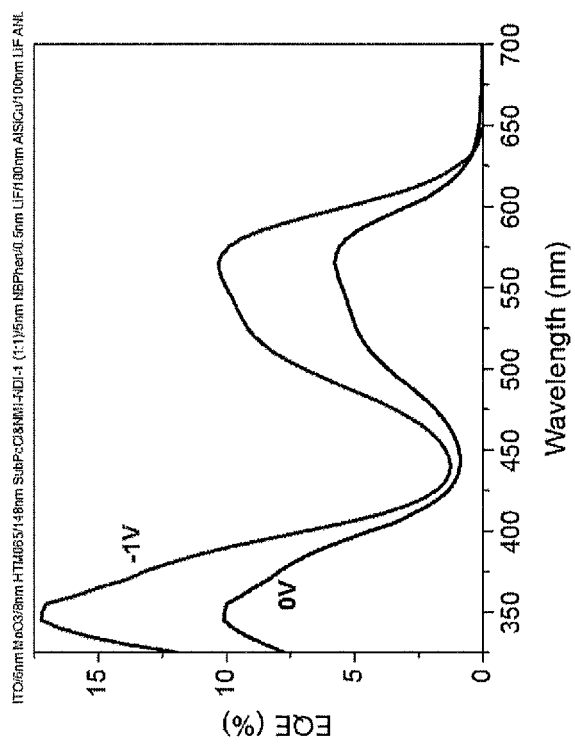
Figure 8:
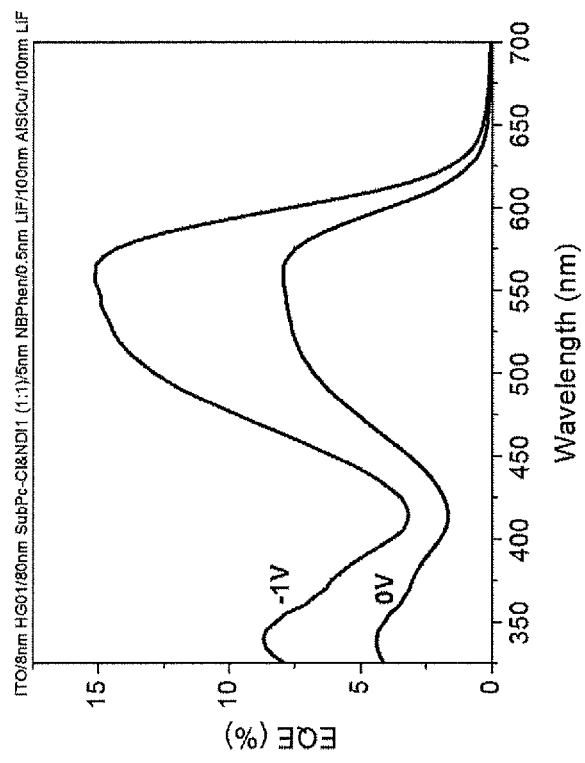
Figure 9:
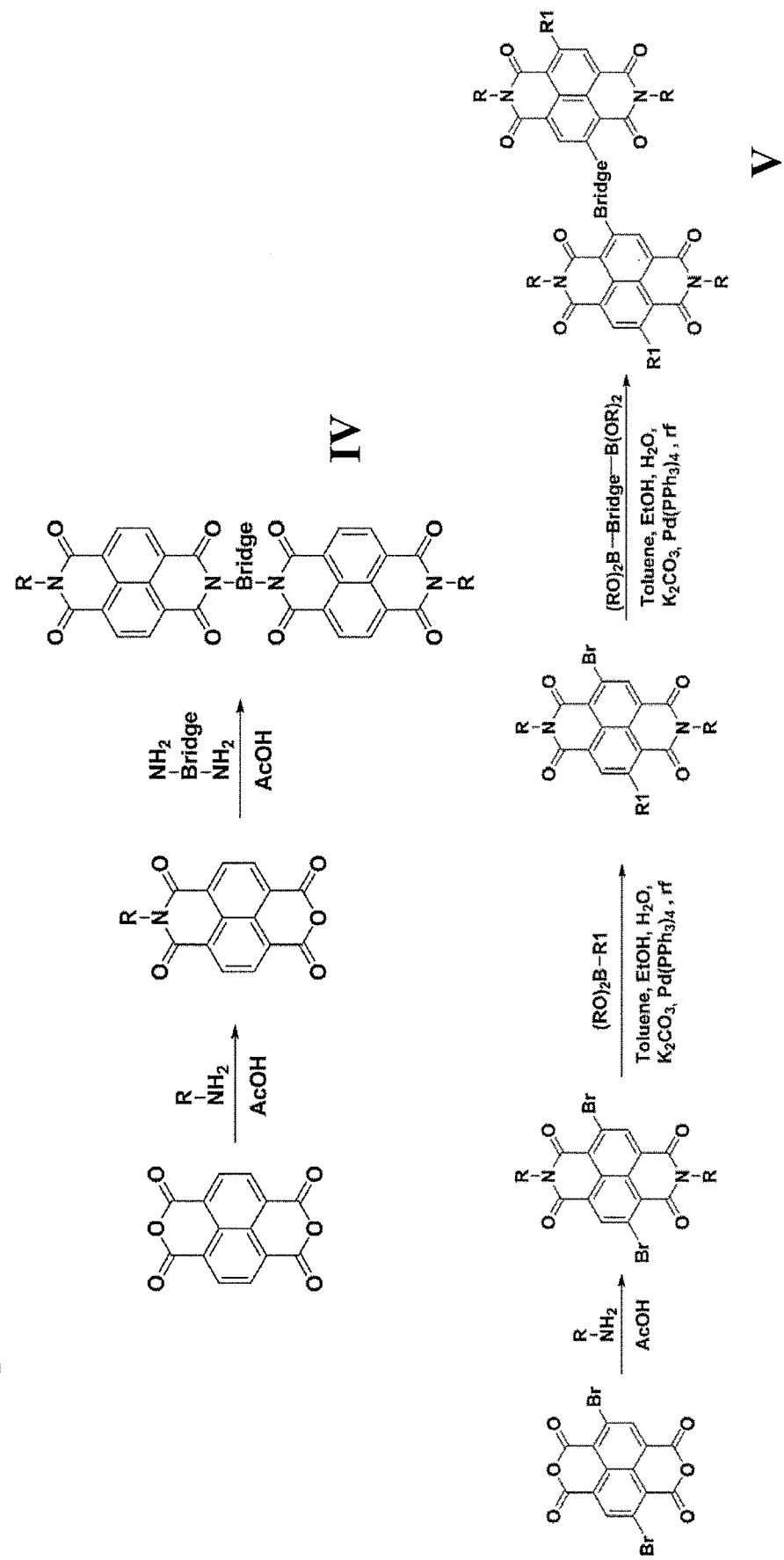
FIG. 9 shows the general synthetic route for naphtalene diimide dimer (NDI dimer)-based materials (general formulas IV and V).
Figure 10:
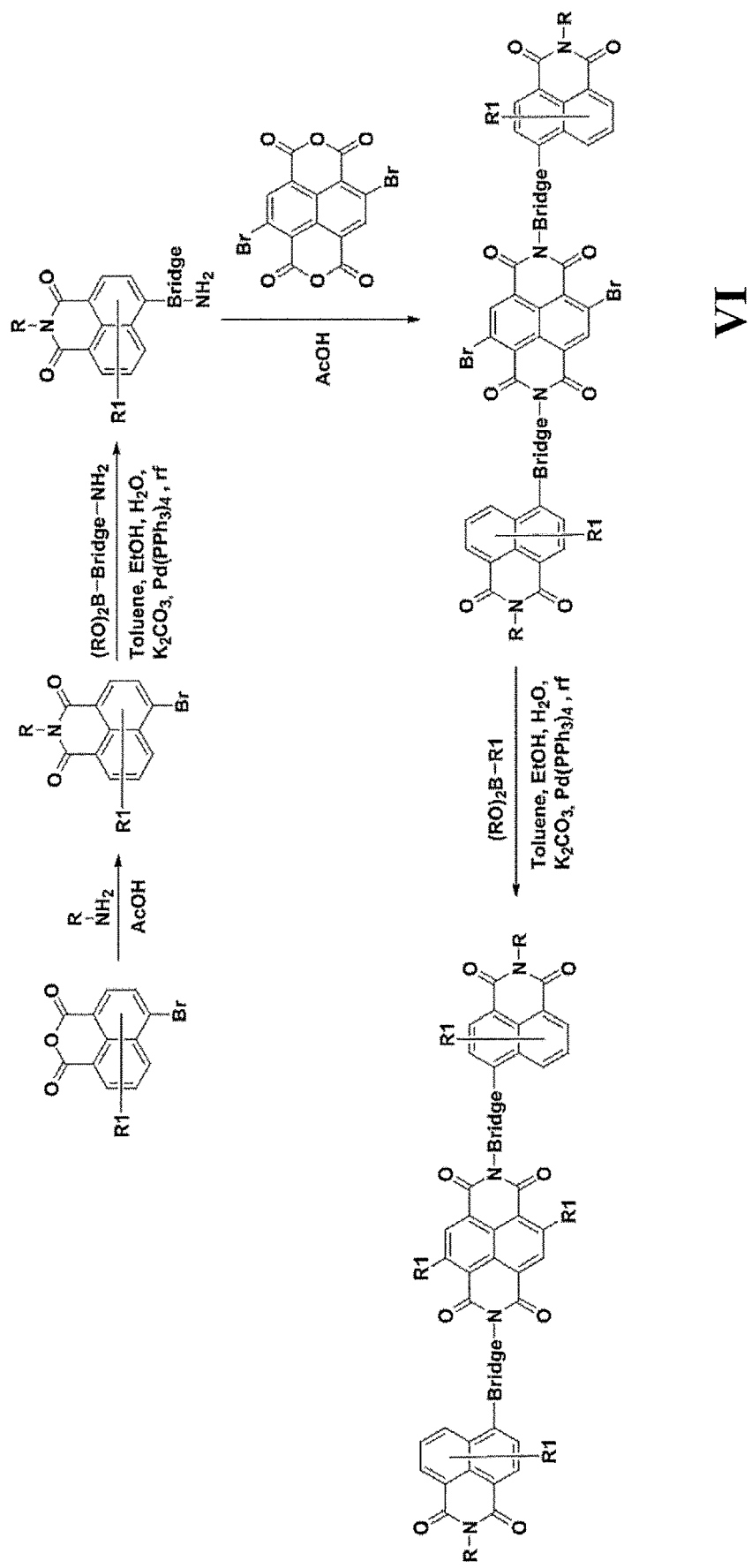
FIG. 10 shows the general synthetic route for naphtalene mono-diimide dimer (NMI-NDI)-based materials (general formula VI—FIG. 10A, general formula VII—FIG. 10B and general formula VIII—FIG. 10C).
Figure 10:
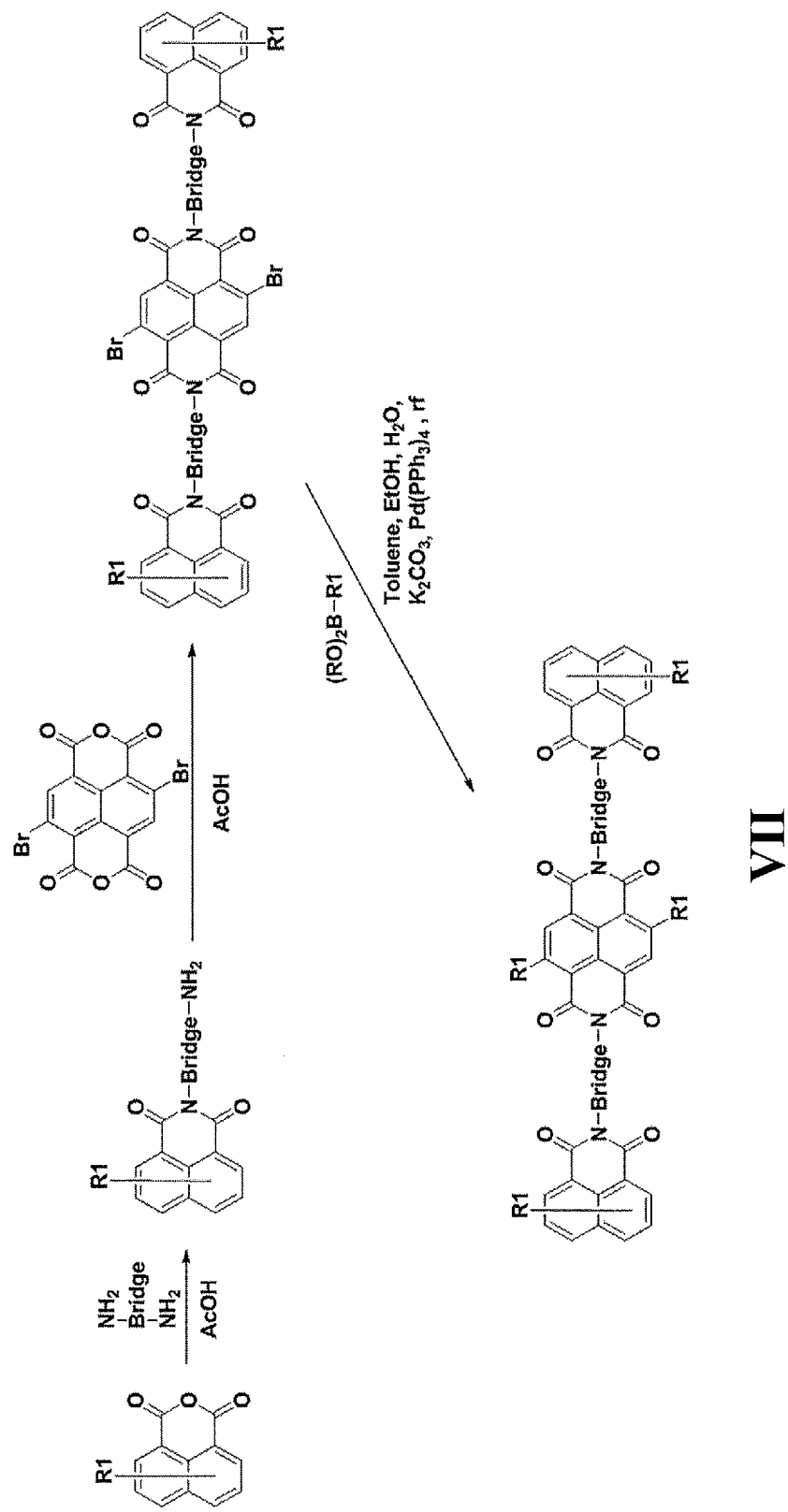
Figure 10:
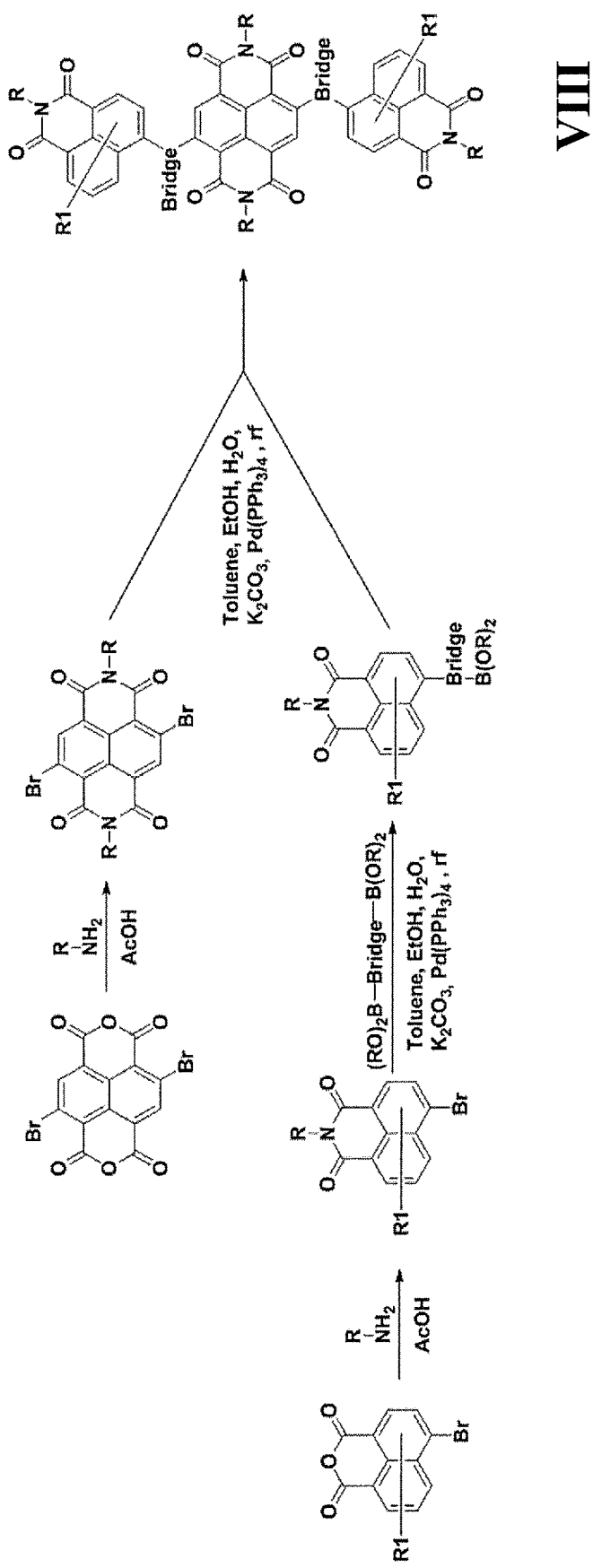
Figure 11:
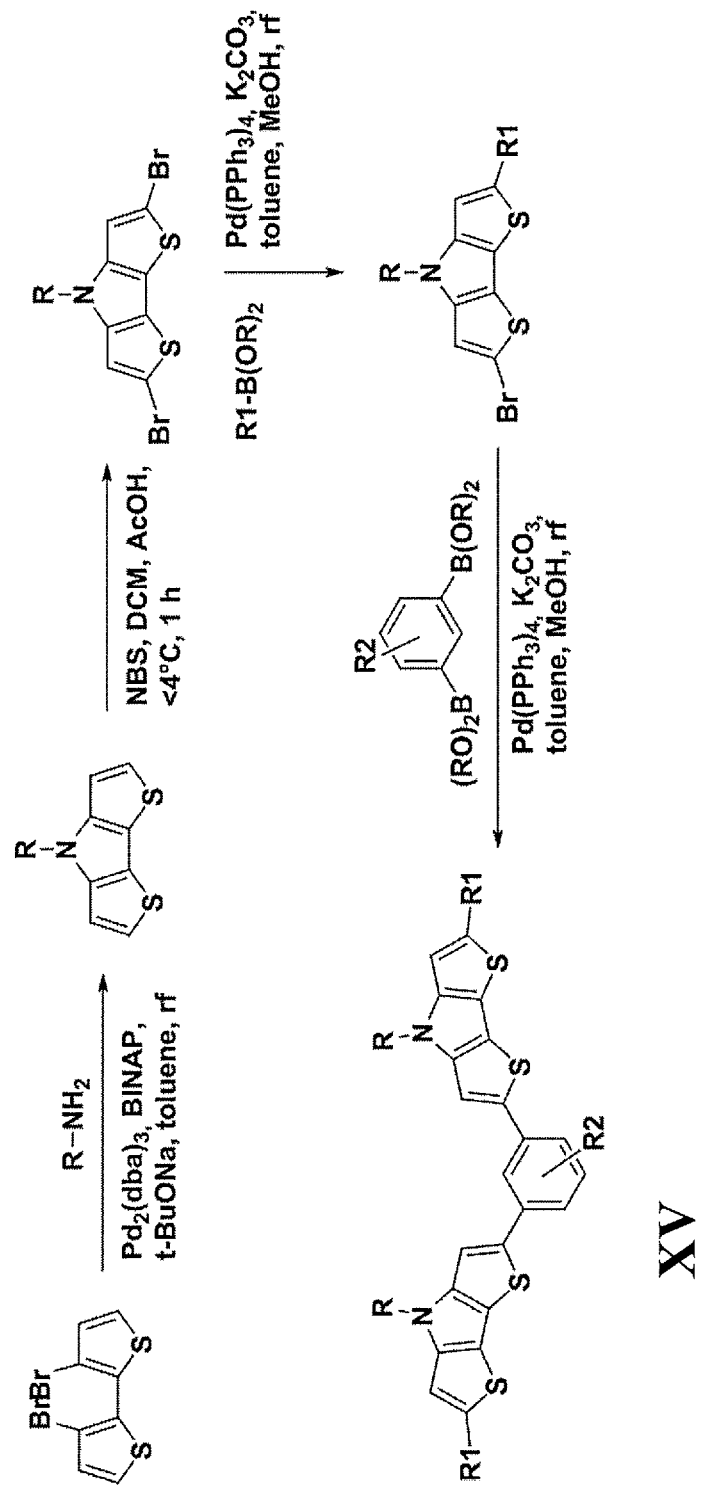
FIG. 11 shows the general synthetic route for dithioenopyrrol dimer (DTP dimer)-based materials (general formula XV—FIG. 11A and general formula XVI—FIG. 11B).
Figure 11:
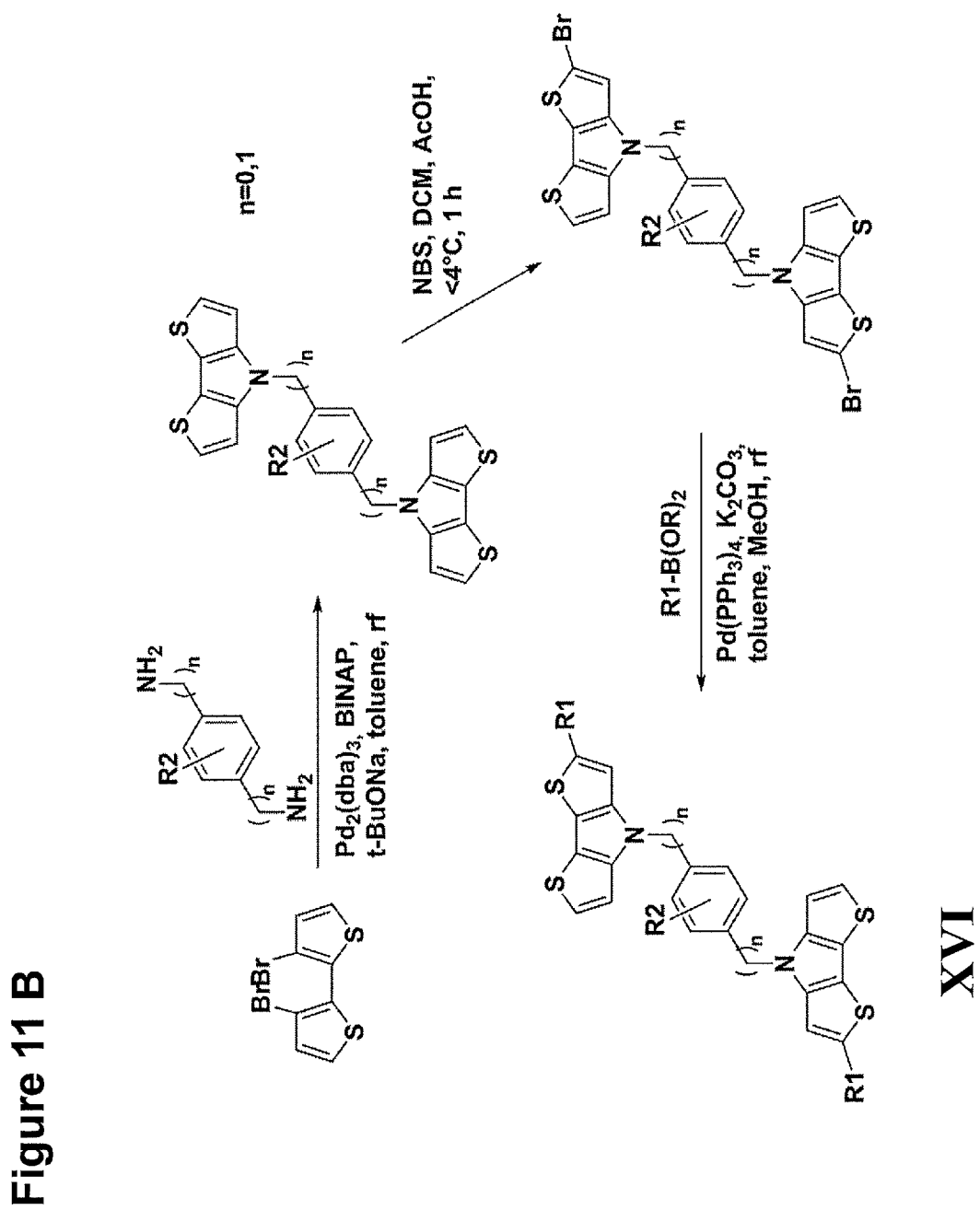
Figure 12:
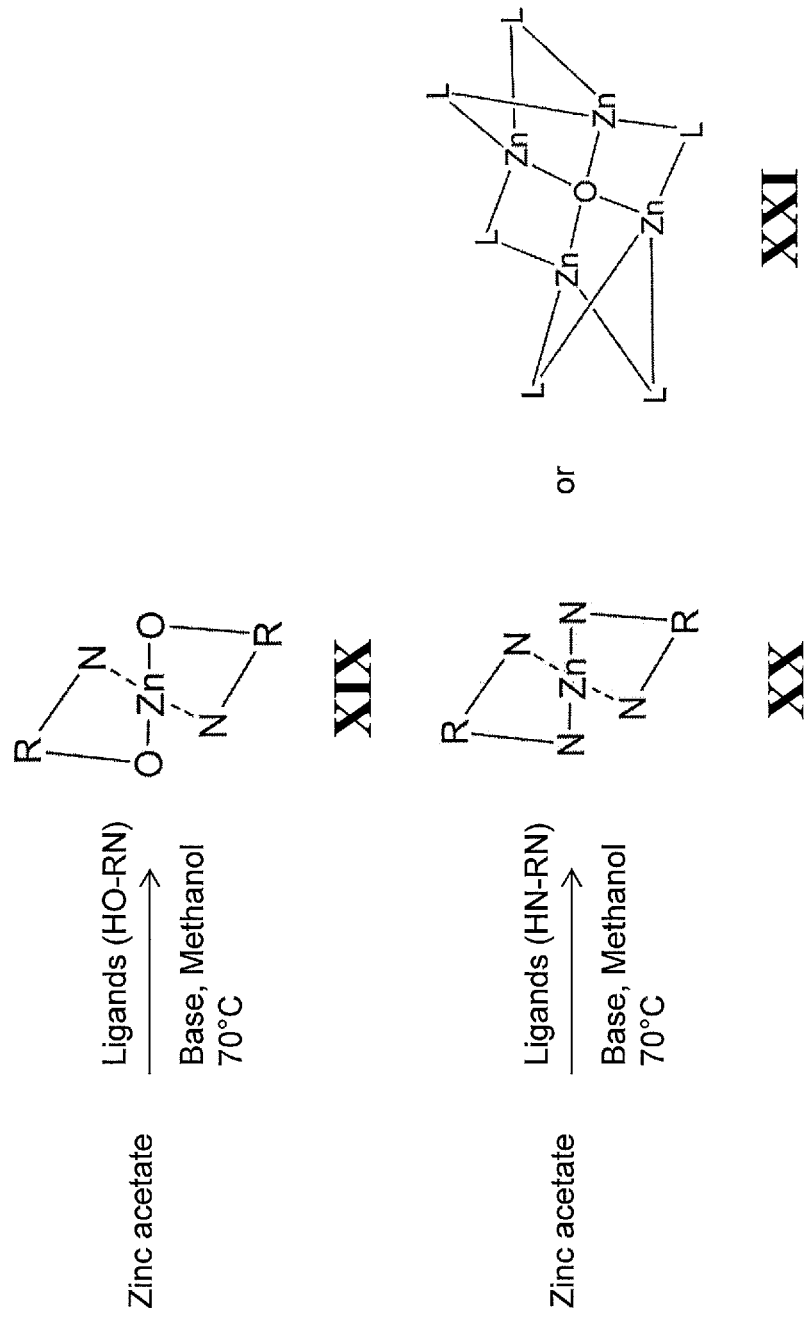
FIG. 12 shows the general synthetic route for zinc coordination complex-based materials (general formulas XIX to XXI).

The absorption spectra showed a very low optical density in the visible range (FIG. 8B). Electron mobilities are as high as $10^{-7}$ up to $10^{-5}$ cm$^2$/Vs (FIG. 8C).

The NDI1 was used as acceptor material in combination with quinacridone (QD) and terButyl quinacridone (BQD) as donors in the following configurations: ITO/8 nm HG01/120 nm QD & NDI1(1:1)/3.5 nmNBPhen/100 nm AlSiCu/100 nm LiF ITO/5 nm MoO3/8 nm HG01/120 nm QD & NDI1(1:1)/3.5 nmNBPhen/100 nm AlSiCu/100 nm LiF ITO/8 nm HG01/120 nm BQD &NDI1(7:3)/3.5 nmNBPhen/100 nm AlSiCu/100 nm LiF ITO/5 nm MoO3/8 nm HG01/120 nm BQD &NDI1 (7:3)/3.5 nmNBPhen/100 nm AlSiCu/100 nm LiF The devices were characterised by measuring IV dark, IV light (1.62 µW/cm2, 550 nm) and action spectra @ 0V and -1V. The results are shown in FIGS. 8D and 8E.

The NDI1 or NMI-NDI1 were used as acceptor materials in combination with Subphtalocyanineclhoride (SubPcCl) as donor in the following configurations: ITO/8 nm HG01/80 nm SubPcCl & NDI1(1:1)/5 nmNBPhen/0.5 nm LiF/100 nm AlSiCu/100 nm LiF ITO/6 nm MoO3/8 nm HTM065/148 nm SubPcCl & NMI-NDI1(1:1)/5=NBPhen/0.5 nm LiF/100 nm AlSiCu/100 nm LiF The devices were characterised by measuring action spectra @ 0V and -1V. The results are shown in FIG. 8F.

Example 5: Further Naphtalene Diimide (NDI)-Based Materials

The naphtalene diimides (NDI) NDI20-26, NDI 28-29 and NDI35-38 have the following chemical structures:

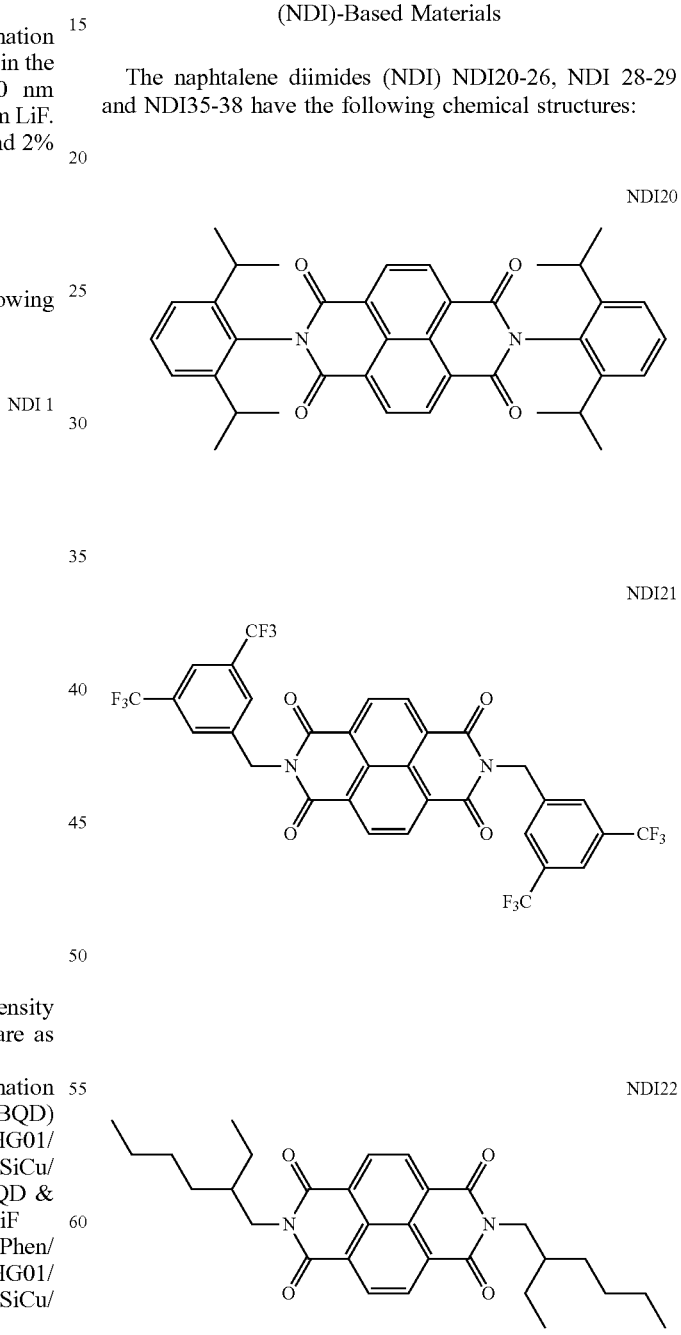

Figure 13:
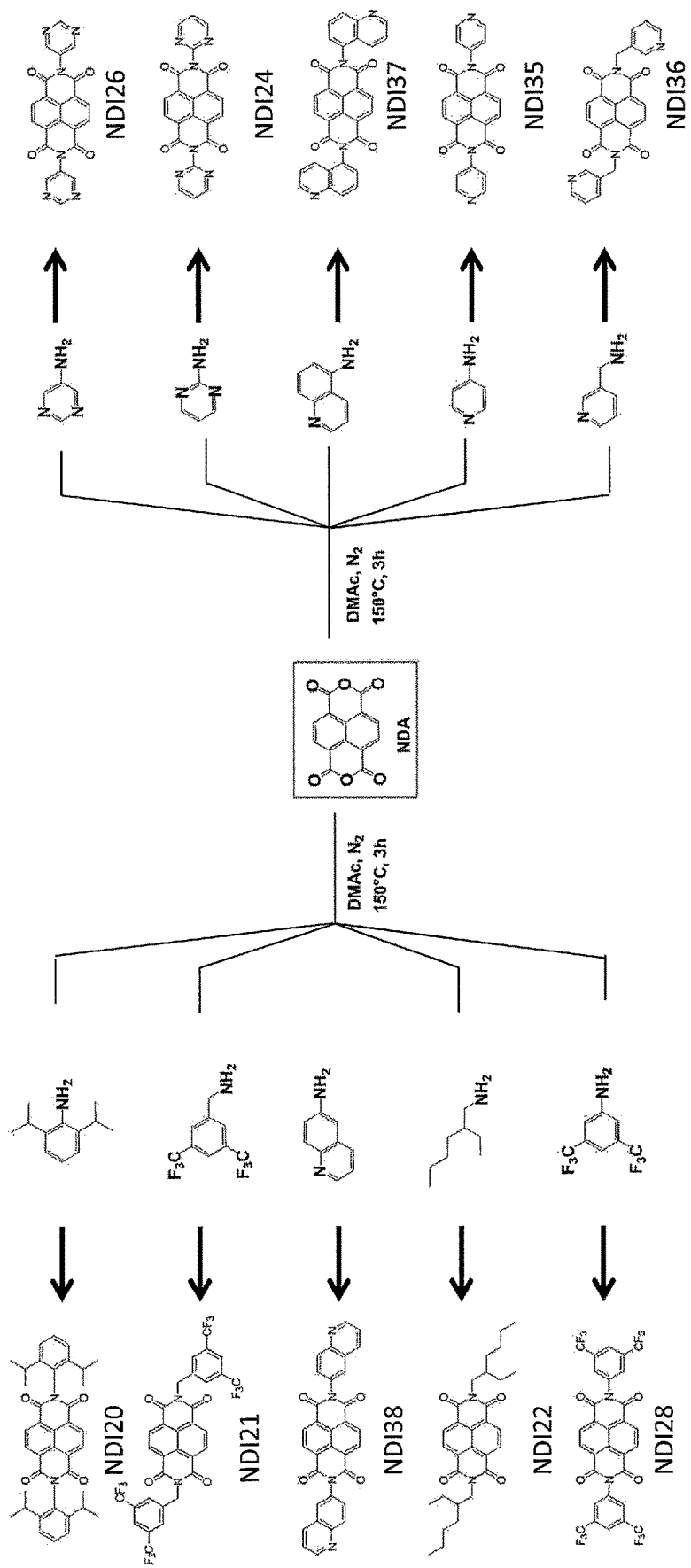
FIG. 13 shows a synthesis overview for transparent n-materials with general formula Ia.
Figure 15:
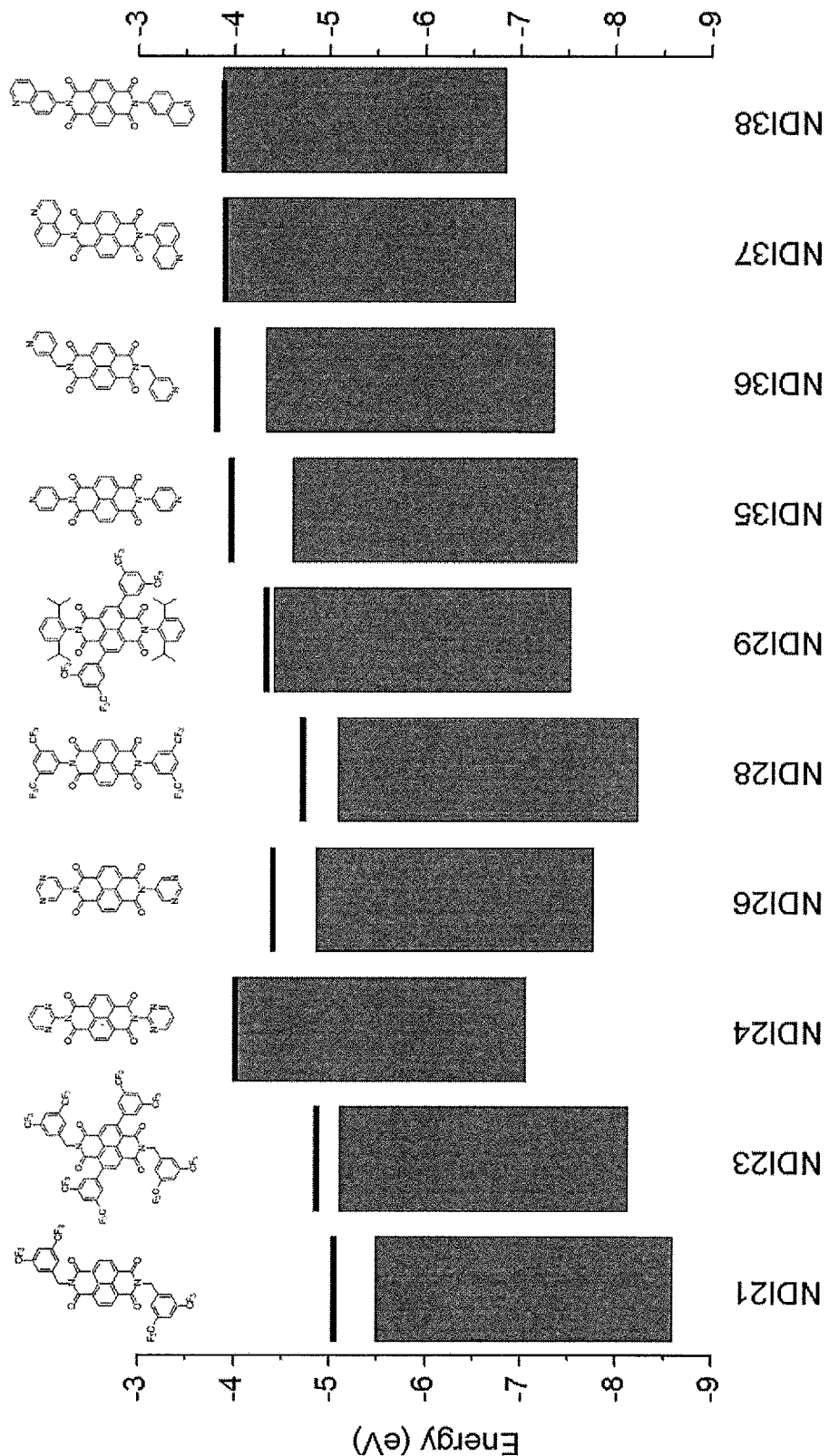
FIG. 15 shows energy levels of N-buffer materials with general formula Ia.
Figure 16:
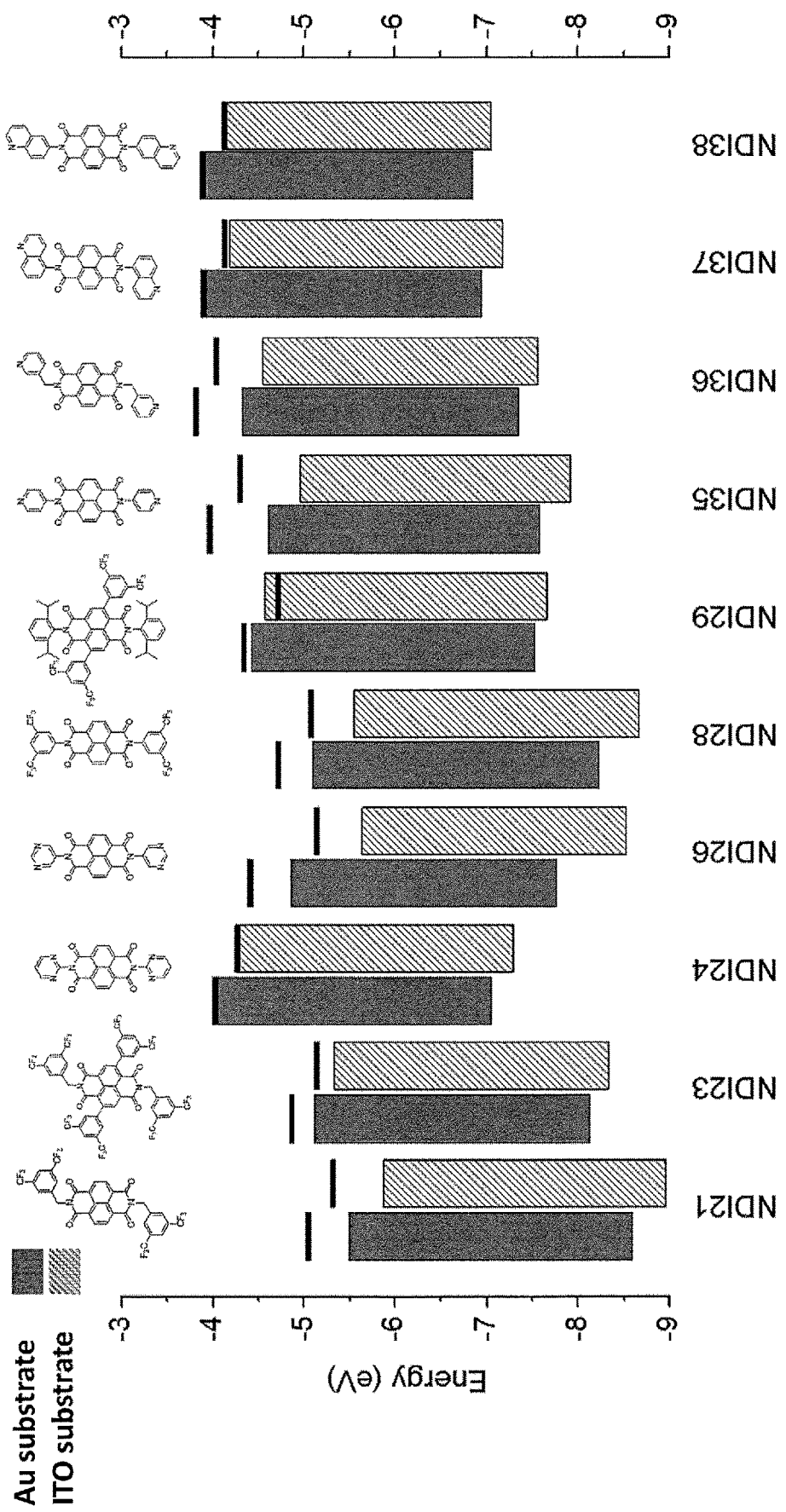
FIG. 16 shows energy levels of N-buffer materials with general formula Ia.
Figure 18:
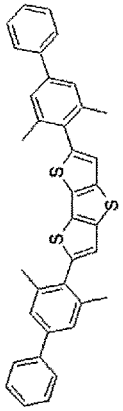
FIGS. 18A and FIG. 18B show transparent p type material examples.
Figure 18:
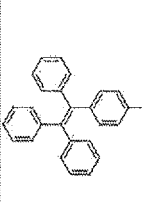
Figure 18:
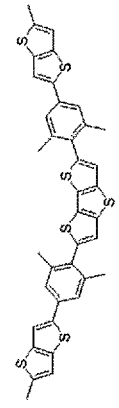
Figure 18:
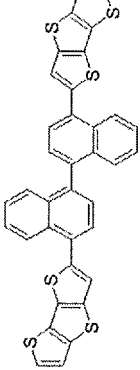
Figure 19:
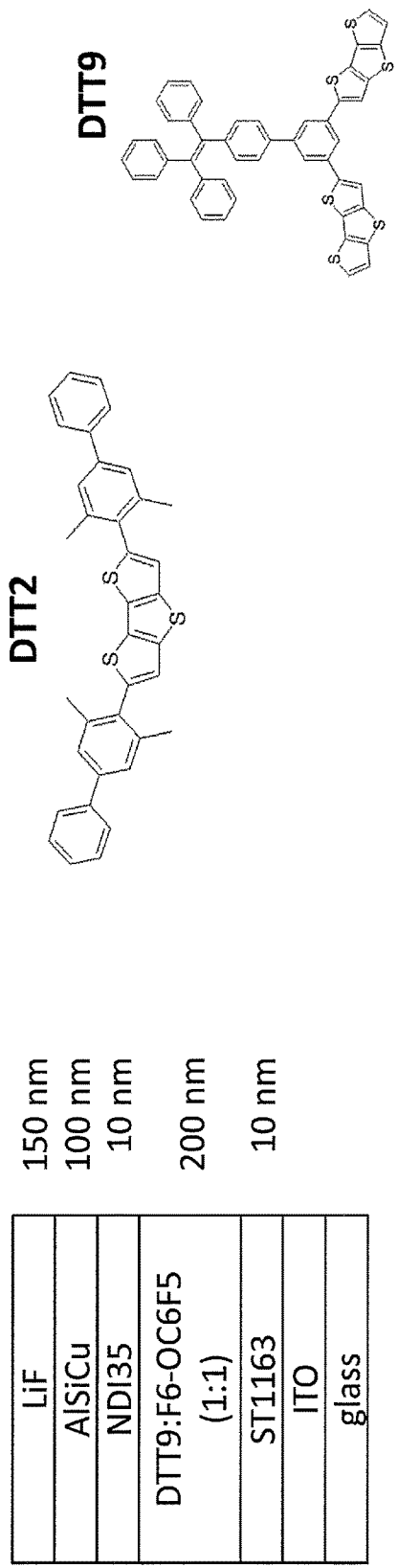
FIGS. 19A-19C and FIGS. 20A-20C show devices of NDI35 as n-buffer with DTT2, DTT9, DTT10 or DTT11, respectively, as p materials.
Figure 19:
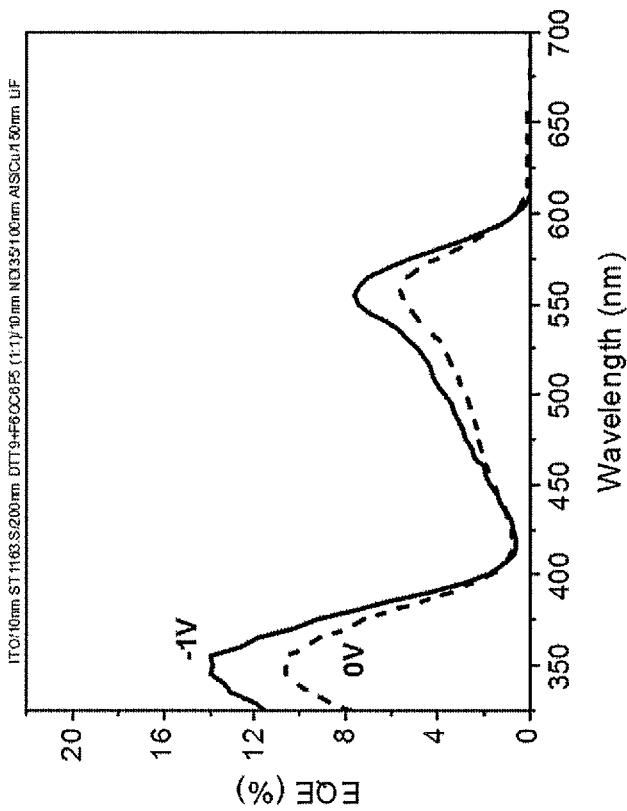
Figure 19:
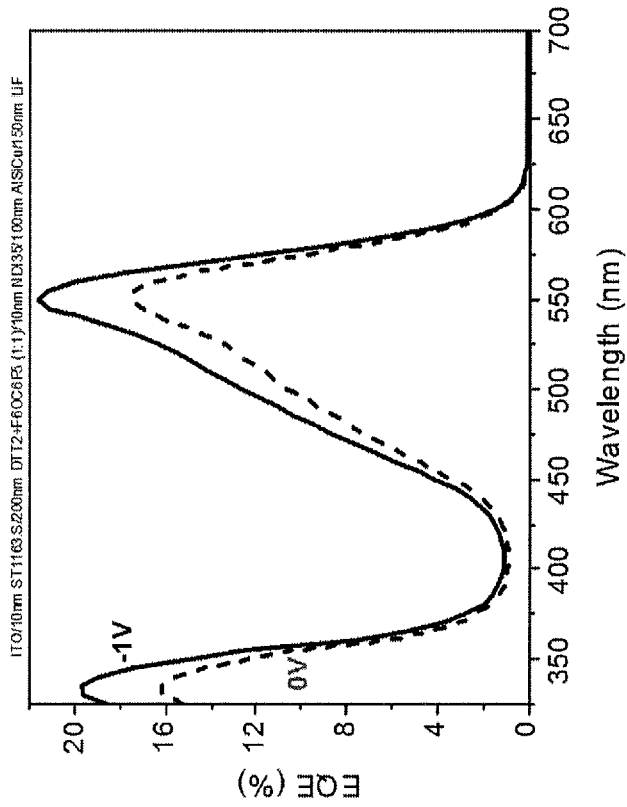
Figure 19:
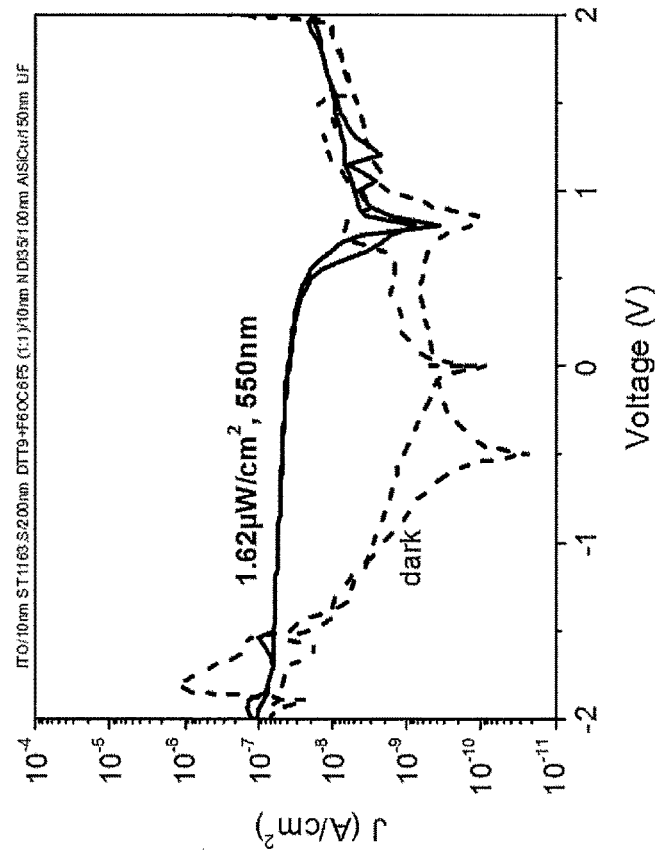
Figure 19:
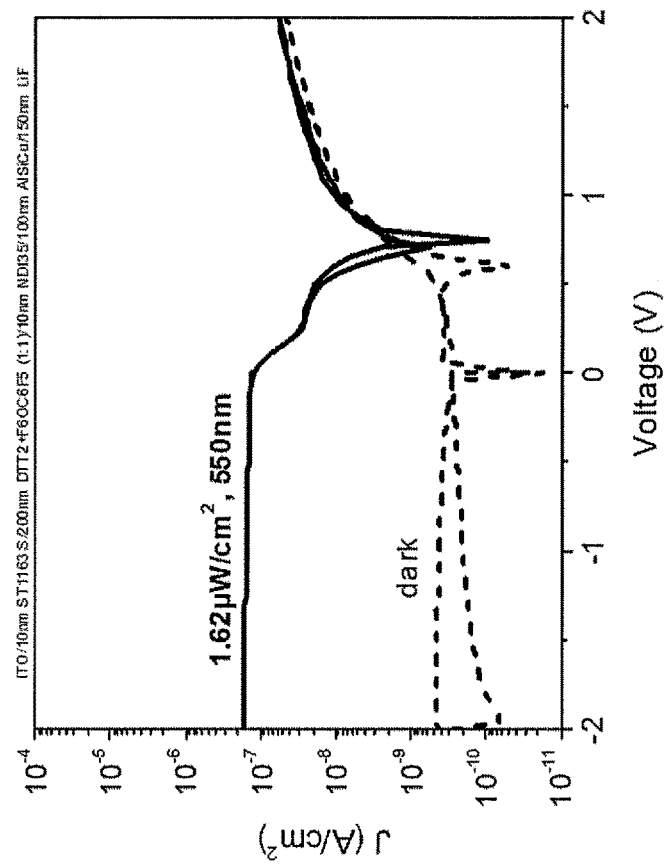
Figure 20:
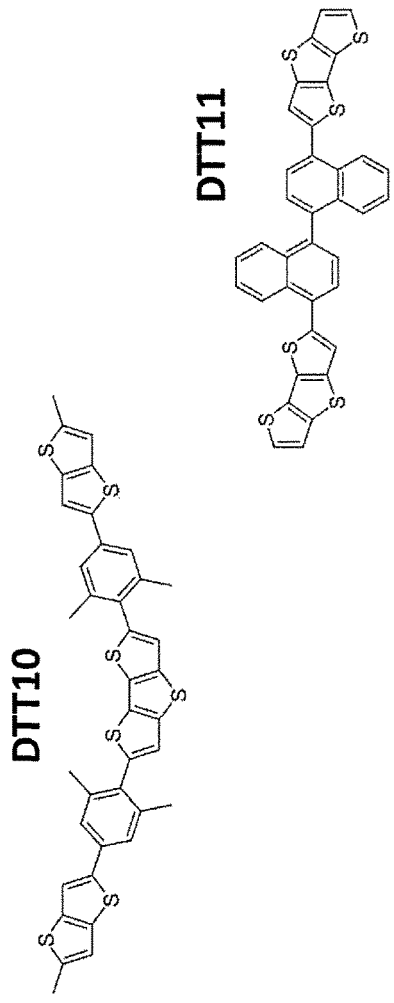
Figure 20:
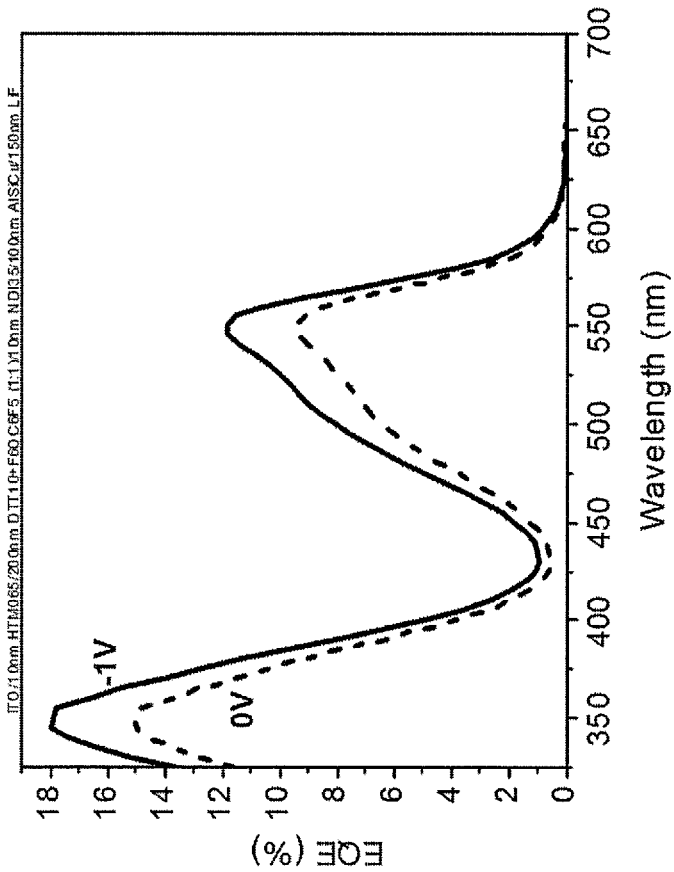
Figure 20:
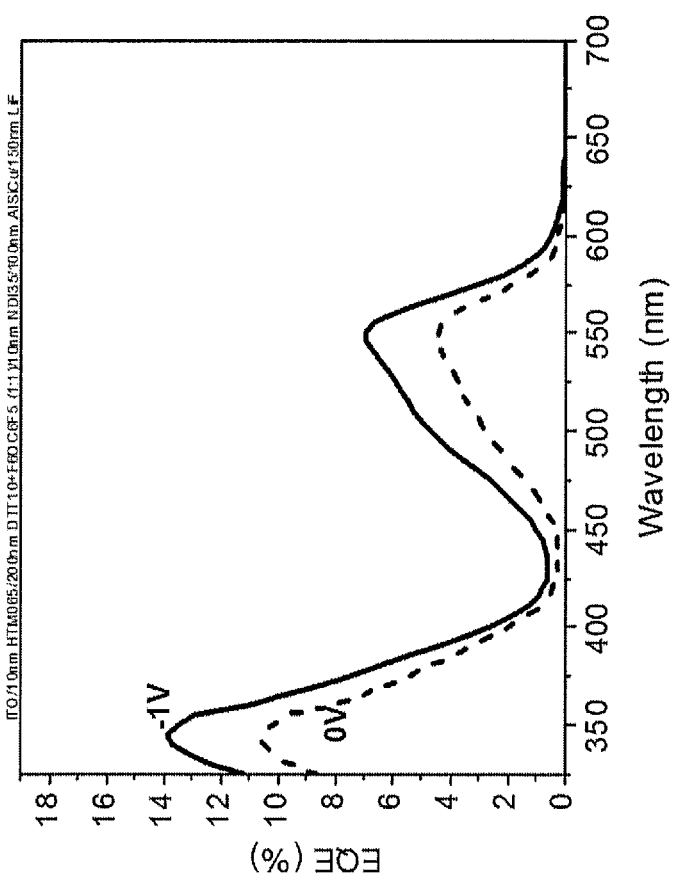
Figure 20:
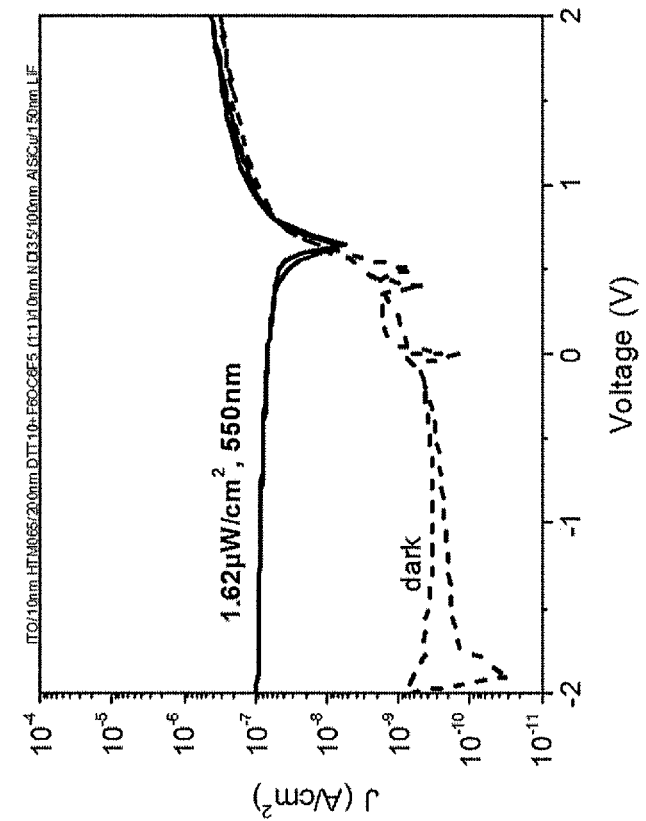
Figure 20:
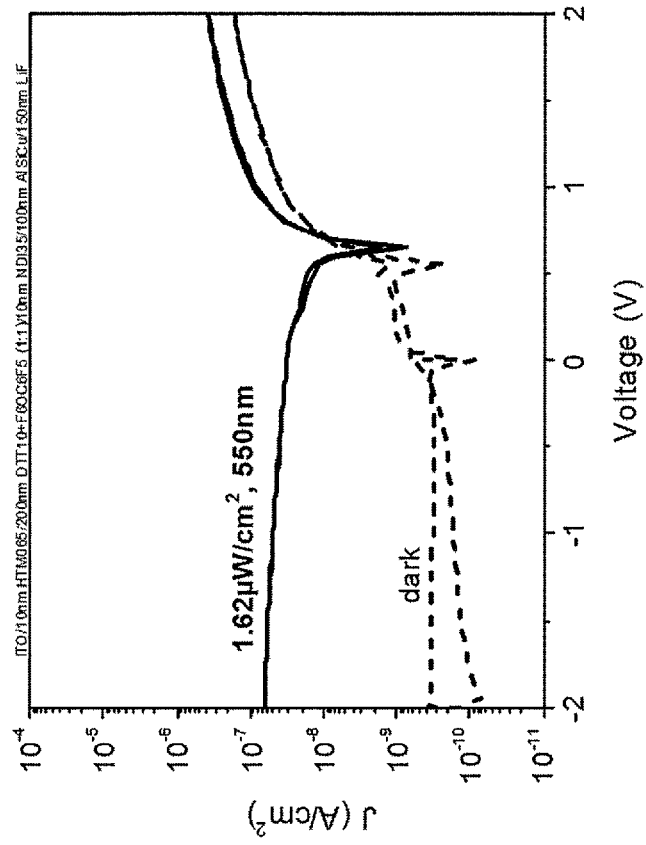

NDI23
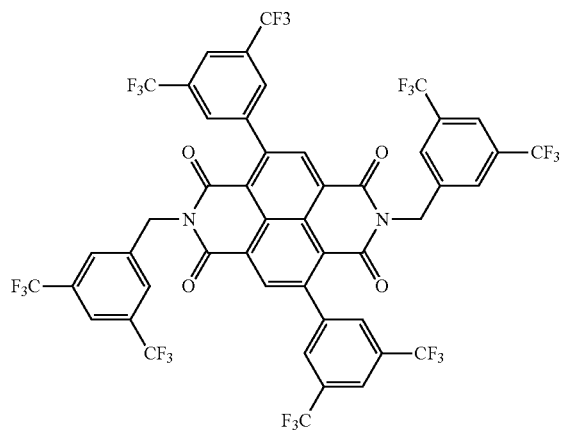
NDI24
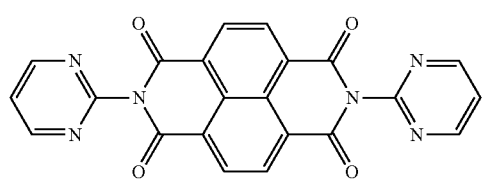
NDI26
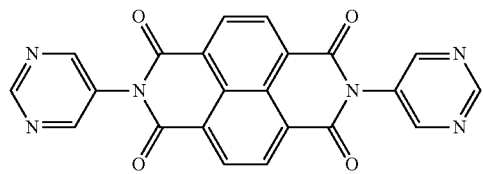
NDI28
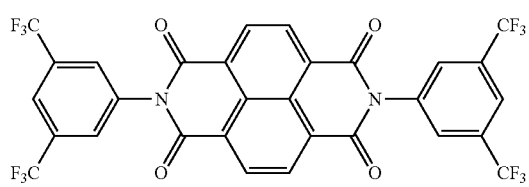
NDI29
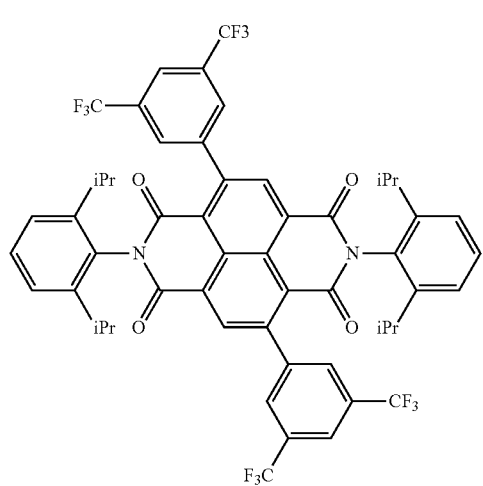
NDI35
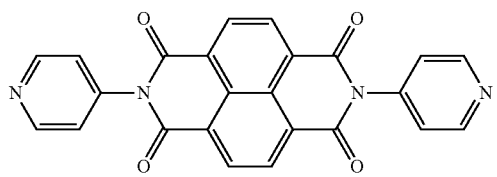
NDI36
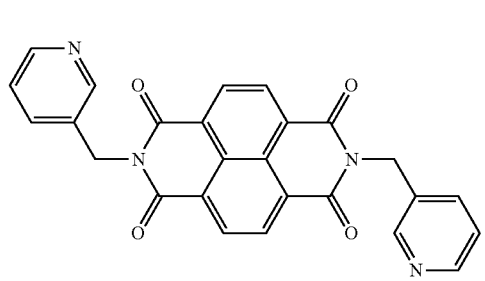
NDI37
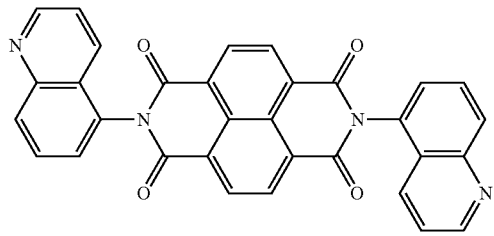
NDI38
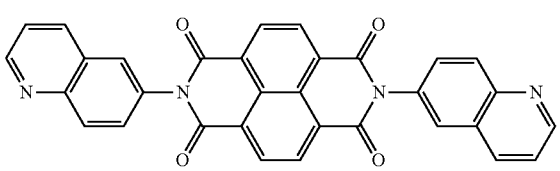
In the scheme shown in FIG. 13, the general synthetic route for the synthesis of the materials is reported.
The NDI materials showed absorption maxima in the range of 379 to 385 nm (FIG. 14).
Energy levels are shown in FIGS. 15 to 17.
Example 6: p-Type Materials
The following p-type materials were synthesized and characterized (see also FIG. 18A and FIG. 18B):

TAT4
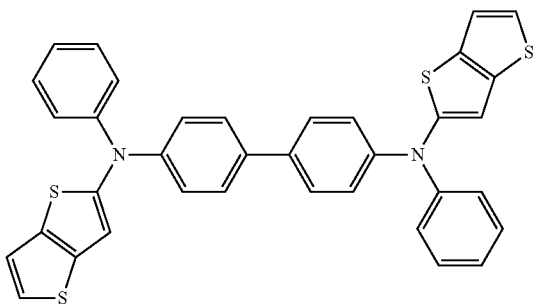
ATA3
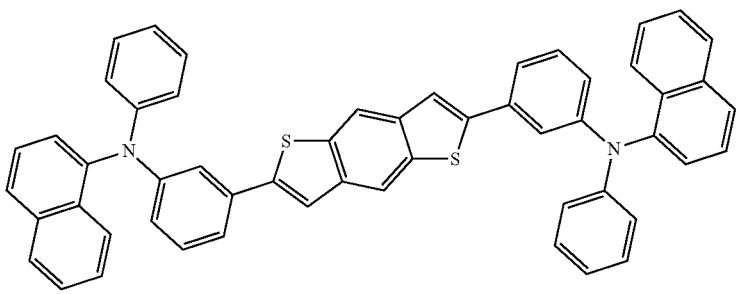
ATA4                                                ATA5
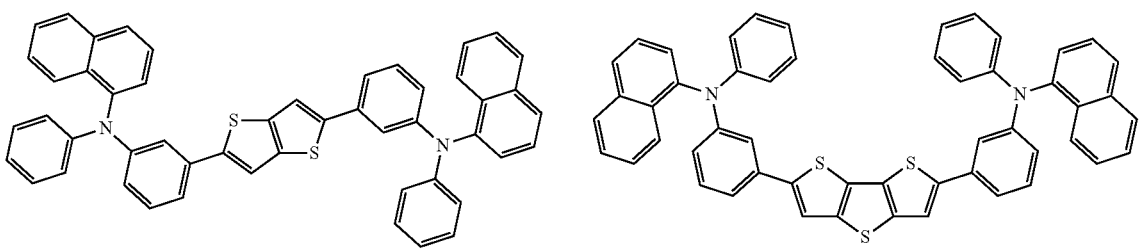
ATA6                                                C2-Th
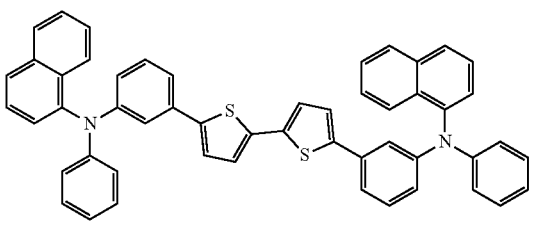 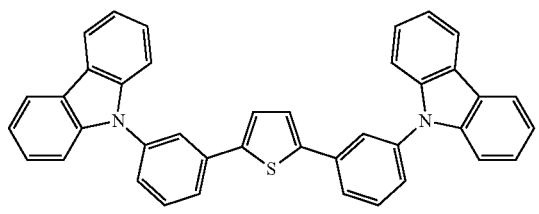
C2-TT                                               C2-DTT
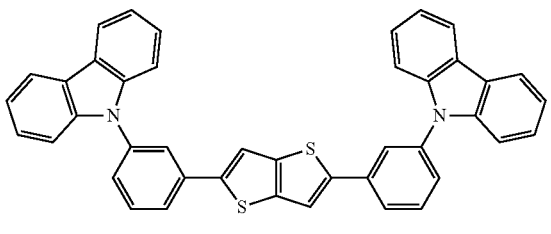 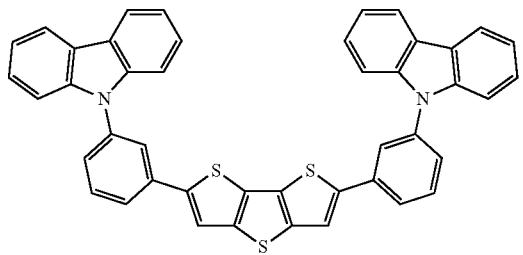

-continued

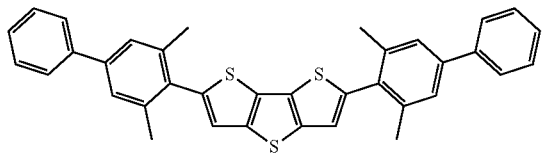
DTT2

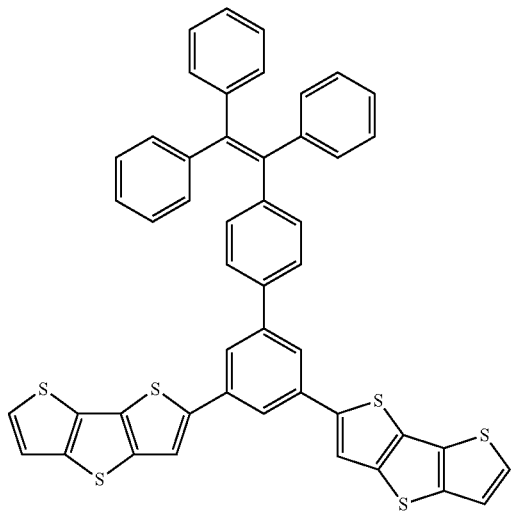
DTT9

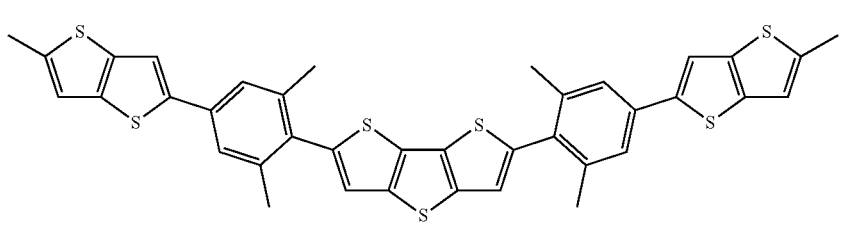
DTT10

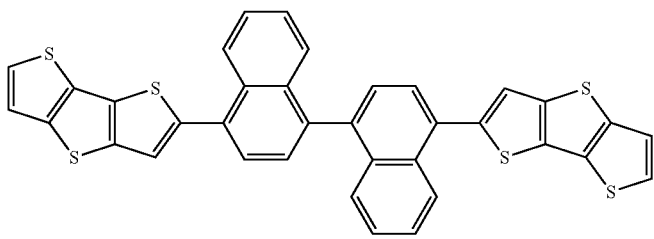
DTT11

NDI35 was used as n-buffer material in devices of DTT2, DTT9, DTT10 or DTT11, respectively, with F6SubPcOC6F5 in the following configurations: LiF 150 nm/AlSiCu 100 nm/NDI35 10 nm/DTT9:F6SubPcOC6F5 (1:1) 200 nm/ST1163 10 nm/ITO/glass.

The devices were characterized, e.g. by measuring action spectra @ 0V and −1V. The results are shown in FIGS. 19A-19C and FIGS. 20A-20C.

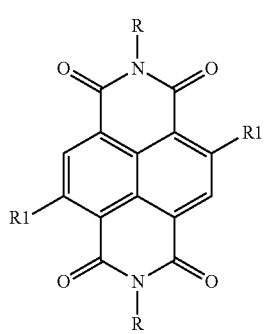
III

The invention claimed is:

1. A transparent P material for a P:N heterojunction or P:N bilayer or multilayer junction, comprising:
a naphthalene dimide based material of formula III, wherein R is, at each occurrence, independently selected from the group consisting of —$C_xH_{2x+1}$, —$C_xX_{2x+1}$, —$C_xH_2X_{2x-1}$,

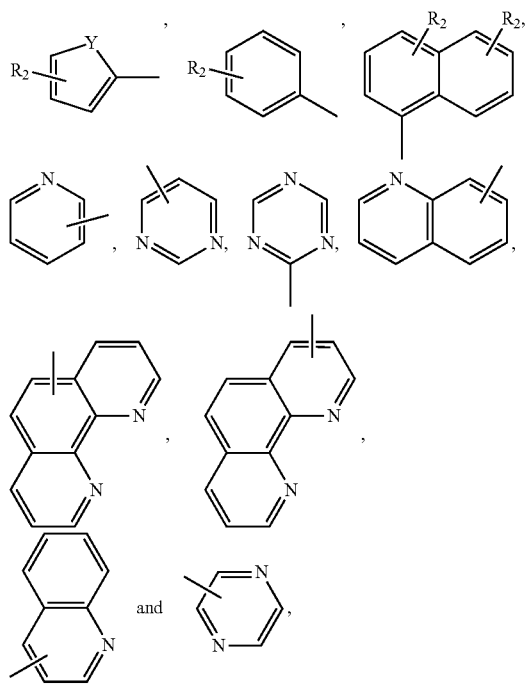

$R_1$ is, at each occurrence, independently selected from the group consisting of

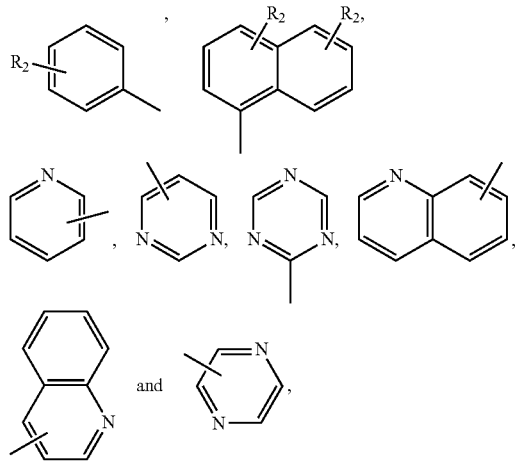

x is an integer from 1 to 10, X is halogen, Y is selected from the group consisting of S, O, Se and N—$R_2$, $R_2$ is, at each occurrence, independently selected from the group consisting of H, a linear or branched alkyl group, a cycloalkyl group, a halogenated alkyl group, a halogen atom, an alkyl or aryl sulfanyl group, an alkyl or aryl amine, an aryl group, a halogenated alkyl group, a heteroaryl group, and a fluorenyl group, and the naphthalene dimide based material dissociates excitons created on colored N or a mixture of colored N materials (N1:N2) or of another colored P or mixture of colored P and N materials (P2:N or P2:N1:N2) via a process of HOMO dissociation in a P:N heterojunction or P:N bilayer or multilayer junction, where transparent refers to an absorption coefficient of less than about 60,000 $cm^{-1}$ in the visible wavelength range in the region from about 400 to about 700 nm, or to an extinction coefficient of less than about 60,000 $M^{-1}cm^{-1}$ in toluene, and colored refers to an absorption coefficient of more than about 60,000 $cm^{-1}$ in the visible wavelength range in the region from about 400 nm to about 700 nm.

2. The transparent P material of claim 1, wherein the naphthalene dimide based material has an absorption coefficient of less than about 60,000 $cm^{-1}$ in the visible wavelength range in the region from about 400 to about 700 nm, or an extinction coefficient of less than about 60,000 $M^{-1}cm^{-1}$ in toluene, and is forming homogenous films formed by a deposition method.

3. The transparent P material of claim 1, wherein R is selected from the group consisting of

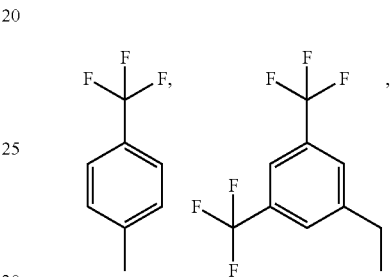

—$(CF_2)_5CF_3$, —$(CH_2)_5CH_3$, —$CH_2$—$(CF_2)_3$—$CF_3$,

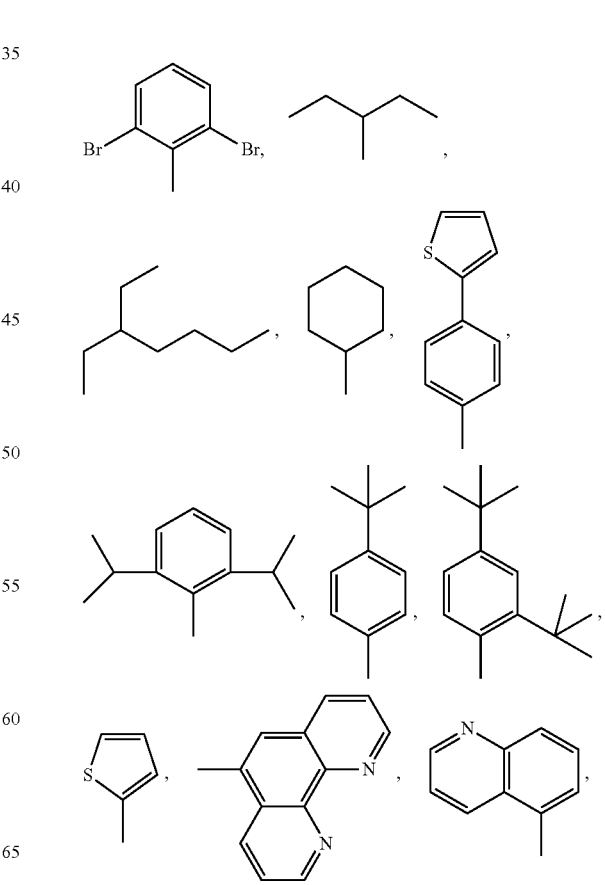

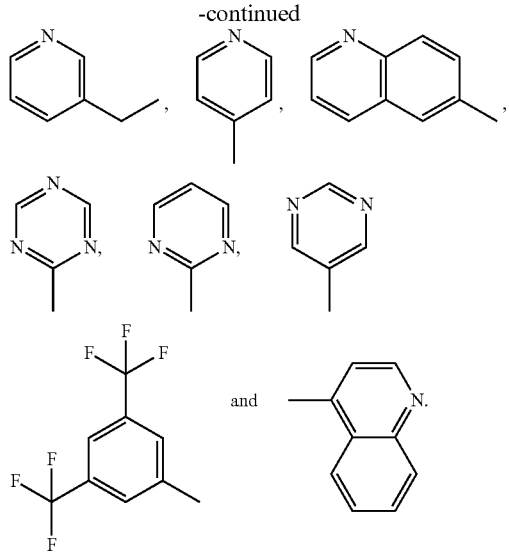
4. The transparent P material of claim 1, wherein $R_1$ is selected from the group consisting of
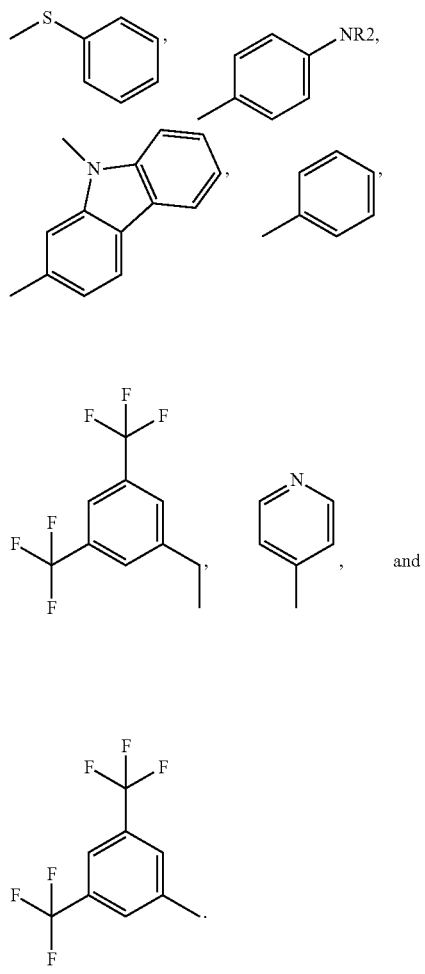
5. The transparent P material of claim 1, wherein R is selected from the group consisting of
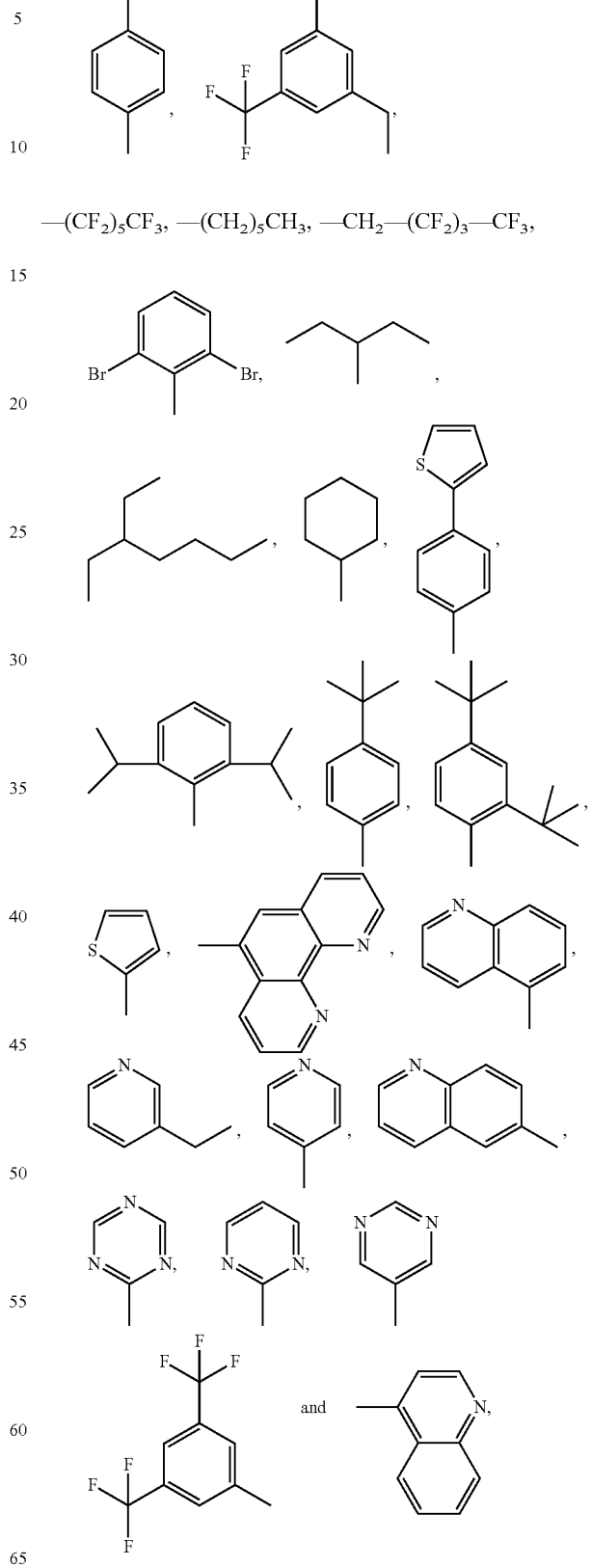

and R₁ is selected from the group consisting of

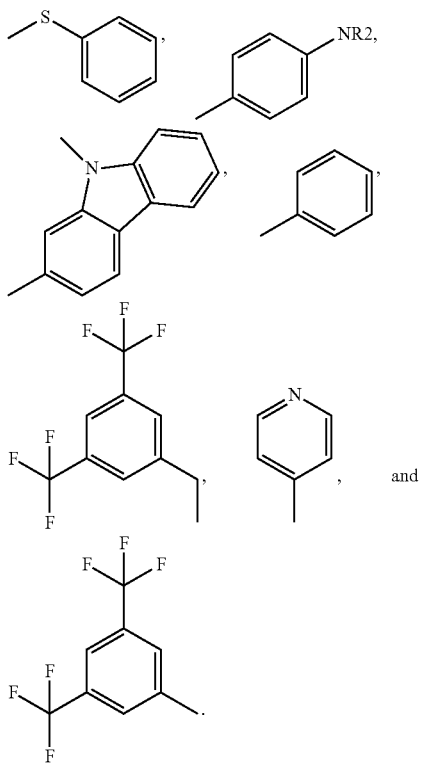

6. The transparent P material of claim 1, wherein the naphthalene dimide based material has an absorption coefficient of less than about 60,000 curl in the visible wavelength range in the region from about 400 to about 700 nm, or an extinction coefficient of less than about 60,000 M⁻¹cm⁻¹ in toluene, and is forming a homogenous film formed by a deposition method.

7. A photoelectric conversion layer, comprising:
the transparent P material of claim 1; and
a further P material.

8. An organic image sensor, comprising:
an organic photoelectric conversion unit comprising the photoelectric conversion layer of claim 7;
at least one electrode; and
a substrate.

9. A hybrid Silicon-organic image sensor or organic image sensor, comprising:
an organic photoelectric conversion unit or units comprising the photoelectric conversion layer of claim 7;
metal wiring;
a CMOS substrate; and
at least one insulating layer.

10. An organic image sensor, comprising:
an organic photoelectric conversion unit comprising the photoelectric conversion layer of claim 7;
an electrode;
a substrate; and
a second electrode on the photoelectric conversion layer.

11. A hybrid Silicon-organic image sensor or organic image sensor, comprising:
an organic photoelectric conversion unit or units comprising the photoelectric conversion layer of claim 7;
a Si based photoelectric conversion unit;
metal wiring;
a CMOS substrate; and
at least one insulating layer.

12. A transparent P material for a P:N heterojunction or P:N bilayer or multilayer junction, comprising:
a naphthalene dimide based material of formula IIIa,

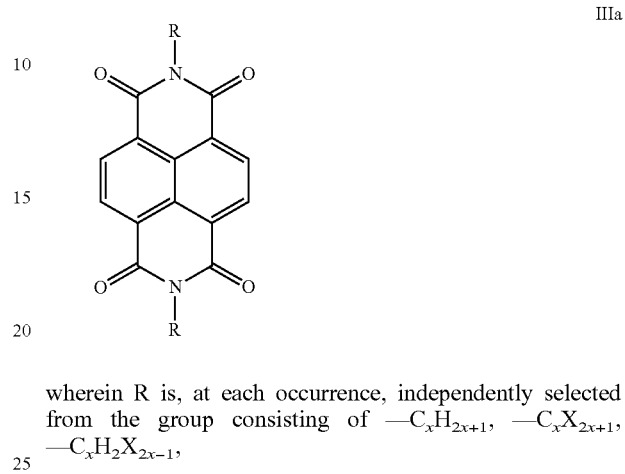

IIIa wherein R is, at each occurrence, independently selected from the group consisting of $-C_xH_{2x+1}$, $-C_xX_{2x+1}$, $-C_xH_2X_{2x-1}$,

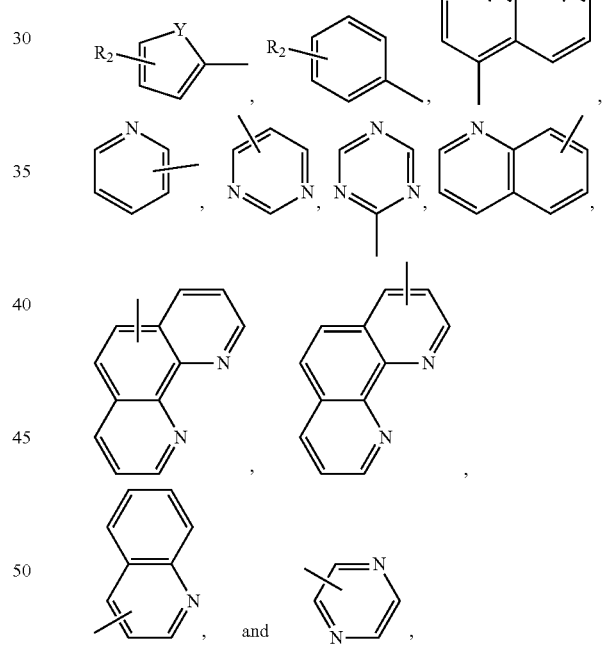

x is an integer from 1 to 10, X is halogen, Y is selected from the group consisting of $CH_2$, S, O, Se and N—R₂, R₂ is, at each occurrence, independently selected from the group consisting of H, a linear or branched alkyl group, a cycloalkyl group, a halogenated alkyl group, a halogen atom, an alkyl or aryl sulfanyl group, an alkyl or aryl amine, an aryl group, a halogenated alkyl group, a heteroaryl group, and a fluorenyl group, and the naphthalene dimide based material dissociates excitons created on colored N or a mixture of colored N materials (N1:N2) or of another colored P or mixture of colored P and N materials (P2:N or P2:N1:N2) via a process of HOMO dissociation in a P:N heterojunction or P:N bilayer or multilayer junction, where transparent refers to an absorption coefficient of less than about 60,000 cm$^{-1}$ in the visible wavelength range in the region from about 400 to about 700 nm, or to an extinction coefficient of less than about 60,000 M$^{-1}$cm$^{-1}$ in toluene, and colored refers to an absorption coefficient of more than about 60,000 cm$^{-1}$ in the visible wavelength range in the region from about 400 nm to about 700 nm.

13. The transparent P material of claim 12, wherein the naphthalene dimide based material has an absorption coefficient of less than about 60,000 cm$^{-1}$ in the visible wavelength range in the region from about 400 to about 700 nm, or an extinction coefficient of less than about 60,000 M$^{-1}$cm$^{-1}$ in toluene, and is forming homogenous films formed by a deposition method.

14. The transparent P material of claim 12, wherein R is selected from the group consisting of

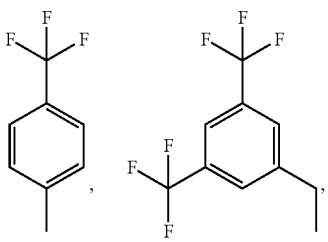

—(CF$_2$)$_5$CF$_3$, —(CH$_2$)$_5$CH$_3$, —CH$_2$—(CF$_2$)$_3$—CF$_3$,

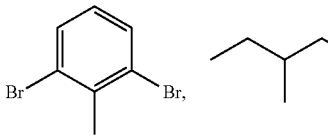

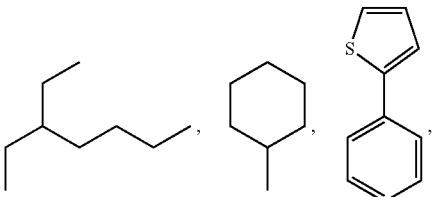

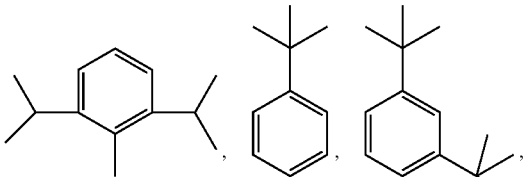

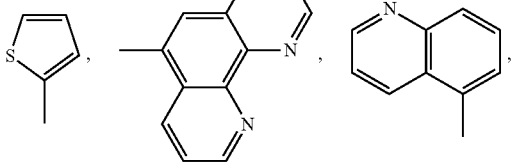

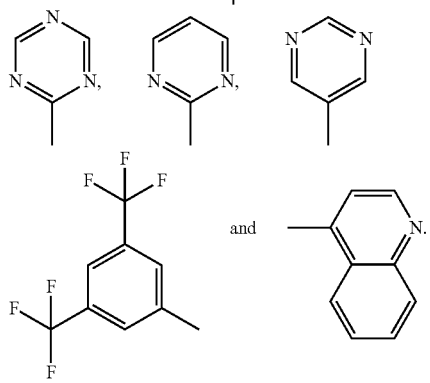

15. The transparent P material of claim 12, wherein the naphthalene dimide based material has an absorption coefficient of less than about 60,000 curl in the visible wavelength range in the region from about 400 to about 700 nm, or an extinction coefficient of less than about 60,000 M$^{-1}$cm$^{-1}$ in toluene, and is forming a homogenous firm formed by a deposition method.

16. A photoelectric conversion layer, comprising:
   the transparent P material of claim 12; and
   a further P material.

17. An organic image sensor, comprising:
   an organic photoelectric conversion unit comprising the photoelectric conversion layer of claim 16;
   at least one electrode; and
   a substrate.

18. A hybrid Silicon-organic image sensor or organic image sensor, comprising:
   an organic photoelectric conversion unit or units comprising the photoelectric conversion layer of claim 16;
   metal wiring;
   a CMOS substrate; and
   at least one insulating layer.

19. An organic image sensor, comprising:
   an organic photoelectric conversion unit comprising the photoelectric conversion layer of claim 16;
   an electrode;
   a substrate; and
   a second electrode on the photoelectric conversion layer.

20. A hybrid Silicon-organic image sensor or organic image sensor, comprising:
   an organic photoelectric conversion unit or units comprising the photoelectric conversion layer of claim 16;
   a Si based photoelectric conversion unit;
   metal wiring;
   a CMOS substrate; and
   at least one insulating layer.

* * * * *